US010087461B2

(12) United States Patent
Bhattacharyya et al.

(10) Patent No.: US 10,087,461 B2
(45) Date of Patent: Oct. 2, 2018

(54) GLYCINE MAX RESISTANCE GENE(S) AND USE THEREOF TO ENGINEER PLANTS WITH BROAD-SPECTRUM RESISTANCE TO FUNGAL PATHOGENS AND PESTS

(71) Applicant: IOWA STATE UNIVERSITY RESEARCH FOUNDATION, INC., Ames, IA (US)

(72) Inventors: Madan K. Bhattacharyya, Ames, IA (US); Micheline Ngaki, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/989,606

(22) Filed: Jan. 6, 2016

(65) Prior Publication Data

US 2016/0194657 A1 Jul. 7, 2016

Related U.S. Application Data

(60) Provisional application No. 62/100,312, filed on Jan. 6, 2015.

(51) Int. Cl.

| | |
|---|---|
| ***C12N 15/82*** | (2006.01) |
| ***C12Q 1/6895*** | (2018.01) |
| ***C12N 9/06*** | (2006.01) |
| ***C12N 9/10*** | (2006.01) |
| ***C07K 14/415*** | (2006.01) |

(52) U.S. Cl.

CPC ........ *C12N 15/8282* (2013.01); *C07K 14/415* (2013.01); *C12N 9/0032* (2013.01); *C12N 9/1007* (2013.01); *C12N 15/8283* (2013.01); *C12N 15/8285* (2013.01); *C12N 15/8286* (2013.01); *C12Q 1/6895* (2013.01); *C12Q 2600/13* (2013.01); *C12Y 105/03011* (2013.01); *C12Y 201/01* (2013.01)

(58) Field of Classification Search

None

See application file for complete search history.

(56) References Cited

U.S. PATENT DOCUMENTS

| | | | | |
|---|---|---|---|---|
| 2004/0031072 A1* | 2/2004 | La Rosa | C07K 14/415 800/278 |
| 2006/0107345 A1 | 5/2006 | Klexandrov et al. | |
| 2007/0234438 A1* | 10/2007 | Abad | C07K 14/415 800/278 |
| 2012/0222167 A1 | 8/2012 | Li et al. | |

FOREIGN PATENT DOCUMENTS

| | | |
|---|---|---|
| WO | 2014117988 A1 | 8/2014 |
| WO | 2014117990 A1 | 8/2014 |

OTHER PUBLICATIONS

Collins, Nicholas C., et al., "SNARE-protein-mediated disease resistance at the plant cell wall", Nature, (2003), vol. 425, pp. 973-977.

Kang, Li, et al., "Interplay of the *Arabidopsis* nonhost resistance gene NH01 with bacterial virulence", PNAS, (2003), vol. 100, No. 6, pp. 3519-3524.

Kuc, Joseph, "Molecular aspects of plant responses to pathogens", ACTA, (1997), vol. 19, No. 4, pp. 551-559.

Sumit, Rishi, et al., "*Arabidopsis* nonhost resistance gene PSS1 confers immunity against an oomycete and a fungal pathogen but not a bacterial pathogen that cause diseases in soybean", BMC Plant Biology, (2012), vol. 12, No. 87, 14 pages.

* cited by examiner

*Primary Examiner* — Medina A Ibrahim

(74) *Attorney, Agent, or Firm* — McKee, Voorhees & Sease, PLC

(57) ABSTRACT

The present invention relates to a method of increasing plant resistance to plant pathogens, particularly Sudden Death Syndrome in soybean against *Fusarium virguliforme*, through the use of *Fusarium* resistance nucleic acid molecules isolated from *Glycine max* and *Fusarium virguliforme*. In these plants, at least one heterologous *Fusarium* resistance protein is introduced in comparison to the wild-type plants to confer resistance to plant pathogens. The invention relates to transgenic plants and/or plant cells having increased resistance to plant pathogens, to expression vectors, transformed plants and plant cells as well as the use of such plants in a plant breeding program.

36 Claims, 26 Drawing Sheets

Specification includes a Sequence Listing.

Leaf tissues treated with water

Leaf tissues treated with 5N NaCl

| Locus ID | S1 | S2 | S3 | S4 | Gene name |
|---|---|---|---|---|---|
| *Glyma18g47390* **(Promoter 1 gene)** | 0 | 0 | 44 | 126 | SAM dependent carboxyl methyltransferase |
| *Glyma10g31210* **(Promoter 2 gene)** | 802 | 421 | 4163 | 6181 | Cupin, nutrient reservoir activity |
| *Glyma20g36300* **(Promoter 3 gene)** | 2442 | 1274 | 5362 | 5065 | Cupin, nutrient reservoir activity |

S1 root tissues harvested 3 to 5 days following water treatment
S2 root tissues harvested 10 to 24 days following water treatment
S3 root tissues harvested 3 to 5 days following *F. virguliforme* infection
S4 root tissues harvested 10 to 24 days following *F. virguliforme* infection

FIG. 20

GLYCINE MAX RESISTANCE GENE(S) AND USE THEREOF TO ENGINEER PLANTS WITH BROAD-SPECTRUM RESISTANCE TO FUNGAL PATHOGENS AND PESTS

CROSS REFERENCE TO RELATED APPLICATION

This application claims priority under 35 U.S.C. § 119 of a provisional application Ser. No. 62/100,312 filed Jan. 6, 2015, which application is hereby incorporated by reference in its entirety.

GRANT REFERENCE

This invention was made with government support under Grant No. 2013-68004-20374 awarded by USDA/NIFA. The government has certain rights in the invention.

FIELD OF THE INVENTION

The present invention is in the field of plant genetics. More specifically, the invention relates to nucleic acid molecules from regions of the *Glycine max* genome which are associated with broad-spectrum pathogen resistance, particularly resistance to *Fusarium virguliforme*. The invention also relates to proteins encoded by such nucleic acid molecules as well as nucleic acid markers which are associated with *Fusarium* resistance. Moreover, the invention relates to uses of such molecules, including, transforming pathogen susceptible plants with constructs containing the nucleic acid molecules to create transgenic plants with enhanced pathogen resistance and the use of such molecules, transformed cells, plants and plant parts in a plant breeding program.

BACKGROUND OF THE INVENTION

Soybean [*Glycine max* L. (Merrill)] is a major oil seed crop and is grown throughout much of the world. The United States alone produces over half of the world output. Soybean seed typically contains 40% protein and 20% oil and is used primarily for livestock feed and industrial purposes, in addition to human consumption. Soybeans are a major cash crop and investment commodity in North America and elsewhere. Soybean oil is one of the most widely used edible oils, and soybeans are used worldwide both in animal feed and in human food production.

Soybean sudden death syndrome (SDS) is a fungal disease of soybean (*Glycine max* (L.)), caused by *Fusarium solani*. Since its discovery SDS has become one of the most destructive pests in soybean. It has been reported in nearly all states that soybean are grown, and it causes production problems in several states, being particularly destructive in Midwestern states. See generally (Mulrooney 1988, Gibson et al., 1994, Hartman et al., 1995, Wrather et al., 1995, 1996). Nationwide, the estimated soybean yield suppression from SDS in 2010 was 2.1% of total yield valued at $0.82 billion. In certain years, SDS causes total crop loss in many soybean fields.

Although the use of fungicides is effective in reducing the population level of the fungus, fungicide use is both uneconomical and environmentally unsound as a control measure in soybean production. Neither is crop rotation a practical means of fungal control since rotation with a non-susceptible crop for at least two years is necessary for reducing soybean losses. Therefore, soybean breeders generally rely on the use of resistant varieties as the most practical control measure.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) flanzenphysiologie, Springer Verlag, Berlin-Heidelberg, Germany).

Resistance to SDS is multigenic and quantitative in soybean (Hnetkovsky et al., 1996; Njiti et al., 1996). Chang et al., (1996, 1997) estimated that Forrest has 5 genes required for resistance to SDS. Njiti et al., (1996) and Kilo et al., (1996) estimated that Pyramid has genes required for resistance to SDS, 2 that were different from those in Forrest. The multiple genes and genetic backgrounds involved contribute to the difficulty breeders have in developing SDS resistant soybean varieties.

It is an object of the present invention to identify and use *Fusarium* resistance genes to engineer or improve SDS resistance in susceptible host plants.

Spider mites are yield-reducing pests in soybean, which feed on the abaxial surface of leaves, and produce symptoms such as yellowing and whitish spot, bronzing, and webbing on the adaxial side of leaves. These symptoms are mostly severe, as these tinny insects multiply very quickly, with one generation being completed as short as in 5 to 8 days (English-Loeb et al., 1998; Shurtleff and Aoyagi, 2009; Scranton et al., 2013). Unfortunately, fewer studies have focused on identifying mite resistant genes.

As can be seen a need exists for identifying and using mite resistant genes to engineer or improve resistance in susceptible host plants.

Soybean aphid, (*Aphis glycines*, Matsumura) is among the major yield-reducing pests of soybean (Zuang et al., 2002). *Aphis glycines* Matsumura, was identified as new insect pest of soybeans in 2001 and spread to over 21 states in the United States and 3 Canadian provinces by 2003 (Vennette et al. Ann Entomol Soc Am 97:217-226 (2004)). High yields are critical to a farmer's profit margin. Soybean aphid can cause over 50% yield losses (Wang et al., Plant Protect 20:12-13 (1994)). In addition to the decrease in yield, an increase in insecticide use can also decrease a farmer's profit margin. Over 7 million acres of soybean in the North Central U.S. were sprayed with insecticide to control soybean aphids in 2003; the estimated cost of the insecticide treatments was $84-$105 million in the North Central region alone in 2003 (Landis et al. NCR-125 Arthropod biological control: state reports for 2003; Li et al., Mol Breeding 19:25-34 (2007)).

It is a further object of the present invention to identify and use aphid resistance genes to engineer or improve SDS resistance in susceptible host plants.

The soybean cyst nematode (SCN), *Heterodera glycines*, is a very serious soybean pest. Female nematodes attack and feed in soybean roots leading to death of the entire plants and therefore severe yield losses occur across the globe (Koenning et al., 2012). Fortunately, genes conferring SCN resistance are deployed to create SCN resistant cultivars to protect the crop losses. Two of these genes have been recently isolated; and both encode distinct novel mechanisms (Cook et al., 2012; Liu et al., 2012). However, there remains a need for identifying and using SCN resistant genes to engineer or improve SCN resistance in susceptible host plants.

Other objects will become apparent from the description of the invention which follows.

SUMMARY OF THE INVENTION

In one aspect, this invention relates to nucleic acid sequences identified and isolated from *Glycine max* and *Fusarium virguliforme*, which are associated with resistance to *Fusarium*. Also, according to the invention, protein sequences are disclosed which are encoded by the same. These sequences alone, or in combination with other sequences, can be used to improve *Fusarium* resistance in susceptible plant species such as soybean. Applicants have also found that these *Fusarium* associated sequences provide broad spectrum resistance to plant pathogens in general including not only fungal pathogens but also insect pathogens such as nematodes, aphids and the like.

In another aspect of the present invention, expression cassettes and transformation vectors comprising the identified and isolated nucleotide sequences are disclosed. The transformation vectors can be used to transform plants to include or increase expression of *Fusarium* resistance genes in transformed cells. Transformed cells as well as regenerated transgenic plants and seeds containing and expressing the isolated and identified DNA sequences and protein products are also provided.

Therefore, in one aspect, the present invention relates to an isolated and identified nucleic acid comprising an isolated polynucleotide sequence encoding a *Fusarium* resistance gene product that confers improved *Fusarium* or SDS resistance. Several resistance genes have been identified according to the invention, including Glyma01g37680.1 (salicylic acid methyl transferases) (SEQ ID NOS: 1 and 2), Glyma12g12470.1 (ankyrin repeat-containing protein) (SEQ ID NOS: 3 and 4), Glyma10g12400.1 (unknown protein) (SEQ ID NOS 5 and 6), Glyma10g32980.1 (sieve element-occulsion protein) (SEQ ID NOS: 7 and 8) and an *F. virguliforme* gene FvPO1 (polyamine oxidase) (SEQ ID NOS: 9 and 10). Sequences reported above are non-limiting examples of potential coding sequences of these genes recited herein.

In a further aspect, the present invention includes a nucleic acid selected from: (a) an isolated polynucleotide encoding a polypeptide of the present invention; (b) a polynucleotide having at least 90% or 95% identity to a polynucleotide of the present invention; (c) a polynucleotide comprising at least 50 or more nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (e). The present invention also provides a method of investigating a haplotype of a plant comprising: (A) isolating nucleic acid molecules from the plant; (B) determining the nucleic acid sequence of a *Fusarium* resistance gene; and, (C) comparing the nucleic acid sequence of the allele or part thereof to a reference nucleic acid sequence. The present invention further provides a method of introgressing *Fusarium* resistance or improved *Fusarium* resistance into a susceptible plant comprising: performing marker assisted selection of the plant with a nucleic acid marker, wherein the nucleic acid marker specifically hybridizes with a nucleic acid molecule encoding a *Fusarium* resistance gene reported herein and, selecting the plant based on the marker assisted selection.

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. Thus, the invention is also directed to transgenic cells, containing the nucleic acids of the present invention as well as cells, plants, tissue cultures and ultimately lines derived therefrom. The invention also relates to vectors and cassettes designed to introduce the expression of *Fusarium* resistance proteins for modulation of the *Fusarium* interaction, or for delineation of information about the regulatory pathways involving the same.

This invention also provides an isolated polypeptide comprising (a) a polypeptide comprising at least 90% or 95% sequence identity to a polypeptide of the present invention (b) a polypeptide encoded by a nucleic acid of the present invention; and (c) a polypeptide comprising a *Fusarium* resistance activity and comprising conserved structural domain motifs of the same.

Another embodiment of the subject invention includes methods for engineering broad-spectrum pathogen resistance in soybean or other *Fusarium* susceptible crop plants by introducing a *Fusarium* resistance protein or its coding sequence to said plants. A plants' tolerance to *Fusarium* and other soybean pathogens may be improved by elucidating the pathways that regulate gene transcription for enhancing accumulation of the *Fusarium* resistance protein products disclosed herein. These methods can provide, for example, increased nonspecific resistance to particularly virulent races or strains of pathogenic agents including *P. sojae, Pseudomonas syringae* pv. *glycenia* (Psg), soybean cyst nematode (SCN), soybean aphids, spider mites, *Fusarium virguliforme* or soybean mosaic virus.

Nucleotide sequences isolated from the *Fusarium* resistance genes can be used in developing perfect molecular markers that can be routinely used in breeding programs for incorporating *Fusarium* resistance into new cultivars.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By “amplified” is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Prin-*

*ciples and Applications*, D. H. Persing et al., Ed., American Society for Microbiology, Washington, D.C. (1993). The product of amplification is termed an amplicon.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, S5 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, the term "*Fusarium* resistance protein" shall include any amino acid sequence which retains one or more of the resistance improving properties of the proteins listed. Such proteins may include salicylic acid methyl transferases (SEQ ID NO: 2), ankyrin repeat-containing protein (SEQ ID NO: 4), unknown protein (SEQ ID NO: 6), sieve element-occulsion protein (SEQ ID NO: 8) *F. virguliforme* polyamine oxidase (SEQ ID NO: 10), and any conservatively modified variants, fragments, and homologs or full-length sequences incorporating the same which retain the *Fusarium* resistance activity described herein. Resistance proteins are capable of suppressing, controlling, and/or preventing invasion by the pathogenic organism. A resistance protein will reduce the disease symptoms resulting from pathogen challenge in a previously susceptible plant by at least about 2%, including but not limited to, about 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater. In particular embodiments, the disease symptoms resulting from pathogen challenge are reduced by non-host resistance protein by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. Resistance may vary from a slight increase in tolerance to the effects of the pathogen (e.g., partial inhibition) to total resistance such that the plant is unaffected by the presence of the pathogen. An increased level of resistance against a particular pathogen or against a wider spectrum of pathogens may both constitute complete resistance or improved resistance.

"Pathogen resistance", "disease resistance" or "*Fusarium* resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing a non-host resistance polypeptide shows a decrease in tissue necrosis (i.e., lesion diameter) or a decrease in plant death following pathogen challenge when compared to a control plant that was not engineered to express the *Fusarium* resistance protein.

Alternatively, antipathogenic activity can be measured by a decrease in pathogen biomass. For example, a plant expressing non-host resistance protein is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) Plant Biology 95:15107-15111, herein incorporated by reference. According to the invention, the term "increased resistance" (against *Fusarium* sp.) is understood to mean that the transgenic plants, or plant cells, according to the invention are less vigorously, and/or less frequently, affected by *Fusarium* than non-transformed wild type plants, or plant cells, which were otherwise treated in the same way (such as climate and cultivation conditions, pathogen type, etc.). According to the invention, the term "wild type" is to be understood as the respective non-genetically modified parent organism. The penetration efficiency as well as the rate of papillae formation offer a possibility to quantify the reaction of the plant to the pathogen infestation (see examples). The term "increased resistance" also comprises what is known as transient pathogen resistance, i.e. the transgenic plants, or plant cells, according to the invention have an increased pathogen resistance as compared to the respective wild type only for a limited period of time.

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual,* 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acids Probes*, Part I, Chapter 2, Ausubel, et al., Eds., Greene Publishing and Wiley-Interscience, New York (1995). In general, a high stringency wash is 2×15 min in 0.5×SSC containing 0.1% SDS at 65° C.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, *CABIOS* 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information World Wide Web at ncbi.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) The terms "substantial Identity" in the context of a peptide indicates that a peptide comprises a sequence with at least 70% sequence identity to a reference sequence, preferably 80%, or preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DESCRIPTION OF THE FIGURES

FIG. 1A shows the generation of three GmARP1 transgenes. The GmARP1 gene was fused to three promoters of soybean genes, Prom 1 (Glyma18g47390, SEQ ID NO: 11), Prom 2 (Glyma10g31210, SEQ ID NO: 12), and Prom 3 (Glyma20g36300, SEQ ID NO: 13), in a binary vector (pTF102 derivative). Binary plasmids carrying the three fusion genes were digested with XbaI and BstXI. FIG. 1B shows the molecular characterization of soybean transformants carrying the Prom2-GmARP1 transgene. (i) PCR amplification of GmARP1 (SEQ ID NO: 3) transgene using one GmARP1-specific and one vector-specific primer. (ii) PCR amplification of the bar gene. Lines 3, 7, through 23 are independent R0 plants.

FIG. 2A shows the root phenotype of a resistant (R) and a susceptible (S) R1 progeny of a transformant carrying the Prom2-ARP1-7 fusion gene. The seedlings were grown for four weeks in a single cup carrying *F. virguliforme* inocula amended soil. FIG. 2B shows enhanced foliar SDS resistance among R1 progenies. Percent $R_1$ progenies with different disease scores. Approximately 30 to 50% of the $R_1$ plants showed enhanced foliar SDS resistance with no symptoms to slight yellowing with disease scores 1 and 2. The rest showed severe disease symptoms with interveinal to severe chlorosis and necrosis with disease scores 3 to 7. The SDS susceptible line, Williams 82 (W82) and the SDS resistant line, MN1606 were used as controls. FIG. 2C shows enhanced root SDS resistance among R1 progenies. Extent of root resistance to the pathogen was expressed as the proportion of healthy roots with no obvious blackening caused by necrosis and rotting due to infection of *F. virguliform*. FIG. 2D shows expression of GmARP1 transgenes. Two random SDS resistant R1 progenies from each R0 line were analyzed. Top panel, resistant plants (two representatives from each line). Bottom panel, susceptible plants (two representatives from each line). Red arrow, GmARP1 (SEQ ID NO: 3); black arrow, ELF1b internal control.

FIG. 3A shows the average disease scores at four different scoring days for resistant and susceptible plants of each transgenic line carrying GmARP1 under the control of either Prom1 (SEQ ID NO: 11), Prom2 (SEQ ID NO: 12), or Prom3 (SEQ ID NO: 13). FIG. 3B shows the average disease scores for Williams 82 (W82) susceptible control. (i) Average disease score for MN1606 resistant control. n represents the number of plants in each category. FIG. 3C shows the percentage of plants resistant to *F. virguliforme* for each line tested.

FIG. 5 shows the molecular characterization of soybean transformants carrying the Prom2-GmSAMT1 transgene.

More likely, the resistant progeny lines were homozygous for the transgenes. Symptoms scored after four weeks following planting seeds in soil mixed with *F. virguliforme* inoculum. Class 1-2, no symptoms to slight yellowing; Class 3-6, interveinal to severe chlorosis and necrosis. W82, Williams 82 is an SDS susceptible soybean line; MN1606 is an SDS resistant soybean line.

Figure 7A:
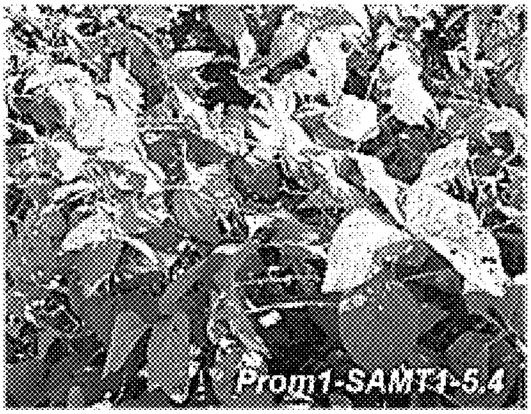
Figure 7B:
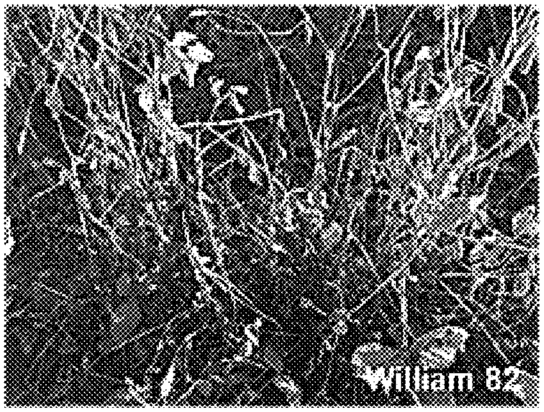
Figure 7C:
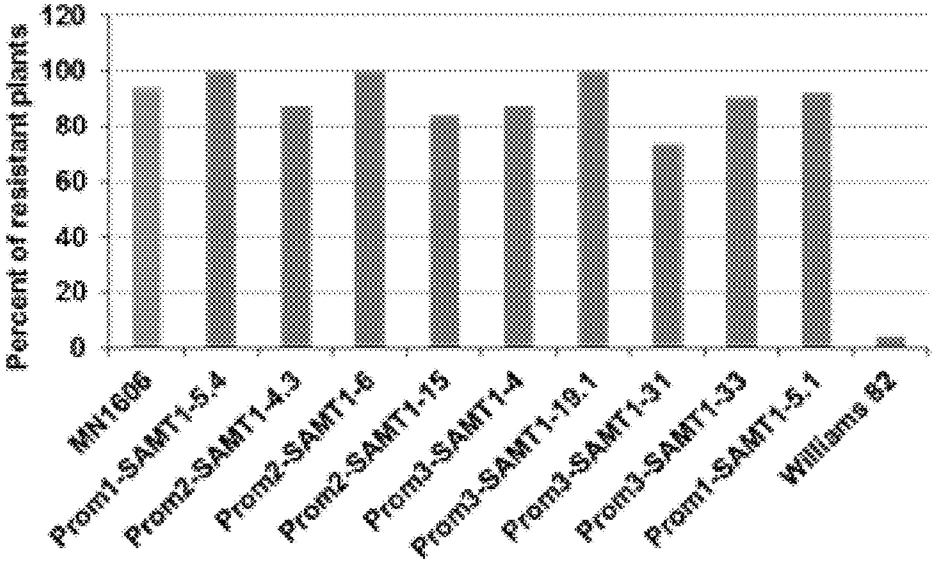

FIGS. 7A-7C show the expression of GmSAMT1 (SEQ ID NO: 1) enhanced SDS resistance in transgenic soybean plants in a field trial. $R_1$ plants were tested for resistance to *F. virguliforme* in field conditions in summer 2015 (June to October). FIG. 7A shows SDS resistant phenotype of GmSAMT1 transgenic soybean plants in a field trial. GmSAMT1 lines were resistant to *Fusarium virguliforme*. FIG. 7B shows Williams 82 plants were susceptible. Picture taken on October 7 (last scoring date) while the plants were maturity stage (R-stage) 6.0. FIG. 7C shows the percentages of plants that were resistant to *F. virguliforme*. Prom1-SAMT1-5.4, represent a resistant line of Prom1-Gm-SAMT1-5 transgenic line. All nine transgenic lines of GmSAMT1 showed more than 73% of plants resistant to *F. virguliforme* with no symptoms to slight yellowing with disease scores 0 and 1. The rest (less than 27%) showed severe disease symptoms with interveinal to severe chlorosis and necrosis with disease scores 2 to 7.

Figure 8A:
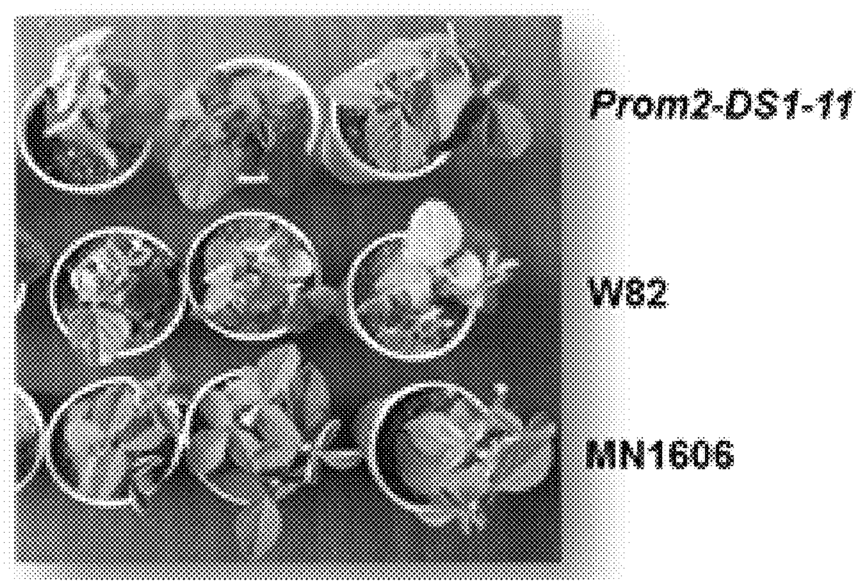
Figure 8B:
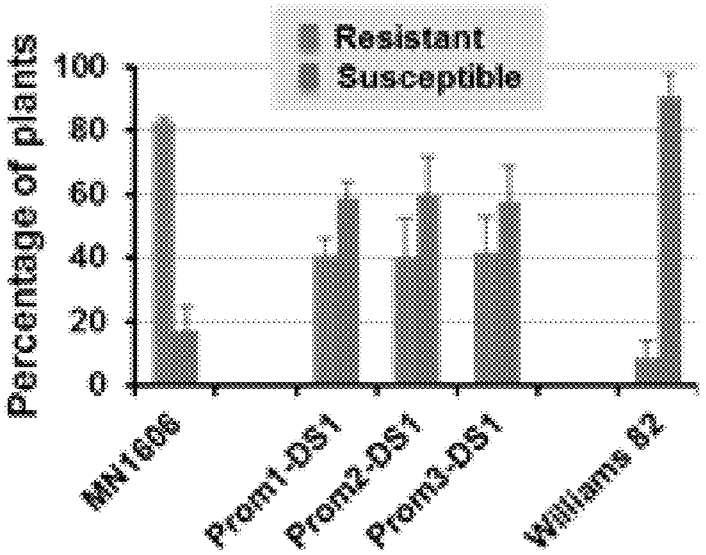
Figure 8C:
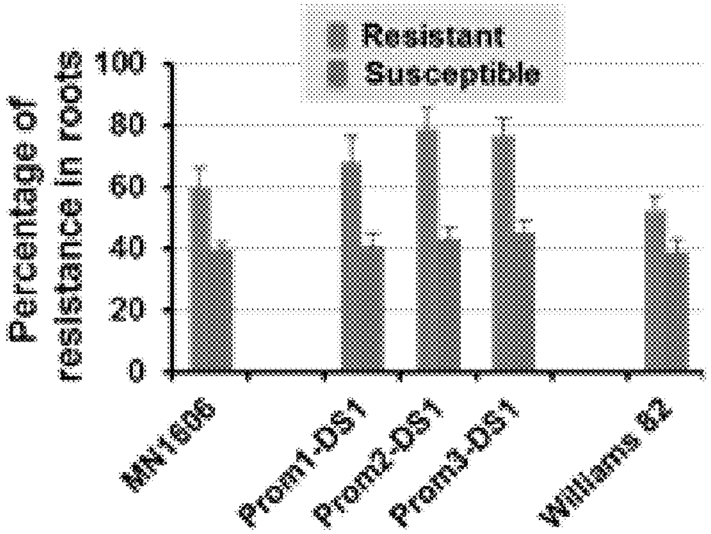
Figure 8D:
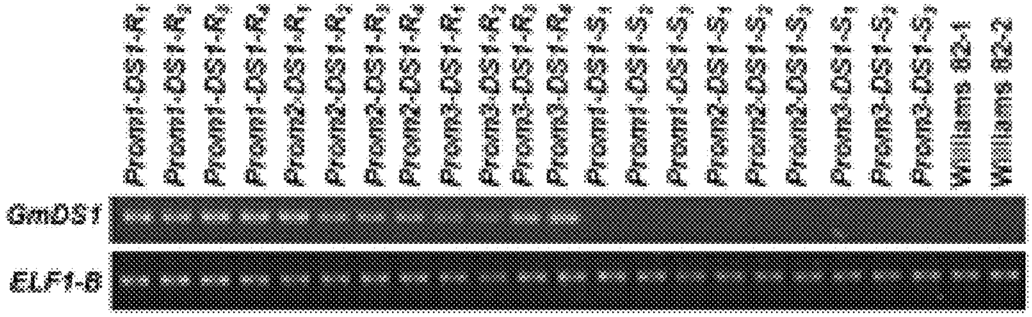

FIG. 8A shows resistant phenotype of $R_1$ progeny of a transformant carrying the Prom2-DS1 fusion gene. Williams 82, the recipient cultivar and is a SDS susceptible line, and MN1606 is a SDS resistant line. The seedlings were grown for four weeks in a single cup carrying *F. virguliforme* inoculum amended soil. FIG. 8B shows enhanced foliar SDS resistance among $R_1$ progenies. Approximately 40% of the $R_1$ plants from each line showed enhanced foliar SDS resistance with no symptoms to slight yellowing with disease scores 1 and 2. The rest showed severe disease symptoms with interveinal to severe chlorosis and necrosis with disease scores 3 to 7. FIG. 8C shows enhanced root resistance among $R_1$ progenies. Extent of root resistance to the pathogen was expressed as the proportion of healthy roots with no obvious blackening caused by necrosis and rotting from infection of *F. virguliform*. FIG. 8D shows expression of GmDS1 (SEQ ID NO: 5) transgenes. Two random SDS resistant $R_1$ progenies from each $R_0$ line were analyzed. Twelve lanes on the left of the gel show the RT-PCR products amplified from the SDS resistant $R_1$ progenies. Rest lanes on the right include nine SDS susceptible R1 progenies and two Williams 82 samples. Upper panel is for the RT-PCR products of GmDS1 (SEQ ID NO: 5) and lower panel is for ELF1b as an internal control.

Figure 9A:
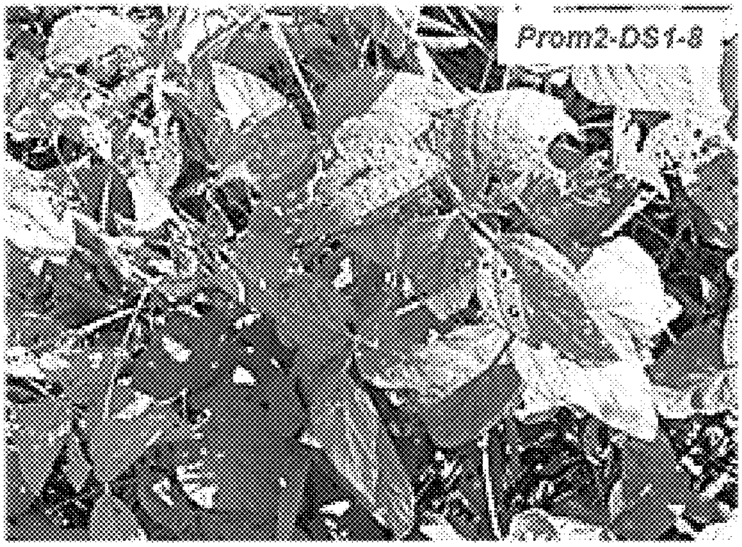
Figure 9B:
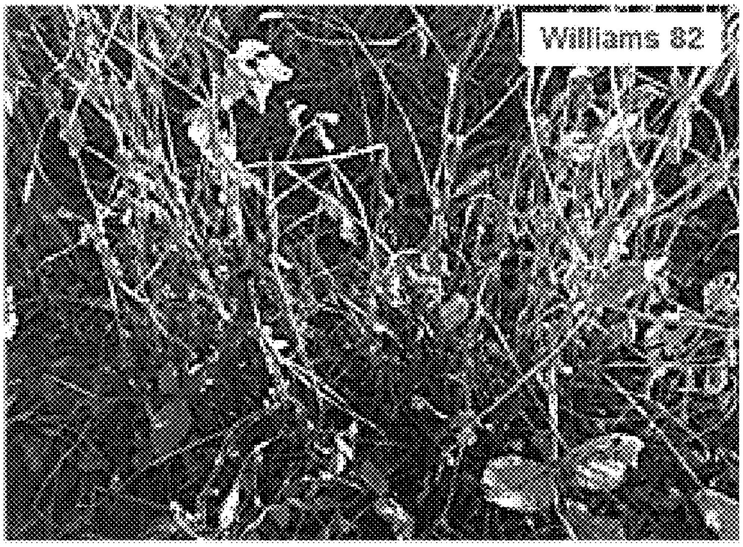
Figure 9C:
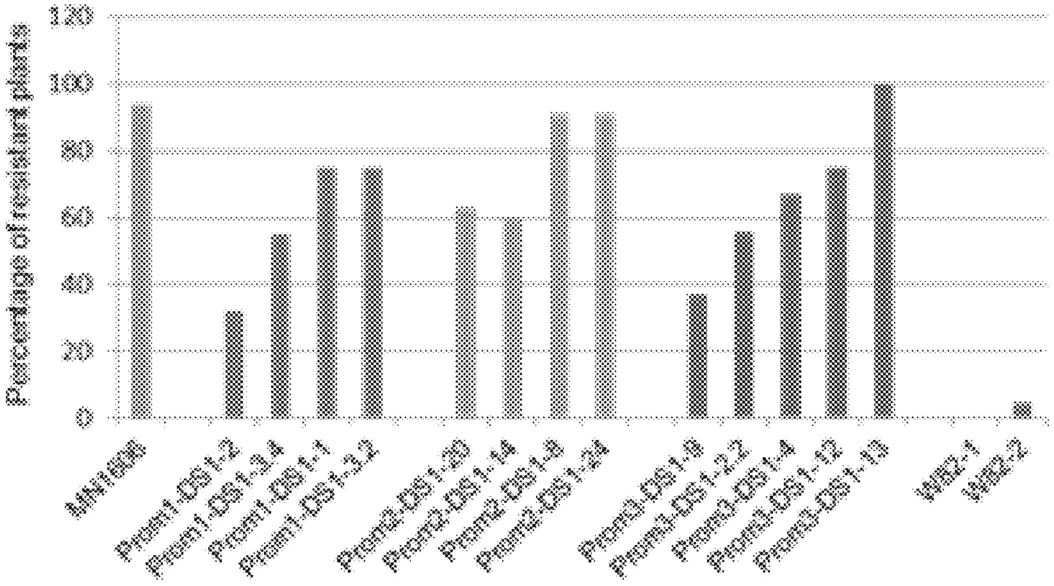
Figure 9D:
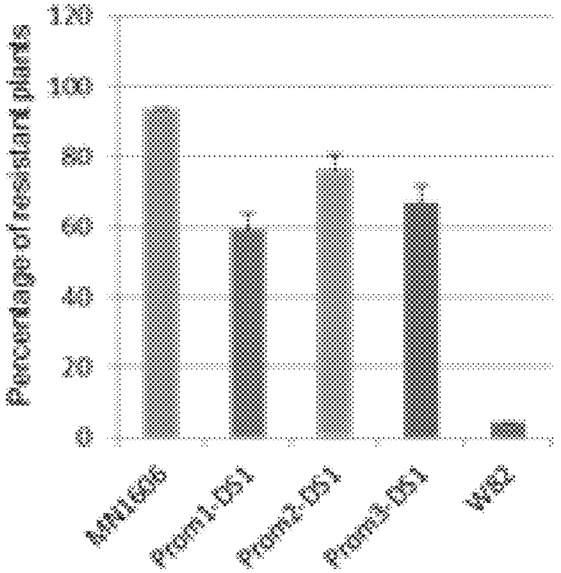

FIGS. 9A-9D show the expression of GmDS1 (SEQ ID NO: 5) enhanced SDS resistance in transgenic soybean plants in a field trial. $R_1$ plants were tested for resistance to *F. virguliforme* under field conditions in the summer of 2015 (June to October). FIG. 9A shows SDS resistant phenotype of GmDS1 transgenic soybean plants. FIG. 9B shows SDS susceptible phenotype of Williams 82. Pictures were taken on October 7 (last day of scoring) while the plants were at maturity stage (R-stage) 6.0. Prom2-DS1-8, an SDS resistant line of the Prom1-DS1-8 transgenic $R_0$ line. FIG. 9C shows the percentage of *F. virguliforme* resistant $R_1$ progenies from each $R_0$ transformants. All thirteen transgenic lines of GmDS1 showed more than 25 to 100% of plants resistant to *F. virguliforme* with no symptoms to slight yellowing with disease scores 0 and 1. The rest showed severe disease symptoms with interveinal to severe chlorosis and necrosis with disease scores 2 to 7. FIG. 9D shows the percentage of $R_1$ plants from individual GmDS1 transgenes resistant to *F. virguliforme*. Each bar represents mean and standard error of $R_1$ progenies of individual GmDS1 transgene. Three transgenes were generated by fusing three infection inducible promoters to GmDS1 (SEQ ID NO: 5).

Figure 10A:
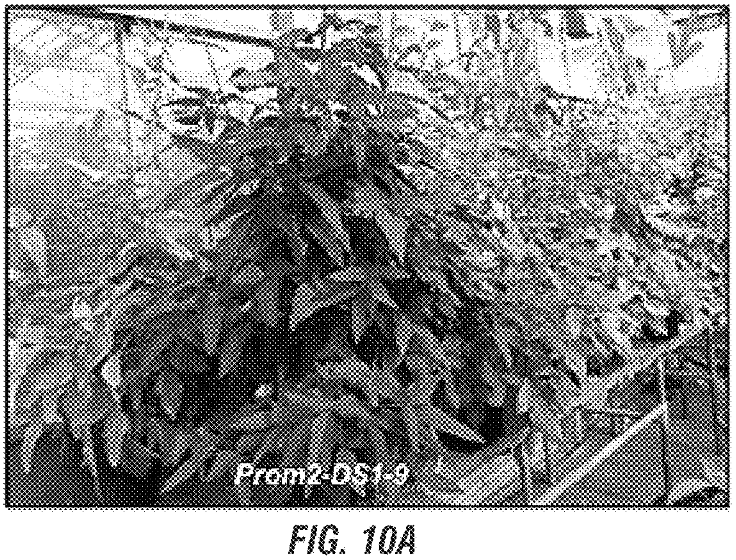
Figure 10B:
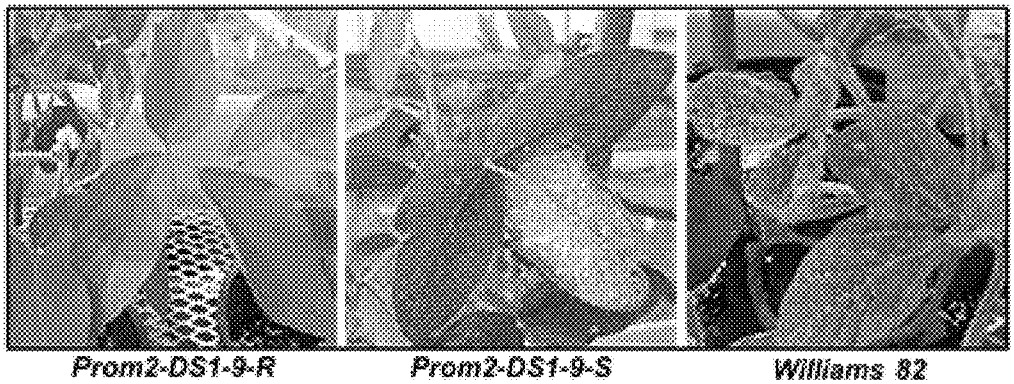
Figure 10C:
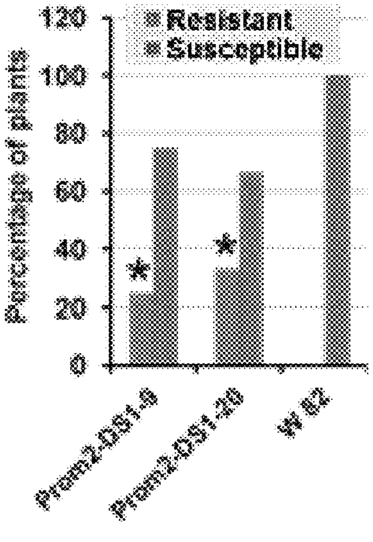

FIGS. 10A-10C show the expression of GmDS1 (SEQ ID NO: 5) conferred immunity against the spider mites. FIG. 10A shows $R_0$ transgenic soybean plant (red arrow) carrying Prom2-GmDS1 transgene showed resistance to spider mites. The pest infected heavily the rest of the transgenic plants with different transgenes. FIG. 10B shows representative images of five to nine $R_1$ progenies from each of two independent transformants were exposed to spider mites for two weeks. FIG. 10C is a graphical representation showing at least 25% of the segregating transgenic lines did not show any symptoms of spider mite infestation. * Significantly different to Williams 82.

Figure 11:
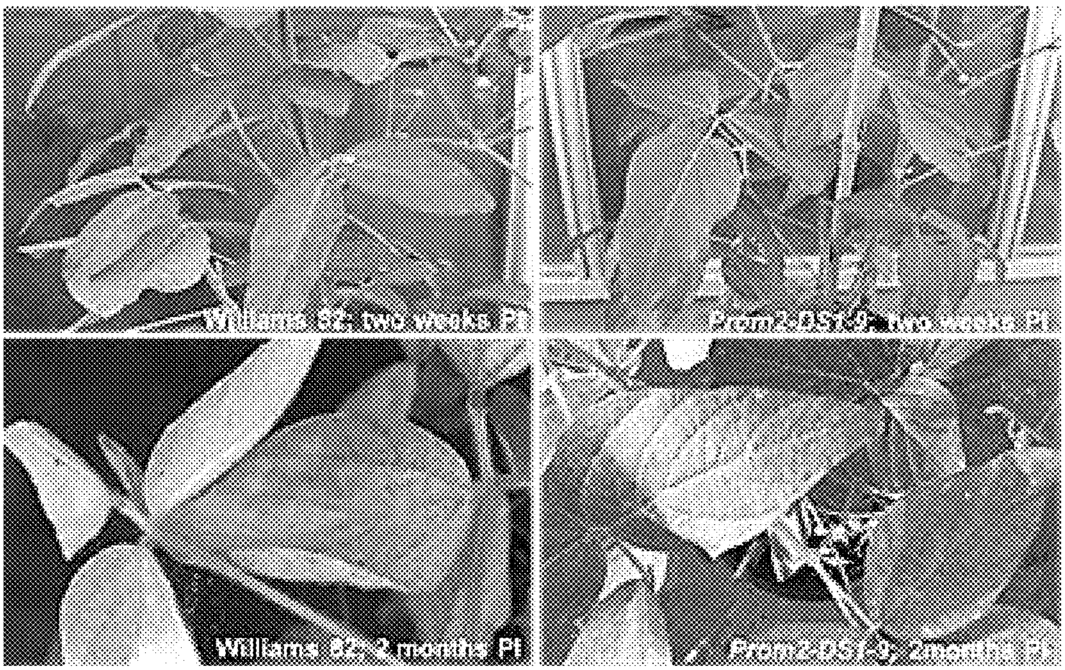

FIG. 11 shows the expression of GmDS1 (SEQ ID NO: 5) conferred immunity against the spider mites. Plants were infected with spider mites for two months. Pictures were taken 2 weeks and 2 months following inoculation with spider mites as shown on the photos.

Figures 12A, 12B:
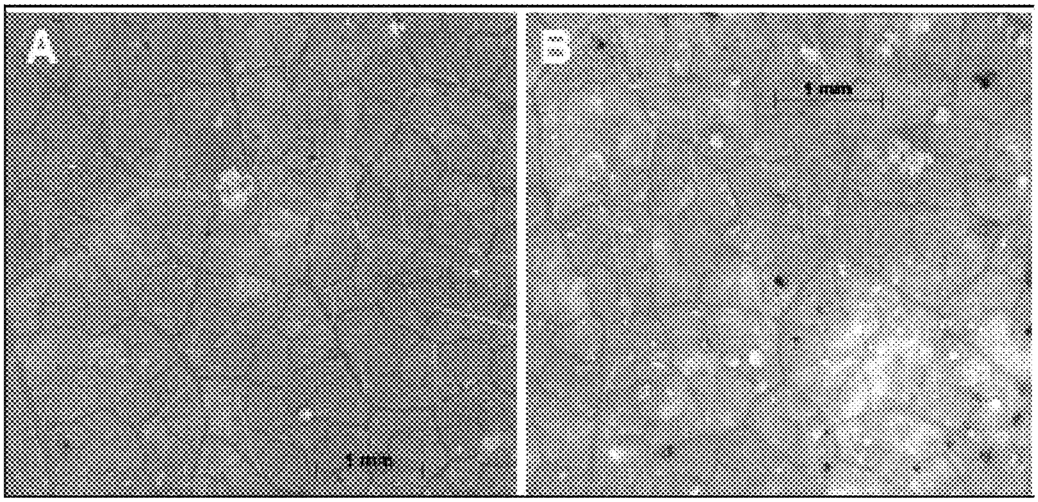
Figure 12C:
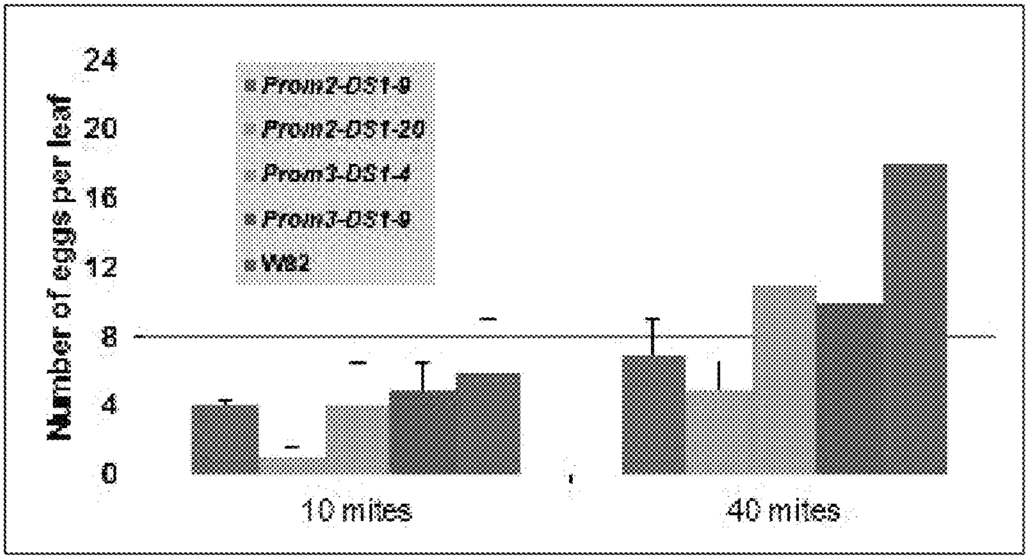

FIGS. 12A-12C show GmDS1 (SEQ ID NO: 5) conferred immunity against the spider mites. Four $R_1$ progenies of a spider mite resistant plant were evaluated under two levels of inoculum. FIG. 12A shows a spider mite resistant plant shows fewer eggs developed five day following inoculation. FIG. 12B shows spider mite susceptible nontransgenic Williams 82 cultivar showed many eggs and chlorosis of the leaf blade. FIG. 12C show egg numbers for individual $R_1$ progenies five days following inoculation with either 10 or 40 adult mites.

Figure 13A:
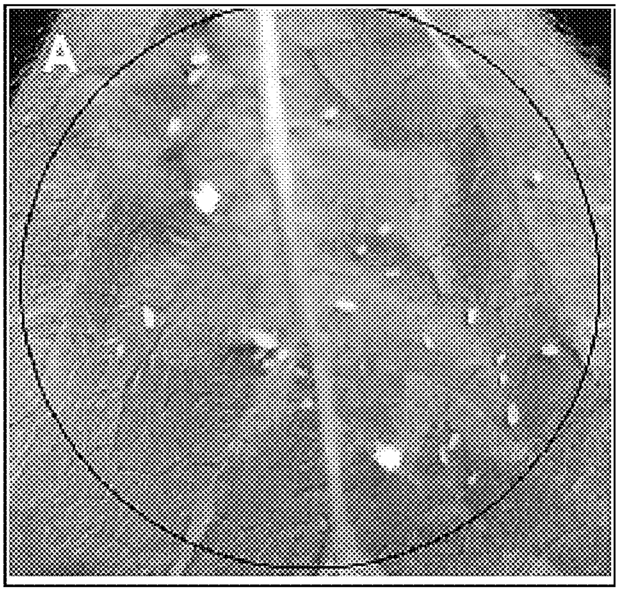
Figure 13B:
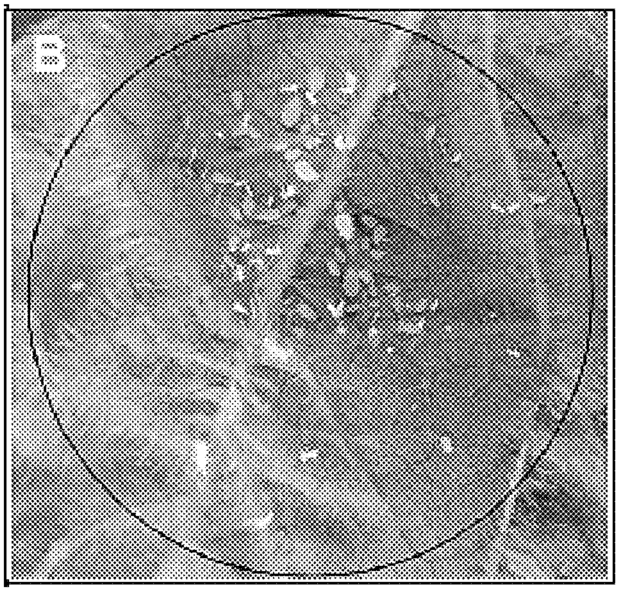
Figure 13C:
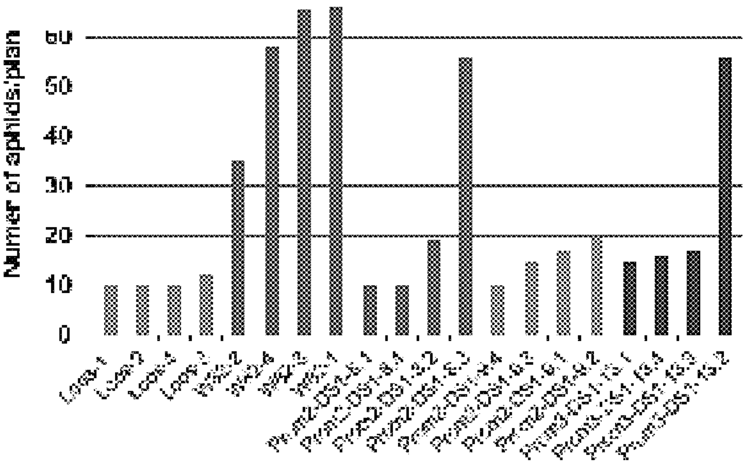
Figure 13D:
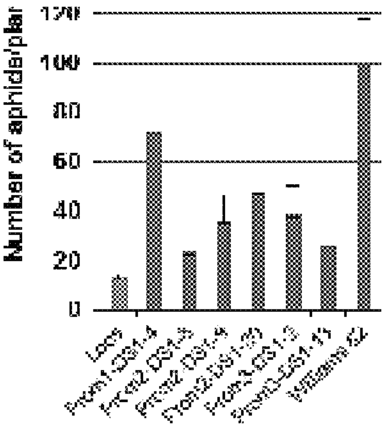

FIGS. 13A-13D show GmDS1 (SEQ ID NO: 5) transgenes provides resistance to soybean aphids. FIG. 13A shows a resistant line carrying GmDS1 (SEQ ID NO: 5) transgene showed fewer aphids generated from 10 aphids. FIG. 13B shows a large number of aphids multiplied from 10 aphids in the nontransgenic Williams 82 cultivar. FIG. 13C shows a number of aphids for each line used (four plants for each). FIG. 13D shows the average number of aphids expressed as % of aphids in the susceptible Williams 82 control. 'Loose' is a soybean aphid resistant soybean line. n=4, biological replicates for each genotype.

Figure 14A:
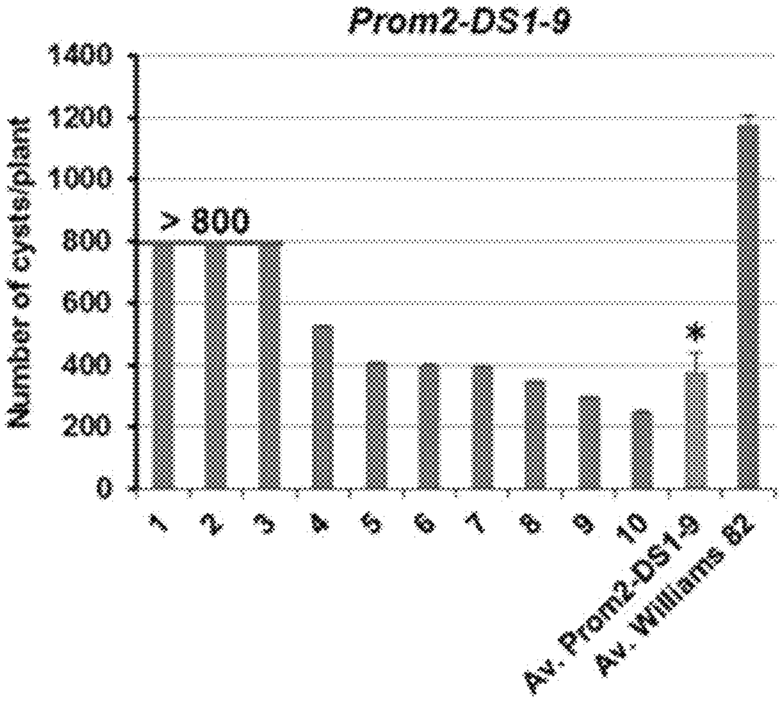
Figure 14B:
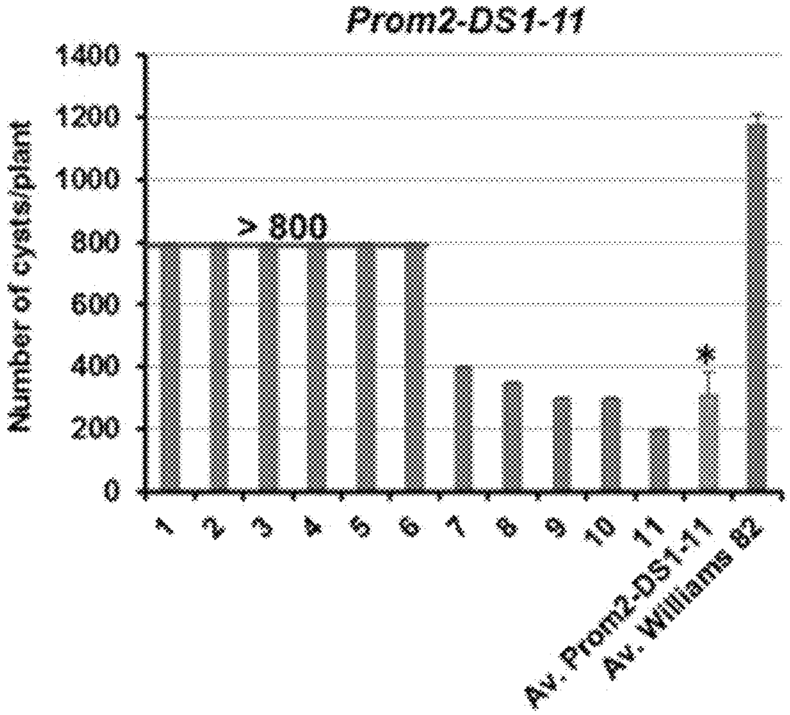

FIGS. 14A-14B show a reduction in the number of female cysts on roots of $R_1$ progenies segregating for the Prom2-GmDS1 fusion transgene. SCN cysts were counted up to 800 for $R_1$ segregants. We counted cyst completely only in Williams 82 plants, which shown to have an average of ~1,200 cyst/plant. FIG. 14A shows the progenies of Prom2-DS1-9 transformant showed segregation for SCN resistance and susceptibility. Seven plants (70%) showed partial SCN resistance with reduced numbers of female cysts, averaging 377 cysts/plant (green bar), as compared to the nontransgenic control, Williams 82 (~1,200 cysts/plant, red bar); 3 plants (30%) carried >800 female cysts per plant and are SCN susceptible. FIG. 14B shows the progenies of Prom2-DS1-11 transformant segregated for SCN resistance and susceptibility. Five plants out of eleven (45%) shown to carry reduced number of cysts, averaging 310 cysts/plant (green bar). A95-684043 is a SCN resistant soybean cultivar, with <200 cysts/plant (bar diagram not shown). The difference is statistically significant at $p \leq 0.01$ when compared to the number SCN cysts in Williams 82.

Figure 15A:
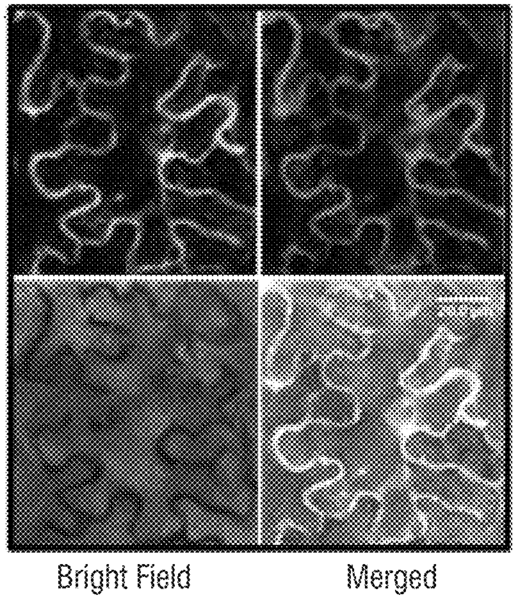
Figure 15B:
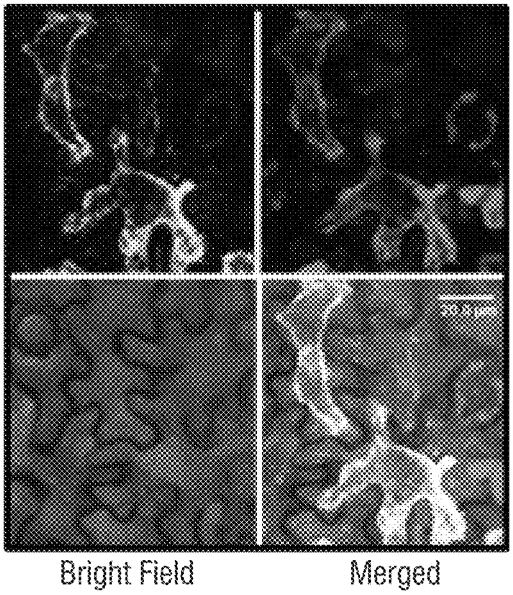

FIGS. 15A-15B show GmDS1 (SEQ ID NO: 6) is a plasma membrane protein. GFP tagged GmDS1 and RFP tagged plasma membrane marker co-localized at the plasma membrane. Confocal microscopy of tobacco leaf epidermis transiently expressing GmDS1-GFP together with RFP tagged plasma membrane marker (PM-m-cherry) 72 h after transient expression using *Agrobacterium tumefaciens*. FIG. 15A show leaf tissue treated with water; FIG. 15B show leaf tissue treated with 5M NaCl. Separate images of GmDS1-GFP (green fluorescence) and PM-m-cherry (red fluorescence) were merged. Note the peripheral distribution of the green and red fluorescence suggesting co-localization of the two transiently expressed proteins in plasma membrane.

Figure 16A:
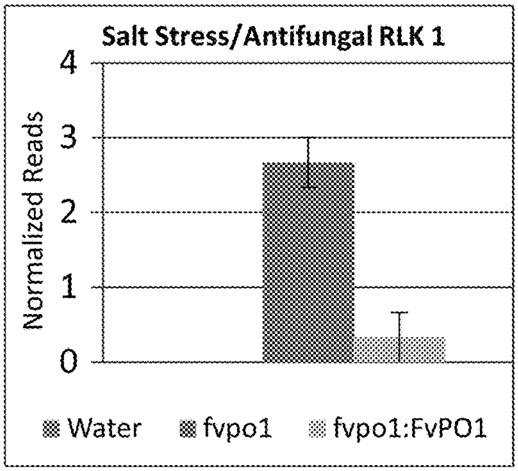
Figure 16B:
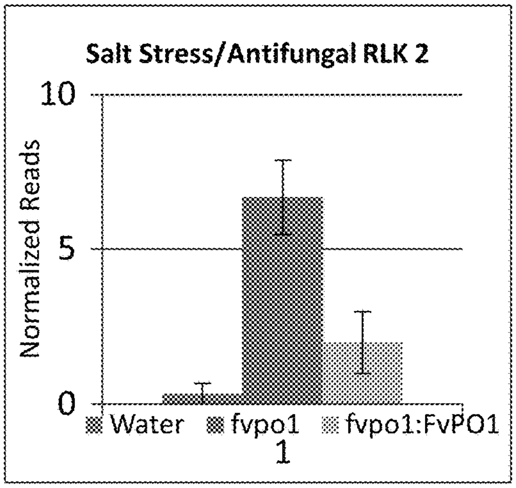
Figure 16C:
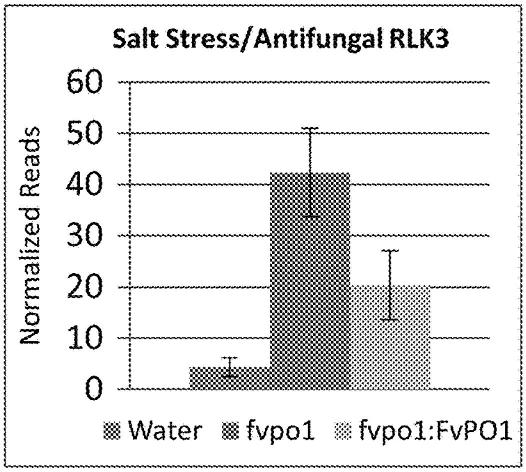
Figure 16D:
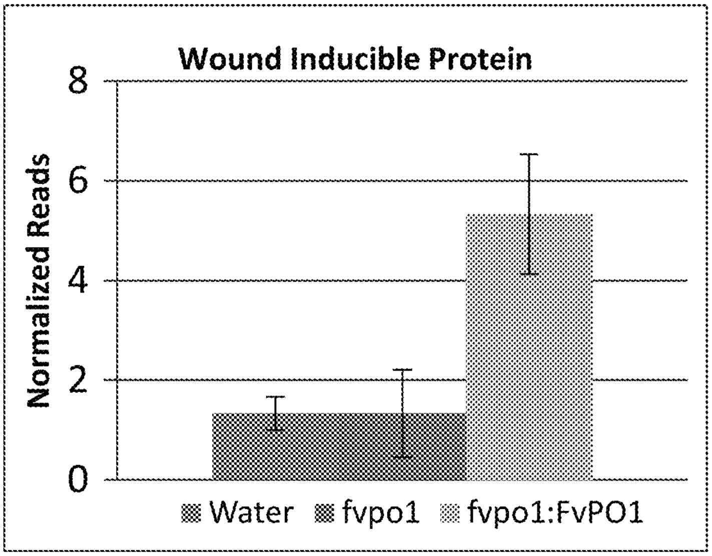
Figure 16E:
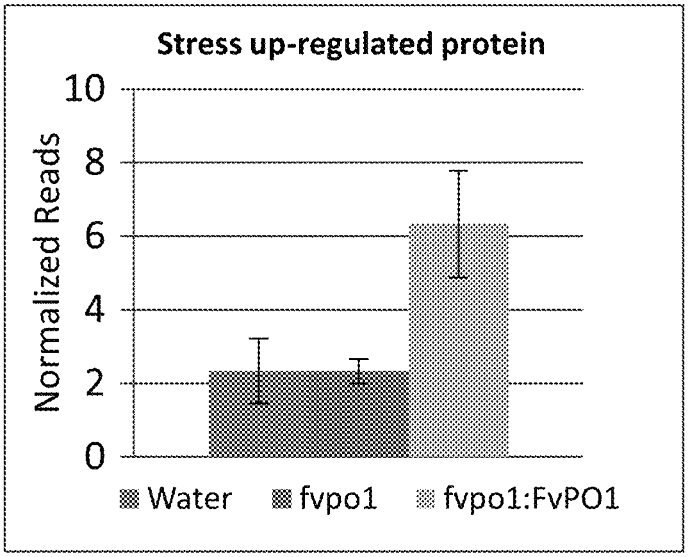

FIG. 16A-16E show soybean gene expression changes found with fvpo1 mutant and fvpo1:FvPO1 (complemented fvpo1 mutant with FvPO1 (SEQ ID NO: 9)) infection. FIG. 16A, FIG. 16B, and FIG. 16C show increased expression of salt stress/antifungal receptor like kinases (FIG. 16A, Glyma.10G253600; FIG. 16B, Glyma.20G139200; FIG. 16C, Glyma.19G005700) in the fvpo1 mutants with only a slight increase in the fvpo1:FvPO1 complemented fungal infection. FIG. 16D, and FIG. 16E show increased expression of possible hydrogen peroxide induced genes (FIG. 16D, Glyma.06G297600; FIG. 16E, Glyma.05G126900) in the complemented fvpo1:FvPO1 fungal infection but not in the fvpo1 mutant.

Figure 17:
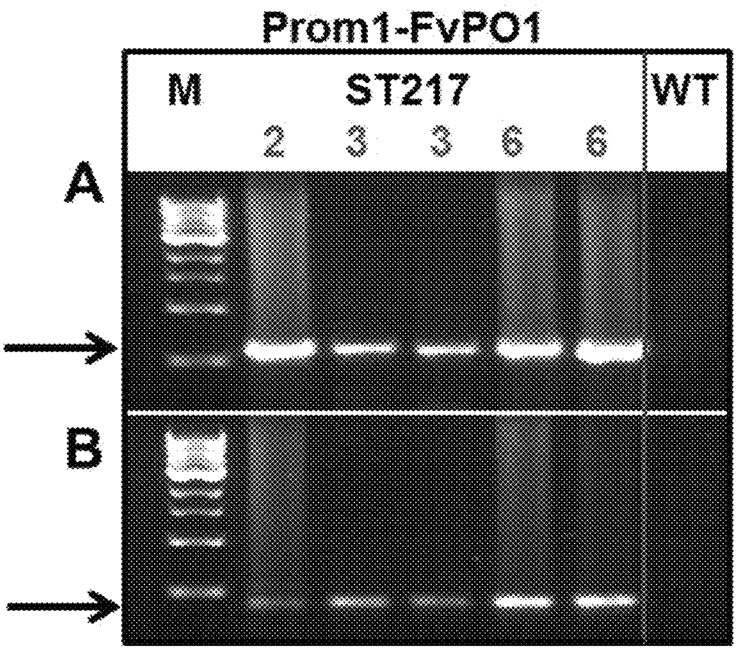

FIG. 17. Analyses of three soybean transformants carrying Prom1-FvPO1 fusion gene. PCR amplification of the Prom1:FvPO1 transgene in three separate soybean transformants Prom1:FvPO1-2 (2), Prom1:FvPO1-3 (3) and Prom1:FvPO1-6 (6). A. Amplification of the FvPO1 (SEQ ID NO: 9) gene using a gene specific primer and a vector specific primer is visible in all the transformants but not in the Williams 82 background (WT). B. Amplification of the bar resistance gene is present in each of the transformants and not present in the non-transgenic soybean cultivar Williams 82 (WT).

Figure 18A:
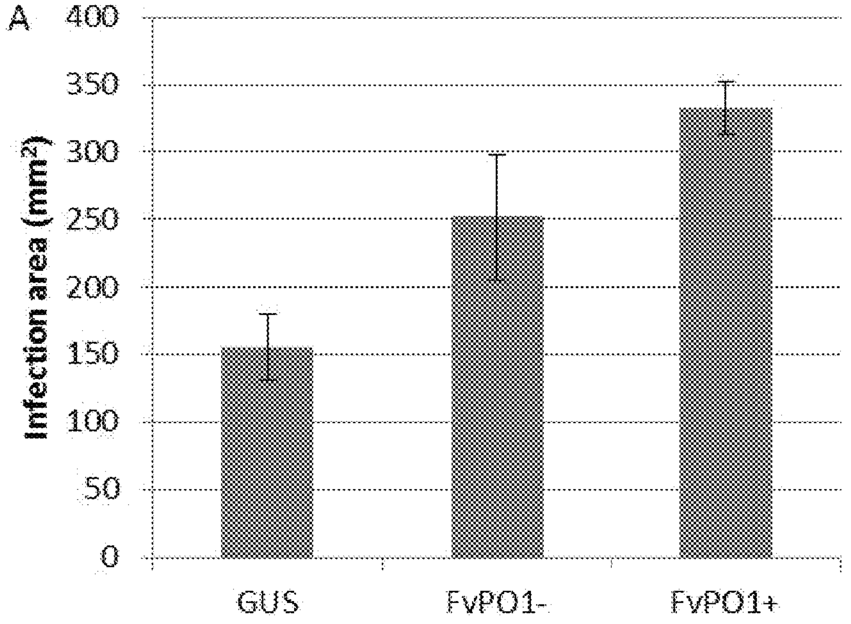
Figure 18B:
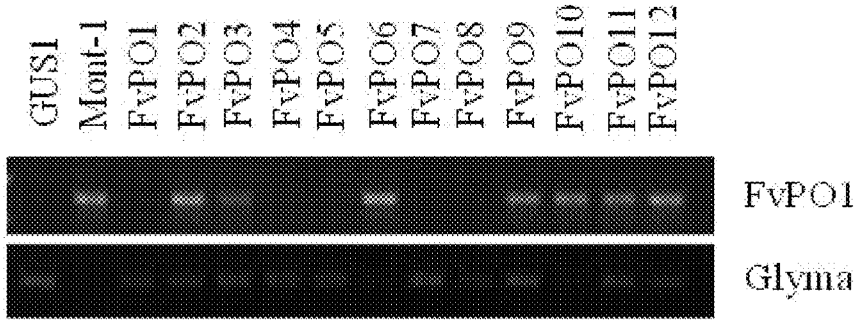
Figure 18C:
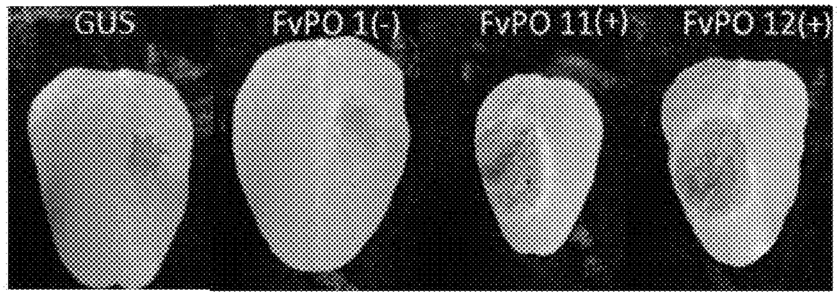

FIG. 18A-18C. Increased susceptibility in transgenic soybean plants carrying FvPO1 (SEQ ID NO: 9). Leaves from twelve R1 plants carrying Prom1:FvPO1 transgene, and eight transgenic plants carrying the GUS gene, were wounded and inoculated with a spore suspension (1×107 spores/ml) of *F. virguliforme* Mont-1 isolate.

FIG. 18A shows lesion sizes soybean leaves following *F. virguliforme* infection. The length and width of the infection area were measured and the average infection area was calculated; GUS, negative control; FvPO1−, progenies with no FvPO1 transgene (PCR negative); FvPO1+, PCR positive progenies, carry FvPO1. Error bars show standard error of the mean.

FIG. 18B shows molecular analyses of transgenic plants. PCR results from GUS transgenic plants, Mont-1 strain *F. virguliforme*, and the 12 progenies of a Prom1:FvPO1 transformant. FvPO1 primers amplify a region of the FvPO1 (SEQ ID NO: 9) gene. Amplification in Mont-1 is a positive control for FvPO1 amplification. FvPO1 was amplified in seven of the Prom1:FvPO1 progeny. Soybean gene Glyma14g38210 (Glyma) was used as a positive control for soybean gene amplification and is present in all samples except for Mont-1.

FIG. 18C shows disease symptoms following *F. virguliforme* infection. Infection area of wounded leaves from Gus progeny (GUS1), FvPO1, did not carry the FvPO1 gene (−); FvPO11 and FvPO12 did carry the FvPO1 gene (+). Infection area was calculated using the formula for the area of an oval (W×L×0.8).

Figure 19A:
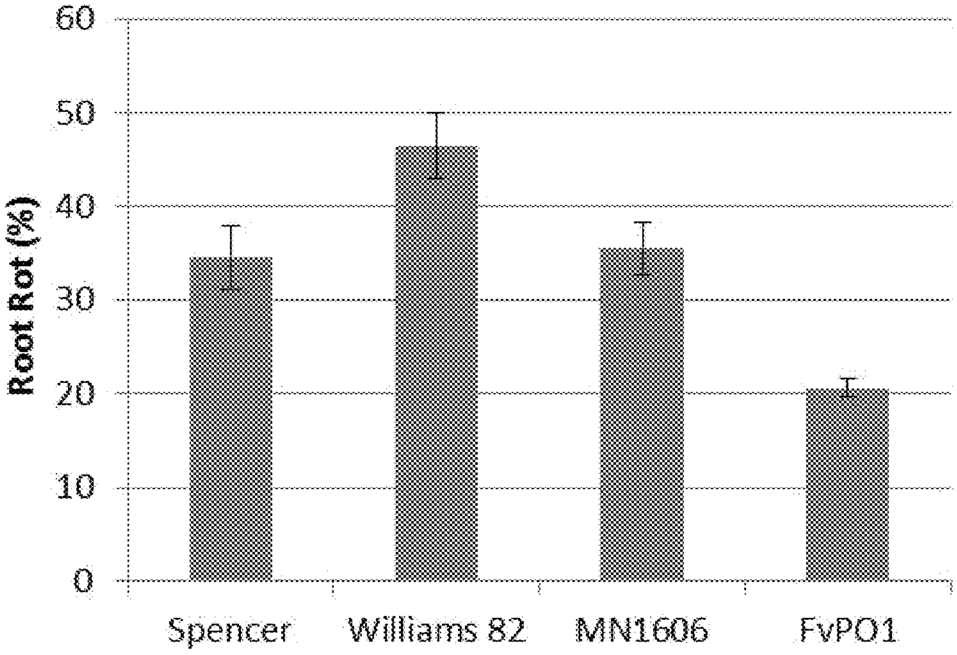
Figure 19B:
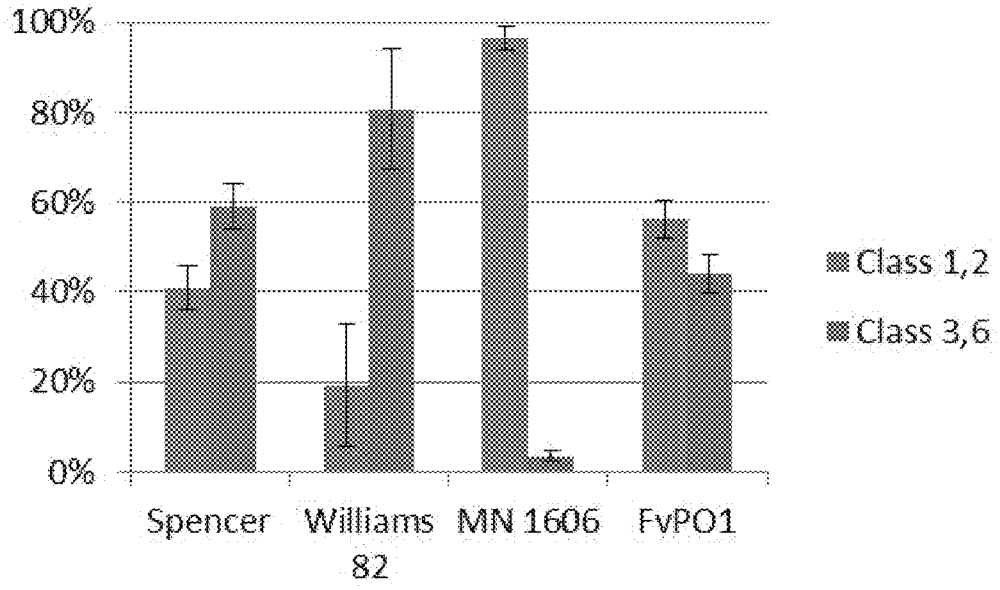

FIG. 19A-19B. Transgenic soybean plants carrying Prom1:FvPO1 showed increased root resistance to *F. virguliforme* infection. Seeds were inoculated with *F. virguliforme* infested sorghum grain mixed in a 1:20 ratio with a 1:1 sand:soil mixture.

FIG. 19A shows roots were harvested and washed, then scored for the percentages of roots showing root rot symptoms. Error bars show the standard error of the mean among 10 plants.

FIG. 19B shows percentages of plants falling into two classes of foliar SDS symptoms. Symptoms scored after four weeks. Williams 82 and Spencer are susceptible soybean lines; MN1606 is the existing resistant soybean line. Class 1-2, no symptoms to slight yellowing; class 3-6, interveinal to severe chlorosis and necrosis. Error bars show he standard error of the mean between two trials. The line is most likely segregating for FvPO1 (SEQ ID NO: 9) gene.

Note that the symptoms were reduced when compared with the transformation background line Williams 82, but comparable to the known susceptible line Spencer.

FIG. 20 shows the promoters (Prom 1 (SEQ ID NO: 11), Prom 2 (SEQ ID NO: 12), and Prom 3 (SEQ ID NO: 13)) used in the constructs.

DETAILED DESCRIPTION OF THE INVENTION

The present invention provides, inter alia, compositions and methods for promoting broad-spectrum pathogen resistance in plants, more particularly for improving *Fusarium* resistance of susceptible plants. The compositions of the invention relate to the identification of *Fusarium* resistance genes identified from *Glycine max* and *Fusarium virguliforme* which are associated with *Fusarium sojae* resistance. Thus, these genes may be used to confer or improve resistance in susceptible plant species such as soybean. Thus, the genes and proteins identified here may be introduced or modulated to confer improved *Fusarium* resistance in plants. These genes, nucleic acid sequences or proteins can be transferred into plants to confer or improve *Fusarium* resistance, can be modified to engineer gene sequences or amino acid sequences for broad based resistance in plants, or can be used to isolate and identify alternate gene forms and markers which may be used in breeding regimes. By "confer or improve *Fusarium* or other such pathogen resistance" is intended that the proteins or sequences, either alone or in combination with other proteins or sequences, enhance resistance of a plant to *Fusarium* and *Fusarium*-caused damage, or to other pathogens which cause a similar plant reaction. In this manner, resistance to these fungal pathogens and other pathogens such as *Pseudomonas syringae* pv. *glycinea* (Psg), soybean cyst nematode (SCN), soybean aphid, soybean spider mite, or soybean mosaic virus (SMV), *Fusarium virguliforme* can be enhanced or improved in the transformed plant or its progeny when at least one of the sequences of the invention is introduced to a susceptible plant or otherwise modulated according to the invention.

The compositions include nucleic acid molecules comprising sequences of plant genes and the polypeptides encoded thereby which are associated with resistance against *Fusarium* have been identified. Particularly, the nucleotide and amino acid sequences Glyma01g37680.1 (salicylic acid methyl transferases) (SEQ ID NOS: 1 and 2), Glyma12g12470.1 (ankyrin repeat-containing protein) (SEQ ID NOS: 3 and 4), Glyma10g12400.1 (unknown protein)(SEQ ID NOS 5 and 6), Glyma10g32980.1 (sieve element-occulsion protein) (SEQ ID NOS: 7 and 8) and an *F. virguliforme* gene FvPO1 (polyamine oxidase) (SEQ ID NOS: 9 and 10) and any conservatively modified variants, fragments, and homologs or full length sequences incorporating the same which retain the Phyphthora infection related activity described herein are part of the invention.

As discussed in more detail below, the sequences of the invention are presumably involved in many basic biochemical pathways that regulate plant pathogen resistance. Thus, methods are provided for the introduction or modulation of these sequences in a susceptible host plant to improve plant defense responses. Some of the methods involve stably transforming a plant with a nucleotide sequence of the invention operably linked with a promoter capable of driving expression of a gene in a plant cell. Other methods may involve inhibition of the same sequences to confer improved pathogen resistance in a particular plant.

Promoter and other regulatory elements which are natively associated with these genes can be easily isolated using the sequences and methods described herein with no more than routine experimentation. These sequences can also be used to identify promoter, enhancer or other signaling sequences in the regulatory regions of resistance genes. Such regulatory elements or promoters would provide for temporal and spatial expression of operably linked sequences with pathogen infection in a plant. Nucleotide sequences operably linked to such promoter sequences are transformed into a plant cell. Exposure of the transformed plant to a stimulus such as pathogen infection could induce transcriptional activation of the nucleotide sequences operably linked to these promoter regulatory sequences.

Transformed plants can be obtained having altered or enhanced responses to *Fusarium* attack; hence, the methods and compositions may find uses in altering the response of plants to similar stresses as well. Thus, the sequences of the invention find use in engineering broad-spectrum disease and pest resistance in a variety of plants. It is within the skill in the art to assay protein activities obtained from various sources to determine whether the properties of the proteins are the same. In so doing, one of skill in the art may employ any of a wide array of known assays including, for example, biochemical and/or pathological assays. For example, one of skill in the art could readily produce a plant transformed with a non-host resistance protein variant and assay a property of the native protein in that plant material to determine whether a particular property was retained by the variant.

The compositions and methods of the invention are presumably involved in biochemical pathways and as such may also find use in the activation or modulation of expression of other genes, including those involved in other aspects of pathogen defense and response.

By "modulating" or "modulation" is intended that the level of expression of a gene may be increased or decreased relative to genes driven by other promoters or relative to the normal or uninduced level of the gene in question.

The present invention provides for isolated nucleic acid molecules comprising nucleotide sequences encoding the amino acid sequence herein: Glyma01g37680.1 (salicylic acid methyl transferases) (SEQ ID NOS: 1 and 2), Glyma12g12470.1 (ankyrin repeat-containing protein) (SEQ ID NOS: 3 and 4), Glyma10g12400.1 (unknown protein) (SEQ ID NOS 5 and 6), Glyma10g32980.1 (sieve element-occulsion protein) (SEQ ID NOS: 7 and 8) and an *F. virguliforme* gene FvPO1 (polyamine oxidase) (SEQ ID NOS: 9 and 10) and any conservatively modified variants, fragments, and homologs or full length sequences incorporating the same which retain the Phyphthora infection related activity described herein. Further provided are polypeptides having an amino acid sequence encoded by a nucleic acid molecule described herein, for example those polypeptides comprising the sequences set forth in the herein, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20 or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, stress responses, and/or disease resistance by retaining non-host resistance-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a non-host resistance nucleotide sequence that encodes a biologically active portion of a non-host resistance protein of the invention will encode at least 12, 25, 30, 50, 75, etc. contiguous amino acids, or up to the total number of amino acids present in a full-length non-host resistance protein of the invention.

Fragments of a non-host resistance nucleotide sequence that are useful as hybridization probes or PCR primers generally may or may not encode a biologically active portion of a protein. Thus, a fragment of a non-host resistance protein nucleotide sequence may encode a biologically active portion of a non-host resistance protein, or it may be used as a hybridization probe or PCR primer using methods disclosed below. A biologically active portion of a non-host resistance protein can be prepared by isolating a portion of the non-host resistance nucleotide sequences of the invention, expressing the encoded portion of the non-host resistance protein (e.g., by recombinant expression in vitro), and assessing the activity of the encoded portion of the non-host resistance protein. Nucleic acid molecules that are fragments of a non-host resistance nucleotide sequence comprise at least 16, 20, 25, 30, 40, 50, 60, 70, 80, 90, 100, 125, 150, 175, 200, etc. nucleotides, or up to the number of nucleotides present in a full-length non-host resistance nucleotide sequences disclosed herein.

The proteins of the invention may be altered in various ways including amino acid substitutions, deletions, truncations, and insertions. Methods for such manipulations are generally known in the art. For example, amino acid sequence variants of the non-host resistance proteins can be prepared by mutations in the DNA. Methods for mutagenesis and nucleotide sequence alterations are well known in the art. See, for example, Kunkel (1985) *Proc. Nat. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

It is recognized that having identified the nucleotide sequences disclosed herein, it is within the state of the art to isolate and identify regulatory elements in the 5' untranslated region upstream from regions defined herein. Thus, for example, the promoter regions of the gene sequences disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618. It is also recognized by those of skill in the art that regulatory elements may be found in transcribed regions of a gene, for example in the region between transcription start and translation start as well as 3' to the end of translation; such elements may be found in the sequences set forth herein.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have *Fusarium* resistance-like activity or and which hybridize under stringent conditions to the *Fusarium* resistance sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present it a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire sequence disclosed herein, or one or more portions thereof, may be used as a probe capable of specifically hybridizing to corresponding *Fusarium*-response sequences, including promoters and messenger RNAs. To achieve specific hybridization under a variety of conditions, such probes include sequences that are unique among *Fusarium*-response sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Assays that measure antipathogenic activity induced by the signal pathway from the sequences herein are commonly known in the art, as are methods to quantitate disease resistance in plants following pathogen infection. See, for example, U.S. Pat. No. 5,614,395, herein incorporated by reference. These assays may be used to measure the activity of the polypeptides of the invention. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic proteins to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) 1 *Biol. Chem.* 267: 2228-2233, both of which are herein incorporated by reference).

Pathogens of the invention include, but are not limited to, fungal and viral pathogens for primarily soybeans which include: *Fusarium sojae, Macrophomina phaseolina, Rhizoctonia solani, Sclerotinia sclerotiorum, Fusarium virguliformae,* (*Fusarium solani*) *Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassfcola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Phakopsora meibomiae, Pythium aphanidermatum, Pythium ultimum, Pythium debaryanum*, Tomato spotted wilt virus, *Heterodera glycines.*

It is understood in the art that plant DNA viruses and fungal pathogens remodel the control of the host replication and gene expression machinery to accomplish their own replication and effective infection. The plant response to stress, such as stress caused by *Fusarium* attack, is known to involve many basic biochemical pathways and cellular functions. Hence, the sequences of the invention may find use in altering the defense mechanisms of a host plant to provide broad-based resistance to disease or insect pests. Additionally, the present invention may be useful in preventing corruption of the cell machinery by viruses and other plant pathogens.

The compositions and methods of the invention function to inhibit or prevent plant diseases. The gene products may accomplish their anti-pathogenic effects by suppressing, controlling, and/or killing the invading pathogenic organism in non-host plants and these sequences may then be used to engineer resistance in susceptible plants.

The cells that have been transformed may be grown into plants in accordance with conventional ways. See, for example, McCormick et al. (1986) *Plant Cell Reports* 5:8184. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The invention in one aspect comprises expression constructs comprising a DNA sequence which encodes upon expression a non-host resistance nucleic acid sequence operably linked to a promoter to direct expression of the protein. These constructs are then introduced into plant cells using standard molecular biology techniques. The invention can be also be used for hybrid plant or seed production, once transgenic inbred parental lines have been established.

The methods of the invention described herein may be applicable to any species of plant.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also, as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example, one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly, the Lipoxegenase ("the LOX gene") is a fruit specific promoter.

Other fruit specific promoters are the 1.45 promoter fragment disclosed in Bird, et al., *Plant Mol. Bio.*, pp 651-663(1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the CamV 35S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol.*, April 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in *Drosophila", Proc. Natl. Acad. Sci. USA,* 84, 9123-9127). This method was first developed in *Drosophila* and rapidly adapted to mice and plants (Wilson, C., Pearson, R. K., Bellen, H. J., O'Kane, Grossniklaus, U., and Gehring, W. J. (1989), "P-element-mediated enhancer detection: an efficient method for isolating and characterizing developmentally regulated genes in *Drosophila", Genes & Dev.,* 3, 1301-1313; Skarnes, W. C. (1990), "Entrapment vectors: a new tool for mammalian genetics", *Biotechnology,* 8, 827-831; Topping, J. F., Wei, W., and Lindsey, K. (1991), "Functional tagging of regulatory elements in the plant genome", *Development,* 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.,* 9, 1797-1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of *D. melanogaster* (Freeling, M., Bennet, D. C., Maize ADN 1*, Ann. Rev. of Genetics,* 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the feronia regulatory genes or with any other coding or transcribed sequence that is critical to pollin tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and $R_1$ plasmids of *A. tumefaciens* and *A. rhizogenes*, respectively, carry genes responsible for genetic transformation of the plant. See, for example, Kado, C. I., *Crit. Rev. Plant. Sci.* 10: 1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 □m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.,* 4: 2731 (1985), Christou et al., *Proc Natl. Acad. Sci. U.S.A.* 84: 3962 (1987). Direct uptake of DNA into protoplasts using $CaCl_2$ precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species, this is accomplished rather easily by the use of another culture or isolated microspore culture. This is especially true for the oil seed crop *Brassica napus* (Keller and Armstrong, Z. flanzenzucht 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

Molecular Markers

The present invention provides a method of genotyping a plant comprising a heterologous polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Clark, Ed., Plant Molecular Biology: A Laboratory Manual. Berlin, Springer Verlag, 1997. Chapter 7. For molecular marker methods, see generally, "The DNA Revolution" in: Paterson, A. H., Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e. g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term “restriction enzyme” includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e. g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5'non-coding or untranslated region (5'UTR) of the RNA. Positive sequence motifs include translational initiation consensus sequences (Kozak, Nucleic Acids Res. 15: 8125 (1987)) and the 7-methylguanosine cap structure (Drummond et al., Nucleic Acids Res. 13: 7375 (1985)). Negative elements include stable intramolecular 5'UTR stem-loop structures (Muesing et al., Cell 48: 691 (1987)) and AUG sequences or short open reading frames preceded by an appropriate AUG in the 5'UTR (Kozak, supra, Rao et al., Mol. and Cell. Biol. 8: 284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as “Codon Preference” available from the University of Wisconsin Genetics Computer Group (see Devereaux et al., Nucleic Acids Res. 12: 387-395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. Proc. Natl. Acad. Sci. USA 94: 4504-4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms.

Alternatively, a polynucleotide having a consensus sequence generated from orthologous genes can be used to identify or isolate orthologs of other taxa. Typically, a polynucleotide having a consensus sequence will be at least 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P (N)). Various suppliers of sequence-analysis software are listed in chapter 7 of Current Protocols in Molecular Biology, F. M. Ausubel et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Stacking

In certain embodiments, the nucleic acid sequences of the embodiments can be stacked with any combination of polynucleotide sequences of interest in order to create plants with a desired phenotype. This stacking may be accomplished by a combination of genes within the DNA construct, or by crossing a line containing the resistance genes of the invention (as transgenes or as an introgressed locus), with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for further insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield, and better agronomic quality. With mechanical harvesting of many crops, uniformity of plant characteristics such as germination and stand establishment, growth rate, maturity, and plant height is desirable. Traditional plant breeding is an important tool in developing new and improved commercial crops. This invention encompasses methods for producing a plant by crossing a first parent plant with a second parent plant wherein one or both of the parent plants is a transformed plant according to the invention displaying *Fusarium* resistance as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids, and transformation. Often combinations of these techniques are used.

The development of hybrids in a plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross, or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform; and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

Development of Novel Soybean Germplasm for Improving Soybean for SDS Resistance In this project, we choose to express several soybean and *F. virguliforme* genes in transgenic soybean plants to determine if expression of any of these genes enhances resistance to the SDS pathogen. The genes were selected based on their possible role in disease resistance. Following infection of soybean with the SDS pathogen *F. virguliforme*, the selected genes are rapidly silenced. Presumably pathogen silenced the expression of these candidate defense genes so that it can infect soybean. We proposed to alter the promoters of four selected soybean genes so that they will be induced during infection and confer resistance against the SDS pathogen. In addition, we also considered expressing a *F. virguliforme* gene to determine if it plays any role in the expression SDS resistance. We proposed to conduct following three objectives to accomplish the goal of this project.

1) Express at least one member from each of the four classes of candidate regulatory genes in soybean roots and during *Fusarium virguliforme* infection to enhance SDS resistance in transgenic soybean plants.

2) Generate transgenic soybean lines with the *F. virguliforme* polyamine oxidase gene, FvPO1 (SEQ ID NO: 9), for enhancing SDS resistance.

3) Introgress suitable genes that enhance SDS resistance in transgenic soybean plants into elite soybean lines.

We selected four soybean genes: (i) Glyma01g37680.1 (SAMT1, SEQ ID NOs: 1 and 16) encoding salicylic acid methyl transferases (SEQ ID NO: 2), (ii) Glyma12g12470.1 (New name: Glyma.12g111500) (ARP1, SEQ ID NO: 3 and 15) encoding an ankyrin repeat-containing protein (SEQ ID NO: 4), (iii) Glyma10g12400.1 (DS1, SEQ ID NO: 5 and 17) encoding an unknown protein (SEQ ID NO: 6), and (iv) Glyma10g32980.1 (SEO, SEQ ID NO: 7 and 18) encoding a sieve element-occlusion protein (SEQ ID NO: 8), and a *F. virguliforme* gene, FvPO1 (SEQ ID NO: 9), encoding a polyamine oxidase for this study. The expression of the selected soybean genes is suppressed in *F. virguliforme*-infected tissues. We have used three *F. virguliforme*-inducible promoters to induce the expression of the four soybean genes in *F. virguliforme*-infected tissues. Two of these infection-inducible promoters are also root-specific, one of which is highly active in roots. Twelve fusion soybean genes were generated by fusing the four soybean genes individually to the three selected promoters. Transgenic soybean plants are generated for these fusion genes along with a fusion gene for FvPO1. Several transgenic soybean plants were generated for these 13 transgenes and status of the project is presented in Table 1. Transgenic soybean plants carrying four soybean genes and the FvPO1 gene showed enhanced SDS resistance as compared to the non-transgenic recipient cultivar, Williams 82.

We have also investigated the possibility of enhancing SDS resistance in transgenic soybean plants by expressing a *F. virguliforme* gene that can produce defense molecules.

Removal of this gene from the pathogen makes the pathogen more virulent to soybean. Presumably, somehow soybean uses the enzyme encoded by this gene to produce toxic hydrogen peroxide, a defense compound. We created a fusion gene by fusing an infection inducible soybean promoter to this pathogen gene and created three transgenic soybean plants. Progenies of one of these three lines were analyzed. We have observed that in leaves, the gene induces susceptibility; whereas, in roots it confers enhanced SDS resistance against this pathogen. We will continue to characterize progenies of the other two transgenic soybean plants to determine possible utility of this pathogen gene in enhancing SDS resistance in soybean.

Evaluation of Transgenic Soybean Lines Containing an Ankyrin Repeat-Containing Protein Gene, GmARP1 (Glyma.12g111500).

Figure 1A:
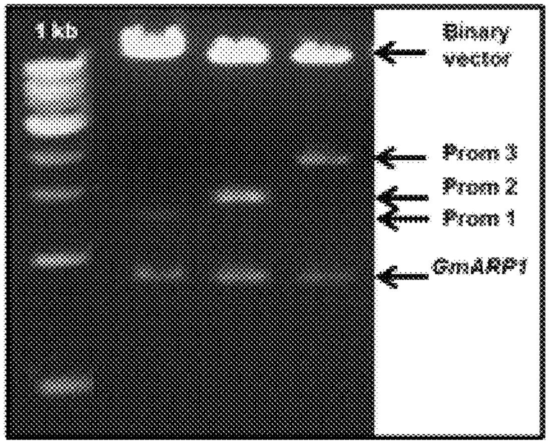
FIGS. 1A-1B show the generation of GmARP1 (SEQ ID NO: 3) transgenes and $R_0$ transgenic soybean plants.
Figure 1B:
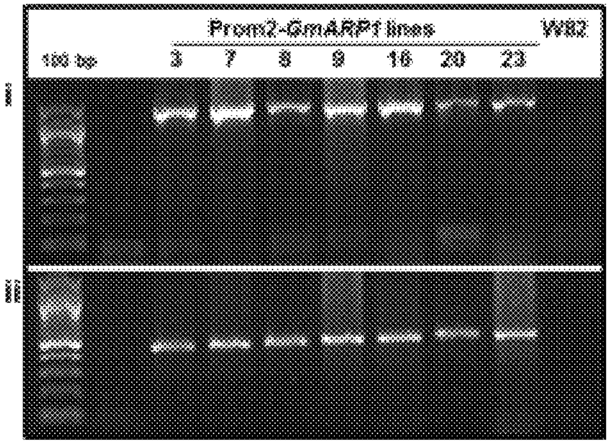

We used three *F. virguliforme*-inducible promoters to stimulate the expression of GmARP1 (SEQ ID NO: 3) during *F. virguliforme* infection (FIG. 1*a*). Putative transgenic plants carrying Prom1-GmARP1, Prom2-GmARP1 and Prom3-GmARP1 fusion genes were grown in Agronomy Greenhouse, Iowa State University (ISU). PCR analysis was conducted on DNA prepared from young leaves of these plants to determine the presence of GmARP1 fusion genes and the bar gene (selectable marker for soybean transformation) in these transformants (FIG. 1*b*).

Figure 2B:
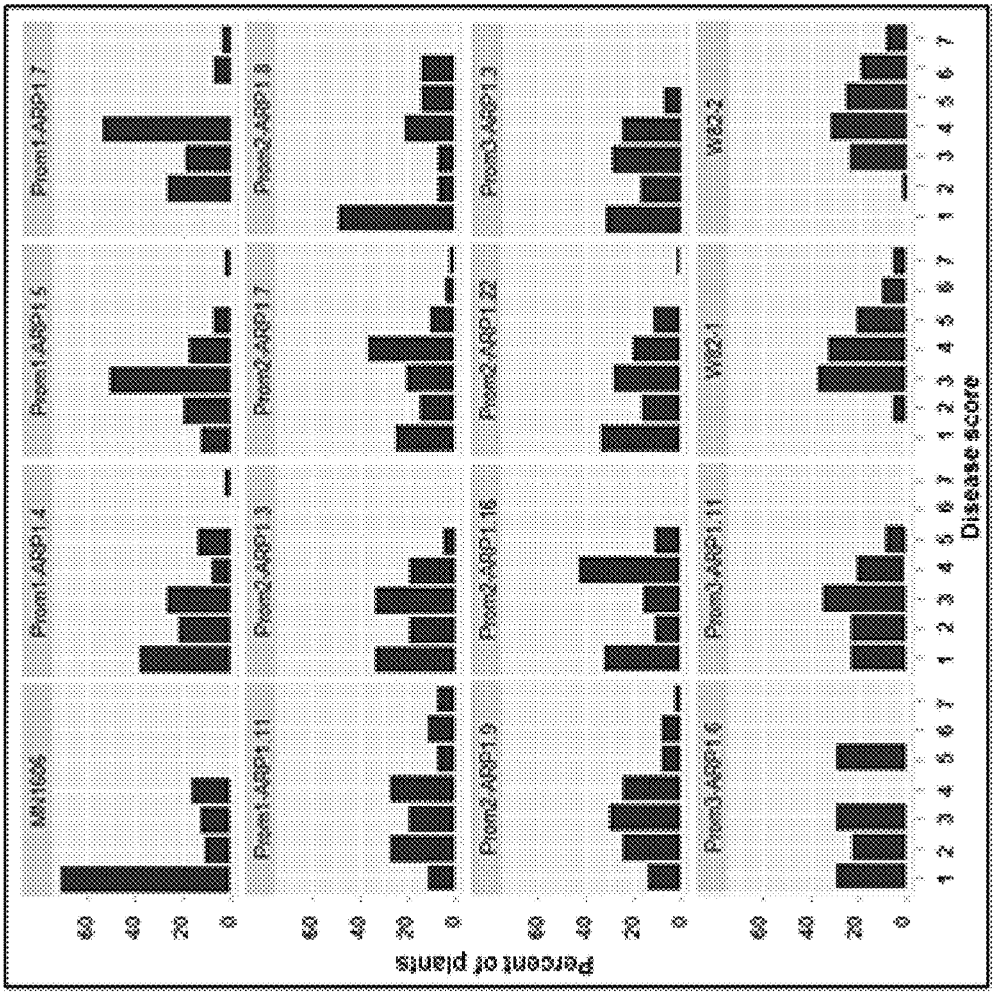
FIGS. 2A-2D show the expression of GmARP1 (SEQ ID NO: 3) enhanced SDS resistance in transgenic soybean plants.
Figure 2A:
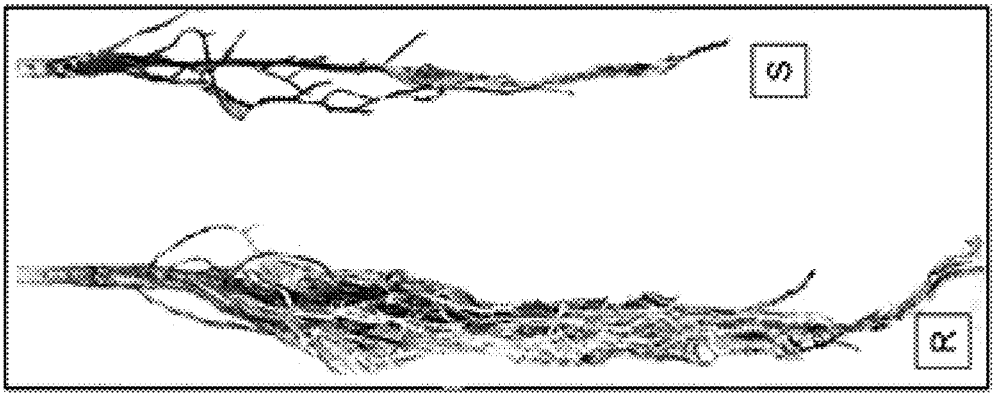
Figure 2C:
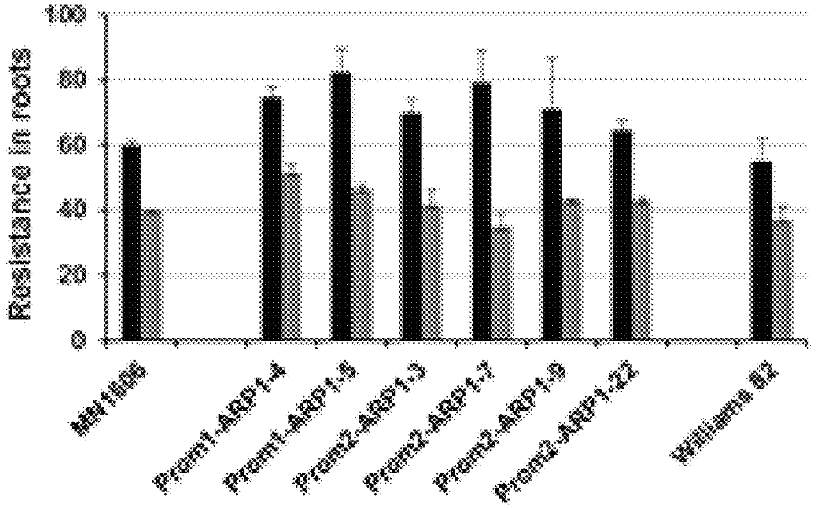
Figure 2D:
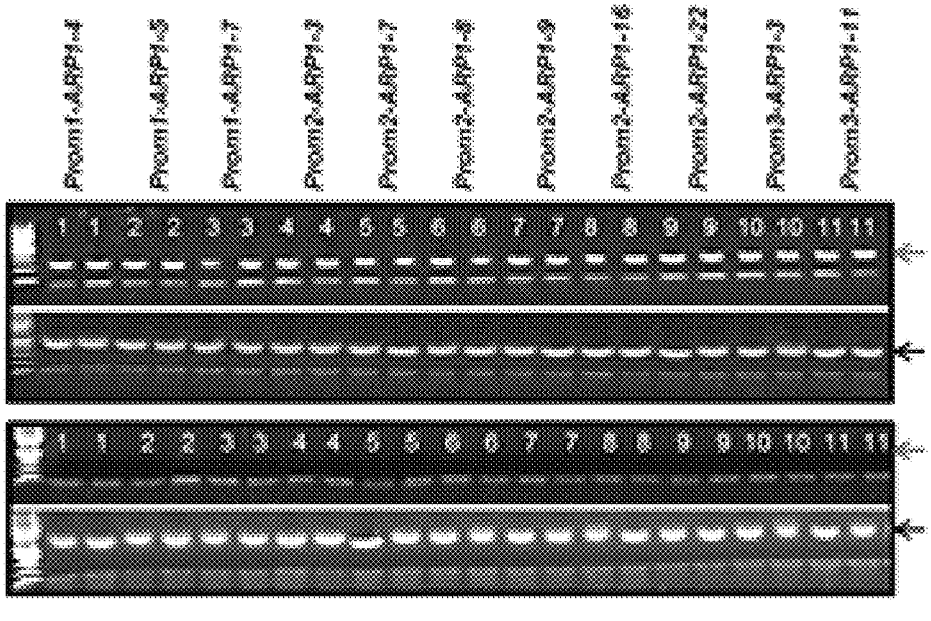
Figure 3A:
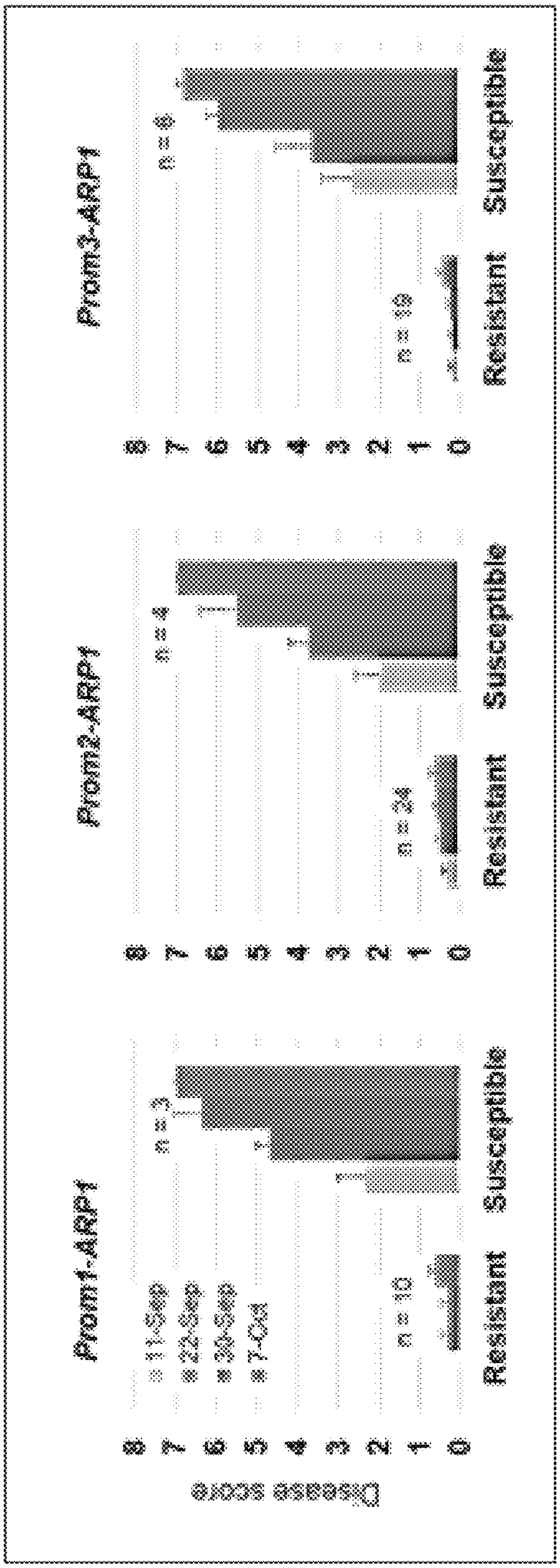
FIGS. 3A-3C show the expression of GmARP1 (SEQ ID NO: 3) enhanced SDS resistance in transgenic soybean plants in a field trial. $R_1$ plants were tested for resistance to *F. virguliforme* in field conditions in summer 2015 (June to October) and scored four times at the indicated date in FIG. 3A and FIG. 3B. All six transgenic lines of GmAPR1 showed more than 70% of plants resistant to *F. virguliforme* with no symptoms to slight yellowing with disease scores 0 and 1. The rest (less than 30%) showed severe disease symptoms with interveinal to severe chlorosis and necrosis with disease scores 2 to 7. The SDS susceptible line, Williams 82 (W82) and the SDS resistant line (MN1606) were used as controls.
Figure 3B:
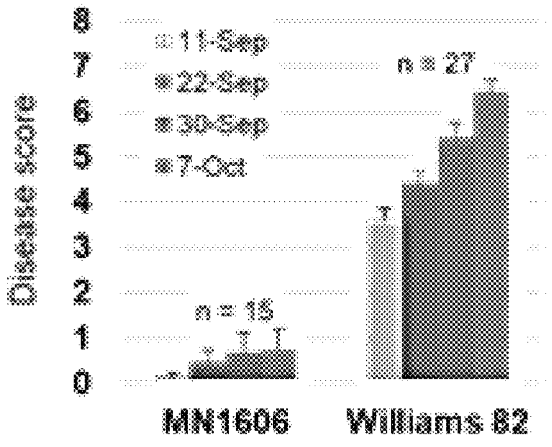
Figure 3C:
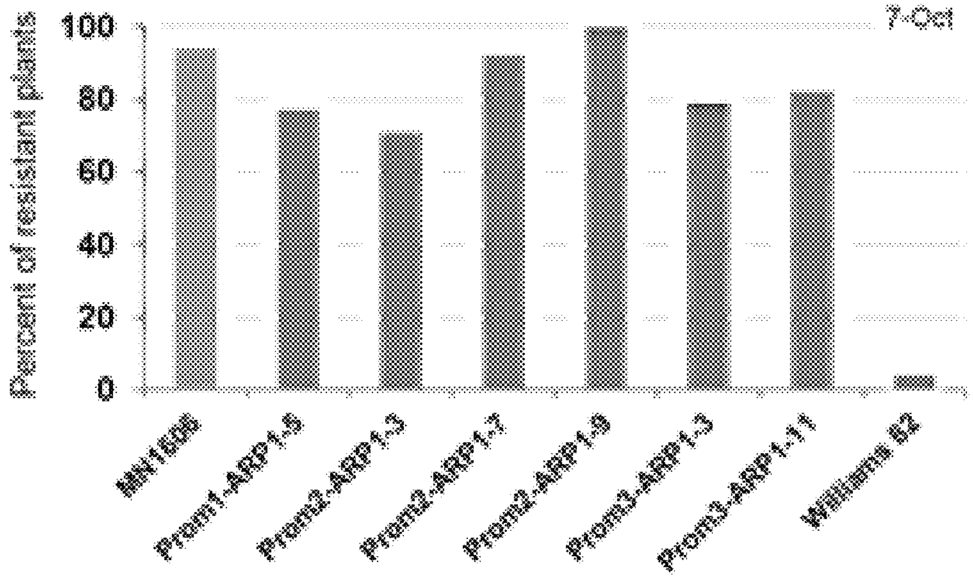
Figure 4:
FIG. 4 shows the phenotype of GmARP1 (SEQ ID NO: 3) transgenic soybean plants in a field trial. GmARP1 lines were resistant to *Fusarium virguliforme*, whereas the recipient nontrangenic line Williams 82 (W82) were susceptible. Pictures were taken on Oct. 7, 2015 (last date of scoring) while the plants were at maturity stage (R-stage) 6.0. Prom1-ARP1-5 R, represent a resistant $R_1$ progeny of the Prom1-GmARP1-5 transgenic line; Prom1-ARP1-5 S, a susceptible line of the Prom1-GmARP1-5 transgenic line. The SDS susceptible line, Williams 82 (W82) and the SDS resistant line, MN1606 were used as controls. Note that the MN1606 matured earlier than W82 and transgenic plants.

We harvested seeds from three independent transgenic lines carrying Prom1-ARP1, eight with Prom2-GmARP1, and three lines containing Prom3-GmARP1 (Table 1). $R_1$ progenies of individual transformants carrying any of the three fusion GmARP1 genes were inoculated with *F. virguliforme* Mont-1 isolate in a growth chamber. $R_1$ progenies of many of the transgenic plants showed enhanced foliar SDS resistance and reduced root rot as compared to the non-transgenic Williams 82 control plants (FIG. 2*a-c*). Molecular characterization of the infected $R_1$ plants indicated that expression of foliar and root SDS resistance among the $R_1$ progenies of multiple transformants was associated with the expression of GmARP1 transgenes (FIG. 2*d*). No transcription of endogenous GmARP1 (SEQ ID NO: 3) transcripts was detected during *F. virguliforme* infection.

We evaluated whether GmARP1 transgenes could provide enhanced SDS resistance in transgenic soybean plants under field conditions. We carried out a field trial of transgenic lines during the summer 2015. We observed that 70 to 100% transgenic $R_1$ plants descended from six transgenic $R_0$ lines, showed enhanced resistance to the SDS pathogen under field conditions (FIG. 3*a-c* and FIG. 4).

TABLE 1

Current status of soybean transformation
Glyma01g37680.1 (SAMT1, SEQ ID NOs: 1 and 16)
encoding salicylic acid methyl transferases (SEQ ID NO: 2),
(ii) Glyma12g12470.1 (New name: Glyma.12g111500)
(ARP1, SEQ ID NOs: 3 and 15) encoding
an ankyrin repeat-containing protein (SEQ ID NO: 4), (iii)
Glyma10g12400.1 (DS1, SEQ ID NOs: 5 and 17)
encoding an unknown protein (SEQ ID NO: 6), and (iv)
Glyma10g32980.1 (SEQ, SEQ ID NOs: 7 and 18) encoding
a sieve element-occlusion protein (SEQ ID NO: 5), and
(v) a *F. virguliforme*
gene, FvPO1 (SEQ ID NO: 9), encoding a polyamine
oxidase (SEQ ID NO: 10 for this study.

| Construct Number | Name of Construct | Trasnformed $R_0$ Plant Number | Number of Seeds Harvested | $R_1$ Progeny | Number of $R_2$ Seeds |
|---|---|---|---|---|---|
| ST228 | Prom1-ARP1 | 4 | 183 | — | |
| | | 5 | 196 | | |
| ST209 | Prom2-ARP1 | 3 | 355 | — | |
| | | 6 | 401 | — | |
| | | 7 | 325 | — | |
| | | 8 | 256 | — | |
| | | 9 | 412 | — | |
| | | 16 | 222 | — | |
| | | 22 | 171 | 22-1 | 160 |
| | | 23 | 169 | — | |
| ST210 | Prom3-ARP1 | 3 | 150 | 3-3 | 217 |
| ST211 | Prom1-SAMT1 | 4 | 254 | — | — |
| | | 5 | 135 | 5-1 | 234 |
| | | | | 5-4 | 176 |
| | | 11 | 150 | — | — |
| | | 12 | 123 | — | — |
| ST212 | Prom2-SAMT1 | 2 | 449 | — | — |
| | | 4 | 156 | — | — |
| | | 5 | 432 | — | — |
| | | 6 | 378 | — | — |
| | | 7 | 403 | — | — |
| | | 14 | 148 | 14-1 | 118 |
| | | | | 14-2 | 149 |
| | | | | 14-3 | 131 |
| | | | | 14-4 | 83 |
| | | 15 | 294 | — | — |
| | | 24 | 104 | — | — |
| ST213 | Prom3-SAMT1 | 4 | 170 | — | — |
| | | 18 | 197 | — | — |
| | | 19 | 166 | 19-1 | 195 |
| | | | | 19-2 | 96 |
| | | 24 | 366 | — | — |
| | | 31 | 516 | — | — |
| | | 33 | 497 | — | — |
| ST214 | Prom1-DS1 | 1 | 263 | — | — |
| | | 2 | 213 | — | — |
| | | 3 | 133 | 3-2 | 151 |
| | | | | 3-4 | 186 |
| | | 4 | 514 | — | — |
| | | 5 | 46 | — | — |
| | | 12 | 88 | — | — |
| | | 13 | 61 | — | — |
| ST215 | Prom2-DS1 | 1 | 62 | — | — |
| | | 4 | 312 | — | — |
| | | 8 | 468 | — | — |
| | | 9 | 649 | — | — |
| | | 11 | 401 | 11.2 | 208 |
| | | 12 | 49 | — | — |
| | | 13 | 232 | — | — |
| | | 14 | 49 | — | — |
| | | 15 | 238 | — | — |
| | | 20 | 443 | — | — |
| | | 21 | 255 | — | — |
| | | 24 | 408 | — | — |
| ST216 | Prom3-DS1 | 2 | 67 | 2-1 | 88 |
| | | | | 2-2 | 153 |
| | | 4 | 515 | | — |
| | | 9 | 471 | | — |
| | | 12 | 138 | | — |
| | | 13 | 247 | — | — |

TABLE 1-continued

Current status of soybean transformation Glyma01g37680.1 (SAMT1, SEQ ID NOs: 1 and 16) encoding salicylic acid methyl transferases (SEQ ID NO: 2), (ii) Glyma12g12470.1 (New name: Glyma.12g111500) (ARP1, SEQ ID NOs: 3 and 15) encoding an ankyrin repeat-containing protein (SEQ ID NO: 4), (iii) Glyma10g12400.1 (DS1, SEQ ID NOs: 5 and 17) encoding an unknown protein (SEQ ID NO: 6), and (iv) Glyma10g32980.1 (SEQ, SEQ ID NOs: 7 and 18) encoding a sieve element-occlusion protein (SEQ ID NO: 5), and (v) a *F. virguliforme* gene, FvPO1 (SEQ ID NO: 9), encoding a polyamine oxidase (SEQ ID NO: 10 for this study.

| Construct Number | Name of Construct | Trasnformed $R_0$ Plant Number | Number of Seeds Harvested | $R_1$ Progeny | Number of $R_2$ Seeds |
|---|---|---|---|---|---|
| ST217 | Prom1-FvPO1 | 2 | 400 | — | — |
| | | 3 | 344 | — | — |
| | | 6 | 292 | — | — |
| ST229 | Prom1-SEO | — | — | — | — |
| ST230 | Prom2-SEO | 3 | 207 | — | — |
| | | 7 | 52 | — | — |
| ST231 | Prom3-SEO | 0 | — | — | — |
| | | | | | — |

Construct is defined as the DNA molecule for soybean transformation. Prom1, infection inducible promoter (Glyma18g47390, SEQ ID NO: 11); Prom2, root-specific promoter (Glyma10g31210, SEQ ID NO: 12); Prom3, root-specific promoter (Glyma20g36300, SEQ ID NO: 13).

Evaluation of Transgenic Soybean Lines Containing Salicylic Acid Methyl Transferase-Like Protein Gene, Glyma01g37680.1 (GmSAMT1)

Putative transformed soybean plants carrying Prom1-GmSAMT1, Prom2-GmSAMT1 and Prom3-GmSAMT1 fusion genes were generated and maintained in the Agronomy greenhouse, ISU for $R_1$ seed production. These putative transgenic lines were characterized by PCR of genomic DNA samples prepared from young leaves. We identified lines that carried GmSAMT1 fusion genes and the bar gene (FIG. 5).

Figure 6:
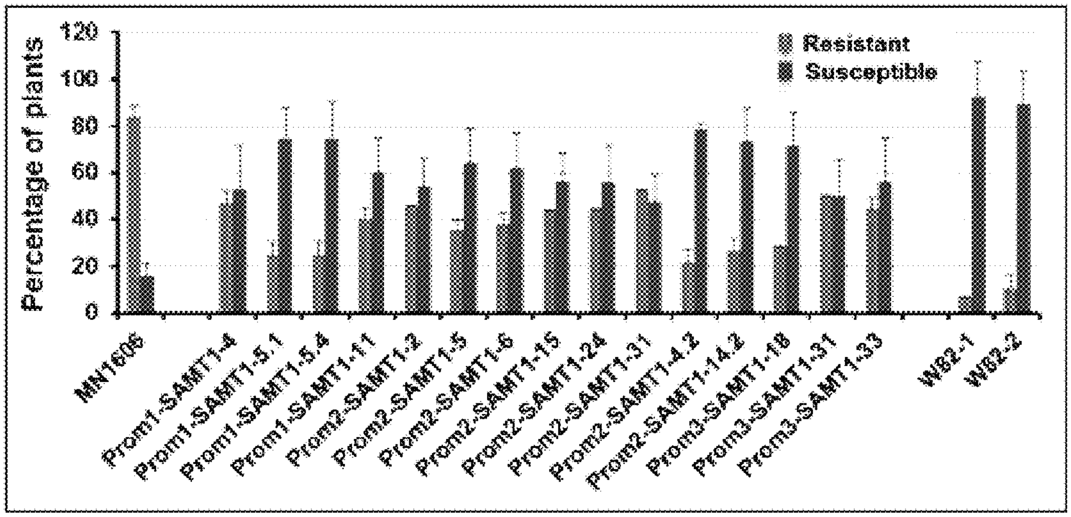
FIG. 6 shows the expression of GmSAMT1 enhanced SDS resistance progenies of three transgenic plants. Enhanced foliar resistance conferred by GmSAMT1 (SEQ ID NO: 1). Thirty progeny plants were grown in *F. virguliforme* inoculated soil, ¼ of plants were expected to be non-transgenic, most probably the more susceptible ones.

We have collected seeds from four independent transformed soybean lines carrying Prom1-GmSAMT1, six with Prom2-GmSAMT1 and six with Prom3-GmSAMT1 (Table 1). $R_1$ progenies of individual transformants carrying fusion GmSAMT1 genes were inoculated with *F. virguliforme* Mont-1 isolate in a growth chamber. $R_1$ progenies of many of the transgenic plants showed enhanced foliar SDS resistance and reduced root rot as compared to the non-transgenic Williams 82 plants in two independent experiments (FIG. 6). We evaluated whether GmSAMT1 (SEQ ID NO: 1 and 2) transgenes could provide enhanced SDS resistance in transgenic plants under field conditions. We carried out a field trial of transgenic lines during the summer 2015. We observed that 73 to 100% transgenic $R_1$ plants descended from six transgenic $R_0$ lines, showed enhanced resistance to the SDS pathogen under field conditions (FIG. 7).

(iii) Generate Transgenic Soybean Lines with a Novel Soybean Gene with Unknown Function for Enhancing SDS Resistance.

Several putative transgenic plants representing all three fusion genes generated from GmDS1 (SEQ ID NO: 5) were maintained in the ISU Agronomy greenhouse, and were characterized by PCR. We observed that most of the transformants harbor the GmDS1 (SEQ ID NO: 5) and bar genes.

We have harvested seeds from seven independent lines carrying Prom1-GmDS1, twelve carrying Prom2-GmDS1, and five containing Prom3-GmDS1 (Table 1).

Like in GmSAMT1 (SEQ ID NO: 1), $R_1$ plants of Prom2-GmDS1 showed less root rot as compared to the Williams 82 control and in three independent experiments (FIG. 8).

We evaluated whether GmDS1 (SEQ ID NO: 5) transgenes could provide enhanced SDS resistance in transgenic plants under field conditions. We carried out a field trial of transgenic lines during the summer 2015. We observed that 73 to 100% transgenic $R_1$ plants descended from six transgenic $R_0$ lines showed enhanced resistance to the SDS pathogen under field conditions (FIG. 9).

Spider mites are yield-reducing pests in soybean, which feed on the abaxial surface of leaves, and produce symptoms such as yellowing and whitish spot, bronzing, and webbing on the adaxial side of leaves. These symptoms are mostly severe, as these tinny insects multiply very quickly, with one generation being completed as short as in 5 to 8 days (English-Loeb et al., 1998; Shurtleff and Aoyagi, 2009; Scranton et al., 2013). Unfortunately, fewer studies have focused on identifying mite resistant genes. Unexpectedly, spider mites devastated our $R_0$ transgenic plants in the greenhouse in February of 2014. To our surprise, the mites could develop and feed on all plants except the one that carried the Prom2-GmDS1 transgene (FIG. 10A). We speculate that GmDS1 fusion genes could also confer resistance to insect-pests such as soybean spider mites and aphids. To test this hypothesis, we carried out a three independent mite-infection experiments in the greenhouse. Segregating $R_1$ progenies of independent transformants carrying GmDS1 (SEQ ID NO: 5) transgenes were used in this study. As expected, we found that 25% and 33% of these $R_1$ progenies were resistant to the spider mites, whereas all nontransgenic Williams 82 plants were heavily infested by spider mites (FIGS. 10, 11, 12).

Figures 5A, 5B:
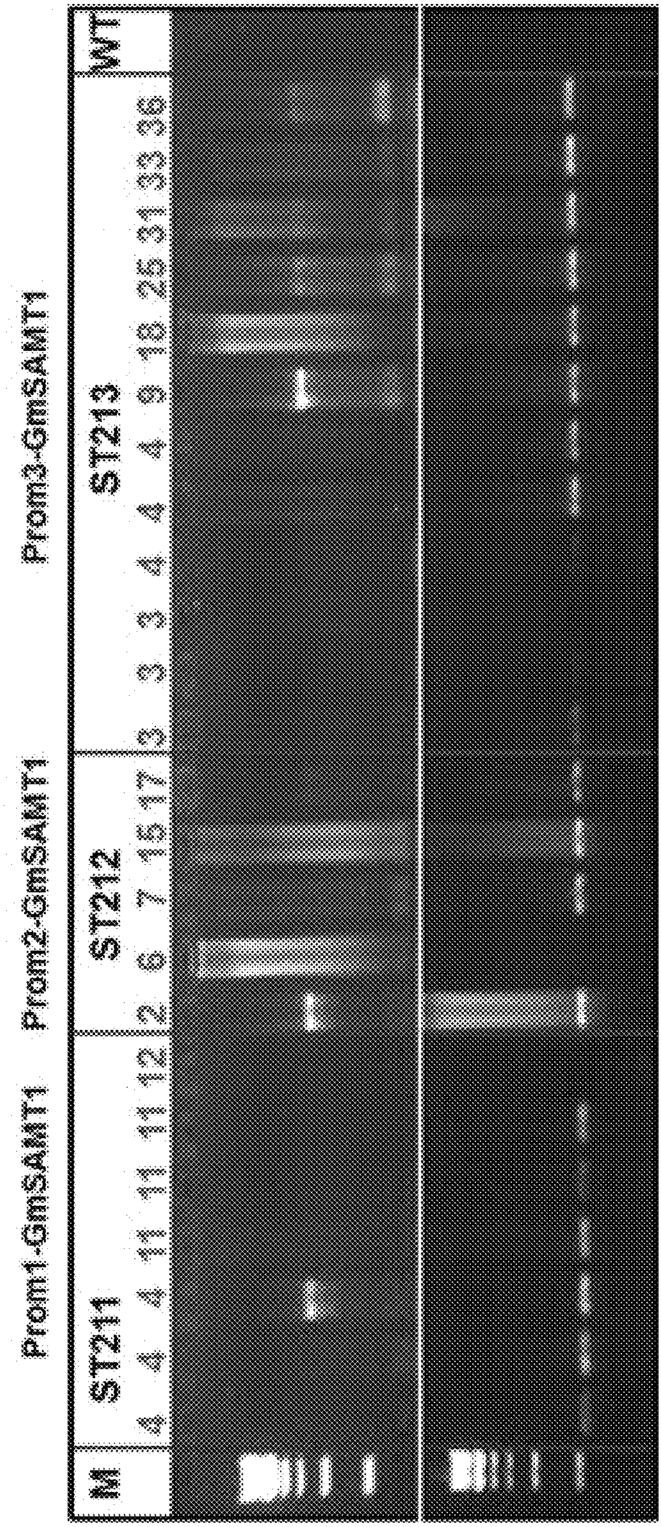
FIG. 5A shows PCR amplification of GmSAMT1 (SEQ ID NO: 1) transgene using one GmSAMT1-specific and one vector-specific primer.
FIG. 5B shows PCR amplification of the bar gene. Lines 3, 7, through 23 are independent $R_0$ plants.

Soybean aphid (*Aphis glycines*, Matsumura) is among the major yield-reducing pests of soybean (Zuang et al., 2002). Considering broad-spectrum resistance encoded by fusion GmDS1 genes to *F. virguliforme* and spider mites, we investigated if GmDS1 (SEQ ID NOs: 5 and 6) can provide any resistance against soybean aphids and preliminary results are presented in FIG. 13. A young third trifoliate from each soybean plant was infected with 10 wingless cohorted aphids protected by clip cages (Bioquip products #1458; FIG. 5A). The aphids were left to multiply and aphid populations were counted on the infected leaves 7 days following infection. The number of aphids on the inoculated trifoliate was significantly reduced in the three GmDS1 (SEQ ID NO: 5) transgenic plants and aphid resistant line, Loose, as compared to Williams 82 (FIG. 13).

The soybean cyst nematode (SCN), *Heterodera glycines*, is a very serious soybean pest. Female nematodes attack and feed in soybean roots leading to death of the entire plants and therefore severe yield losses occur across the globe (Koenning et al., 2012). Fortunately, genes conferring SCN resistance are deployed to create SCN resistant cultivars to protect the crop losses. Two of these genes have been recently isolated; and both encode distinct novel mechanisms (Cook et al., 2012; Liu et al., 2012). We investigated if the fusion GmDS1 genes confer any immunity to SCN. Twenty seeds of individual transgenic $R_0$ soybean plants were tested for possible expression of SCN resistance as follows. Single seeds of each soybean transformant were planted in individual container filled with Muscatine soil of Iowa (naturally infested with SCN HG type 0). Containers were randomly placed in a greenhouse water bath and incubated at constant 27° C. under natural light conditions.

Four weeks later, roots were washed to harvest female nematode cysts, which were counted under a microscope (Youssef et al., 2013). Several $R_1$ progenies of two independent transformants carrying the Prom2-GmDS1 fusion gene showed four-fold less cysts as compared to that in non-transgenic Williams 82 plants (FIG. 14). This is an indication that expression of GmDS1 (SEQ ID NOs: 5 and 6) in soybean roots enhances partial resistance to SCN. We propose that some of the lines carrying the Prom3-GmDS1 fusion gene could show even higher levels of SCN resistance because Prom3 (SEQ ID NO: 13) is a much stronger root-specific promoter than Prom2 (SEQ ID NO: 12).

GmDS1 (SEQ ID NOs: 5 and 6) confers broad-spectrum resistance to both fungal pathogens and pests. To understand how the little protein functions to provide broad-spectrum resistance, we have localized the protein to sub-cellular compartments by tagging the protein with GFP. We observed that GmDS1 (SEQ ID NO: 6) is localized to plasma membrane (FIG. 15). It could be a receptor and recognizing common ligands from multiple organisms for signaling induction of plant defenses.

(iv) Generate Transgenic Soybean Lines with a Sieve Element-Occlusion (SEO) Protein Gene, Glyma10g32980.1 During *F. virguliforme* Infection.

Transformation of the Prom1-SEO1 and Prom3-SEO1 fusion genes into soybean is currently in progress. We have harvested seeds from two lines of carrying the Prom2-SEO1 fusion gene and progenies of these two lines will be investigated for possible SDS resistance (Table 1).

(v) Generate Transgenic Soybean Lines with the *F. virguliforme* Polyamine Oxidase Gene, FvPO1, for Enhancing SDS Resistance.

Previously we discovered a *F. virguliforme* polyamine oxidase gene (FvPO1, SEQ ID NOs: 9 and 10) that is induced during infection. We then created knockouts of this gene to investigate its function during infection. To our surprise fvpo1 mutants were able to infect soybean leaves better than the wild type *F. virguliforme* isolate. We observed that without the FvPO1 (SEQ ID NO: 9) gene there is increased ability for the fungus to infect. To gain a better understanding of the effect of this polyamine oxidase enzyme on soybean responses to infection, we looked for differential gene expression following infection with *F. virguliforme* mutant fvpo1 and complemented fvpo1 mutant with the FvPO1 gene. In the fvpo1 mutant there was an increased expression of three stress related/antifungal receptor like kinases (FIGS. 16A, 16B, and 16C). There were also two defense related gene, which were not triggered in the fvpo1 mutant and show the same expression in the mutant as the water control. These two proteins are a wound inducible protein and a stress response protein which only had increased expression in the inoculation with the fungal strain with the functional FvPO1 (SEQ ID NO: 9) gene (FIGS. 16D and 16E). These molecular data confirm the phenotypic data that fvpo1 can infect soybean leaves and etiolated hypocotyls. This suggests that the FvPO1 (SEQ ID NO: 9) gene may trigger defense responses.

To determine if expression of FvPO1 (SEQ ID NO: 9) gene in soybean can enhance SDS resistance, we developed a fusion gene by fusing to Promoter 1 (Prom1, SEQ ID NO: 11), which is active only during infection process, with the coding sequence of FvPO1. *A. tumefaciens* containing the fusion gene was used to transform soybean cotyledonary nodes. We obtained three independent transformants (FIG. 17). Seeds have recently become available for these three independent events (Table 1). We infected leaves of progenies of one of the three transformants; expression of FvPO1 (SEQ ID NOs: 9 and 10) made the soybean susceptible to the pathogen (FIG. 18). Results from root inoculation of the progenies of this transformant showed reduced root rot symptoms when compared with the control lines (FIG. 19A). The foliar SDS symptoms in the three lines were reduced when compared with the transformation background line Williams 82, but comparable to the known susceptible line Spencer (FIGS. 19B and 20). Multiple replications of the root inoculation testing are being started now to confirm the initial results.

(vi) Introgress the Genes Created in this Investigation into Elite Soybean Lines.

The suitable genes showing promising improvement in SDS resistance will be crossed into elite soybean lines.

Example 2

```
>Glyma12g12470.1:peptide (SEQ ID NO: 4)
MKKLKNTQFS SQQGAAASQP RPLLHKELVG EKKVMNSEFN

EAVEKGDMDN FVNVLEQVCR ERNLPLSAVF DQVTWTGDSL

LHVAADKGKQ HIVELIADHF QELLIRRNAR GDTALHVAVR

SMNSNIVKFI LNKDKKLAKE KNQYGNTPLH EAVYSEHVDV

VNQILLADKD VVHSLNKSNQ SPLYLAVANG NLEILNLLLD

LYANLNYKIV LEIQNLS*

Glyma12g12470.1:cds (SEQ ID NO: 3)
atgaagaaac tgaagaacac acaattctca agtcaacaag

gtgcagcagc ttcacaaccg agaccactgc tgcacaagga

acttgttggg gagaaaaaag ttatgaattc tgagtttaat

gaagctgttg aaaaaggaga tatggataac tttgttaacg

tgttggagca agtttgtaga gaaaggaacc tacctttgtc

tgctgttttt gatcaagtca cctggactgg tgattcgttg

cttcatgtgg cagcagataa ggggaaacaa catattgtag

agctgattgc tgatcacttt caagagcttc ttattagaag

aaacgctaga ggtgatactg cacttcatgt tgctgtgagg

tctatgaact ccaatatagt caagttcatt ctcaacaaag

ataaaaagct agcaaaagaa aagaatcaat atgggaacac

tcctttgcac gaggctgtct acagtgagca tgttgatgtg

gttaatcaga ttttacttgc cgataaggat gtggttcatt

ctttgaacaa gtcaaaccaa tcaccgttat atttggcagt

tgcgaatggg aacttggaaa ttcttaatct tctattggat

ttatatgcaa acctaaacta taagatagta ttagagattc

agaatctatc ttaa

Glyma12g12470.1 position = Gm12:10709217..
10710099 (- strand) (SEQ ID NO: 15)
ATGAAGAAAC TGAAGAACAC ACAATTCTCA AG7CAACAAG

GTGCAGCAGC TTCACAACCG AGACCACTGC TGCACAAGGA
```

-continued

ACTTGTTGGG GAGAAAAAAG TTATGAATTC TGAGTTTAAT

GAAGCTGTTG AAAAAGGAGA TATGGATAAC TTTGTTAACG

TGTTGGAGCA AGTTTGTAGA GAAAGGAACC TACCTTTGTC

TGCTGTTTTT GATCAAGTCA CCTGGACTGG TGATTCGTTG

CTTCATGTGG CAGCAGATAA GGGGAAACAA CATATTGTAG

AGCTGATTGC TGATCACTTT CAAGAGCTTC TTATTAGAAG

AAACGCTAGA GGTGATACTG CACTTCATGT TGCTGTGAGG

TCTATGAACT CCAATATAGT CAAGTTCATT CTCAACAAAG

ATAAAAAGCT AGCAAAAGAA AAGAATCAAT ATGGGAACAC

TCCTTTGCAC GAGGCTGTCT ACAGTGAGCA TGTTGATGTG

GTTAATCAGA TTTTACTTGC CGATAAGGAT GTGGTTCATT

CTTTGAACAA GTCAAACCAA TCACCGTTAT ATTTGGCAGT

TGCGAATGGG AACTTGGAAA TTCTTAATCT TCTATTGGAT

GTTCCATTAC CTTCAGATCT TCCACGGTGC CTTGGAAACT

CTCCACTTCA TGCTGCCATA CTGGAACGGA AGCCTGGTAT

TCAGTTTTTA TTTTTCTTTT CAAATCAATG ACTATATATT

CATGGTACTT TAATTAAACA CTACATATGG ACCAGTAATA

TGGCCCAATA ATTAAAATAT ATAGCTGGTC AGTAGAGTAA

TCTATACCTT ATAAATTGGT TTTGTTAAGT TATATGCAAA

CCTAAACTAT AAGATAGTAT TAGAGATTCA GAATCTATCT

TAA

Glyma01g37680.1:peptide (SEQ ID NO: 2)
MEVTQVLHMN GGSGETSYAN NSLVQQKVIC LTKGMREEAI

SSLYRSMLPR SLAVADLGCS SGPNTFFVIS EAIKSVEKLC

RELNHQSPEY QIYMNDLPGN DFNNIFKSLD SFKEKLCNEI

IEAGHGIGSC FFNGVPGSFY GRIFPTKSLH FVHSSYSLMW

LSKVPDGVEN NKGNIYMAST SSLNVLKAYY EQYQKDFSLF

LKCRAEEIVE GGRMVLTFLG RRSDDRSSKE CCYIWELLAM

ALNDMVSKVL MKKWLMKNSL KIILIFY*

Glyma01g37680.1:cds (SEQ ID NO: 1)
atggaagtga cacaagtact gcacatgaat ggaggctcgg gagaaacaag ctatgcaaac aattccttag ttcagcaaaa ggtgatttgt ttgacaaagg gtatgagaga ggaagccata agcagcctct accgcagcat gctcccaaga agccttgcag ttgcggactt gggttgctct tctggaccaa acactttctt cgtgatatct gaagctataa aatcggtgga gaagctttgt cgagaactga atcatcagtc accagaatac cagatctaca tgaacgatct tcccgggaat gatttcaaca acatcttcaa gtcccttgac agcttcaaag agaaactgtg taatgaaata atagaagctg ggcatggaat tggttcatgt tttttcaatg -continued gggttccagg ttctttttat ggcaggatct ttccaaccaa aagtctgcat tttgttcatt cctcgtacag ccttatgtgg ctatccaagg ttcctgatgg tgtagagaac aataagggca acatttacat ggccagcaca agttccttaa atgtccttaa ggcttattac gagcaatatc aaaaggattt ctcgttgttt ttgaagtgtc gagcggaaga aatcgtggaa gggggtcgta tggttctgac atttttggga agaagaagcg acgatcgatc tagcaaagag tgttgctata tatgggaact tttggctatg gctcttaatg atatggtctc gaaggtactt atgaaaaaat ggttaatgaa gaatagtttg aaaataattt taatatttta ttaa Glyma01g37680.1 position = Gm01:49999699..
50001148 (- strand) (SEQ ID NO: 16)
CAATAGAAGC ATAAAAAATC AACTACCTTA GAAAAGGAGT

GAAAGGAAGA AAAGAGAAAC AAGAATGGAA GTGACACAAG

TACTGCACAT GAATGGAGGC TCGGGAGAAA CAAGCTATGC

AAACAATTCC TTAGTTCAGG TATAAATGCA TGTTTAATAA

CAAGTAAAAT CTCATCATCT TCTACTTTTT TTTTCTCCAT

TGCATTCATT AATTGGCAAT TAATTTTATG TTCATATATA

TGTTTAGACA AATTAATTTT TGCTAGCTAG GTTAAGAAAC

TTTGATAGTA ATAGCAAAGA GCTATGCAGA AAGTTTGATA

TTTATTGGTT GGAACTGATC TGAATGAATG AATATTGCAG

CAAAAGGTGA TTTGTTTGAC AAAGGGTATG AGAGAGGAAG

CCATAAGCAG CCTCTACCGC AGCATGCTCC CAAGAAGCCT

TGCAGTTGCG GACTTGGGTT GCTCTTCTGG ACCAAACACT

TTCTTCGTGA TATCTGAAGC TATAAAATCG GTGGAGAAGC

TTTGTCGAGA ACTGAATCAT CAGTCACCAG AATACCAGAT

CTACATGAAC GATCTTCCCG GGAATGATTT CAACAACATC

TTCAAGTCCC TTGACAGCTT CAAAGAGAAA CTGTGTAATG

AAATAATAGA AGCTGGGCAT GGAATTGGTT CATGTTTTTT

CAATGGGGTT CCAGGTTCTT TTTATGGCAG GATCTTTCCA

ACCAAAAGTC TGCATTTTGT TCATTCCTCG TACAGCCTTA

TGTGGCTATC CAAGGTATAC TATAATTTCT CTGTTAATTT

TTTTTTGTAG ACCACACATA ATATTCATTT GACTGTAATA

ATTTCACGTT AATTAATCTA TGTGTTCAGT GAATATTATG

TTAACTATAC AATAGCACCA GATTATTATT ACAAGTCCTA

TAGGAGTGAC AAAGTATTAT ATTTTCCTCA CAATAAAATC

AATTTTTTGT GTAAAAAATT GAAATAAATT AAATAAACTT

TCTATAGATA TCCTGCGCAA CACACCTTTC TATAGGAGTG

-continued

ACAAACTTAT TACAGATGCA AGATTAAAAT AATTATGTGT

TTATTGATTA TTAATTAGGT TCCTGATGGT GTAGAGAACA

ATAAGGGCAA CATTTACATG GCCAGCACAA GTTCCTTAAA

TGTCCTTAAG GCTTATTACG AGCAATATCA AAAGGATTTC

TCGTTGTTTT TGAAGTGTCG AGCGGAAGAA ATCGTGGAAG

GGGGTCGTAT GGTTCTGACA TTTTTGGGAA GAAGAAGCGA

CGATCGATCT AGCAAAGAGT GTTGCTATAT ATGGGAACTT

TTGGCTATGG CTCTTAATGA TATGGTCTCG AAGGTACTTA

TGAAAAAATG GTTAATGAAG AATAGTTTGA AAATAATTTT

AATATTTTAT TAAATAAGAT AAAATTGGTT AAAATTTATT

TATATTTAAA

Glyma10g12400.1:peptide (SEQ ID NO: 5)
MYSVEMAPYG RFIANILIAV MFVCLFFVTN IVAQDSEIAP

TGQLEAGTGF DLPVSKVMMC SSVLASLLAF MLQ*

Glyma10g12400.1:cds (SEQ ID NO: 4)
atgtattctg tggaaatggc accttatggt agattcattg ctaacatttt gatagctgtg atgtttgttt gcttgttttt tgtgaccaac attgtggcac aggattcaga gattgctcct acaggtcaat tggaggctgg aactgggttt gatttgcctg tttctaaggt gatgatgtgt tcttcagtgt tggcatctct tttggcattc atgttgcagt ga >Glyma10g12400.1 position = Gm10:13394800..
13395797 (+ strand) (SEQ ID NO: 17)
GTTATCCAAG CCATGTGGGA AACTCTAAGT GTAGGGTGTA

TCATAAGTGG TAGTTGCCTT ATTGTTCCTA CATAGCTGTG

ATGTAAGAGT CTCTTTGAGG ATGCTATGCC ACCCTTCCCC

AACTAGCTTT GATTGGTCTT GTGGGGTCTT CAAAAGCCTT

AACCAAAAAG GGATAGTAAC ATTCAAAATG GTTAATGTTT

AATGCACCAT TTTACCAACT TAAAAATCGT GACCATATTA

TGATGTAACA AGTTTAATTT TCCTAAGTCC TATATAAGTT

CAACCCTTGG CTCAATCTTT CAACAATTCA GTTGCTTACT

AATACTAATC TCTTAATTCT CTTTGGCCAT TTCTTTAGTA

ACATTAAGAT AATGTATTCT GTGGAAATGG CACCTTATGG

TAGATTCATT GCTAACATTT TGATAGCTGT GATGTTTGTT

TGCTTGTTTT TTGTGACCAA CATTGTGGCA CAGGATTCAG

AGATTGCTCC TACAGGTCAA TTGGAGGCTG GAACTGGGTT

TGATTTGCCT GTTTCTAAGG TGATGATGTG TTCTTCAGTG

TTGGCATCTC TTTTGGCATT CATGTTGCAG TGAATTGGAA

GACAGTGGGT TTCAAATTTG AACTTGTTGG GGATAATCTT

ACTTTGTATG TGGGTTAAAA TTCATATGTT TATATATATA

CTATATACTA TATGTTTGGT TGTTGAAAAT GGTACTGTAT

-continued

TTTTGGGCAT TTTGTAAGAT TAGCTTTATG AGGAGCTACA

GTTACAAGTA TGTAATTTCT ACTCAGCTAT TATTGGTGTG

AGCTGATATA TTAATATAAT TGTTAAGTTC CTTGTAATTG

ATGATTTTTG CTGTTTCAAG TTATCAAATT CTTCGAAAGT

GACTTTCTTG TAGCATGCTG CTTTGAATTA TAGTCCAACT

TTGTCCAAAA ATGTGACATT TGAAGTATAA TAACTGGATA

AGTAAACAAT TCCTATTTTA TAAATTTGAG TCTTTATT

Glyma10g32980.1:peptide (SEQ ID NO: 8)
MSCKPPSDVI AHKTTLAILN NLKNYEWNAK AVLTLAAFAL

EYSEFWLLAQ YQQSDPLAKS VAILKRVPVL TRQAALQKYR

QAIVELIIFE LEKLTNDLGV AIEQISVDVY WAIITIVSLT

TRIDCLTTES YVTEQKQELS HYGQKINIIL SKLKKQITLC

RQQIDAAEYY RKLRKLFQTP TEIMEVFKIL IFNKDVPQPL

YCGATKTMVD ITVLKRKHVY LLIS5LDITE EEISVFQTVY

DSIKTSDQYS IVWIPIVESW TVEYDNKFED FKCKMPWYAV

QHSGPIAGYQ YIKEEWHYKS KPMVVVLSPQ GKVQHSNAFH

LIQAHGTRAF PFTTVKQEQI NNETDWVGSV IGNIYPIINT

WFNIYDTLYE QIKEKKYIFL YGGKDKEWIQ QFTKNVSALA

SDAAITEANI SIEWLCVEKE DRSVMRRFWG GIESLFVTKV

HKAVDAVTLE VQKMLSYKNE AGWSLLISEG SSVVVCGHGK

TITDTVEGFQ NWKGSLTKKG FGLSFQGYHQ KIVDITHRCS

YLEISNVSGR LPETIKCPDC PRIMEIFVSY KCCHNNTIHY

*

>Glyma10g32980.1:cds (SEQ ID NO: 7)
atgtcatgca aacctccaag tgatgtaatt gctcacaaaa ctacactggc catactgaac aatctcaaaa actatgagtg gaatgcaaag gcagtgctga cactggcagc ttttgcactc gaatatagcg agttttggct gctagcacag taccaacaat cagaccctct tgcaaaatct gtggctattc tgaagagagt gccagtgctc acaaggcaag cagcacttca aaagtatcgc caagccatcg ttgagttaat tatctttgag ttggagaagc ttactaatga tttgggggtt gcaatagagc aaatctctgt tgatgtttac tgggcgatca tcactattgt ttccttaacc actcggattg attgtctcac cactgaatcg tatgttacag agcaaaaaca agaactgtct cactatggac aaaagatcaa catcatactc agcaaactca agaagcagat cactctttgc agacaacaga tagatgcggc agaatattat cgcaagctga ggaagctttt ccaaactccc actgaaataa tggaggtgtt taagattctg attttcaaca aggatgttcc tcagccactt tattgtggtg ctactaagac catggtcgac atcactgtgc -continued

```
tgaaaaggaa gcatgtttac ttgttgattt cttccctaga
cattacggag gaagagattt cagtattcca aacagtttat
gattcaatta aaactagtga tcagtatgag attgtatgga
ttcccattgt ggaggaatgg accgttgagt acgacaacaa
atttgaggat tttaaatgca agatgccttg gtatgcggtg
cagcattctg gacccatagc agggtaccag tacattaagg
aagaatggca ctataaaagc aagcctatgg ttgtggtgtt
gagtcctcaa gggaaggtgc aacactcaaa cgcattccat
ttgatccagg ctcatggaac cagagctttc cccttcacaa
ctgtcaaaca agaacaaatc aacaatgaga ccgactgggt
tggctccgta ataggcaata tttaccccat cataaacact
tggtttaata tttatgatac tttatatgag cagatcaaag
agaaaaagta cattttcttg tacggaggca aggacaaaga
gtggatccaa cagttcaeca agaatgttag tgcccttgca
agtgatgccg ctataacgga ggcaaatatt tccatagagt
ggctttgtgt ggaaaaggaa gacagaageg tgatgaggcg
cttttggggt ggcattgaga gtttgtttgt gactaaggtt
cataaggcag ttgatgcagt gactctagaa gtgcaaaaga
tgctctctta caagaatgaa gctggatggt ctctccttat
tagcgaaggg tcttctgtgg tggtgtgtgg tcatggaaag
acaatcacgg atacagtgga agggtttcag aattggaaag
gaagtttgac caaaaagggc tttgggttat ccttccaagg
ataccatcag aagattgtgg acatcactca ccgttgctca
taccttgaaa tttctaatgt ttcaggaagg ttaccagaga
ccatcaaatg cccagattgt ccacggatta tggagatttt
cgtcagctat aaatgctgcc acaacaatac cattcactac
tag
```

>Glyma10g32980.1 position = Gm10:41340518.. 41344659 (+ strand) (SEQ ID NO: 18)

```
ATGTCATGCA AACCTCCAAG TGATGTAATT GCTCACAAAA
CTACACTGGC CATACTGAAC AATCTCAAAA ACTATGAGTG
GAATGCAAAG GCAGTGCTGA CACTGGCAGC TTTTGCACTC
GAATATAGCG AGTTTTGGCT GCTAGCACAG TACCAACAAT
CAGACCCTCT TGCAAAATCT GTGGCTATTC TGAAGAGAGT
GCCAGTGCTC ACAAGGCAAG CAGCACTTCA AAAGTATCGC
CAAGCCATCG TTGAGGTTAA CGATTTGGTG AAAGCAACGT
TGCAAGTCAT TGAAGTTAAT TATCTTTGAG TTGGAGAAGC
TTACTAATGA TTTGGGGGTT GCAATAGAGC AAATCTCTGT
TGATGTTTAC TGGGCGATCA TCACTATTGT TTCCTTAACC
ACTCGGATTG ATTGTCTCAC CACTGAATCG TATGTTACGT
ACGTACATTT CATACTATCG TATATAATAA AACCTAATTA
CTTTATTGCA ATGAAAATCT TAAAATGTAT AATTTTATTG
ATTATTTAAG AGAGCAAAAA CAAGAACTGT CTCACTATGG
ACAAAAGATC AACATCATAC TCAGCAAACT CAAGAAGCAG
ATCACTCTTT GCAGACAACA GATAGGTCAG CAATTGAAAT
AATTGCCTTT GCATGCCTTT AATTATTAAT TCTGTCATCA
TGTTTTTTTC TCCTTAAAGC AAATATGCTT TTGATTCAAA
CTTCAAAGCT ATGATTTCAT GGAATAAAAG GCACCGAGCA
GTGAATGAGA TTCTAATTAA TTAAAGGATT TGTTTCTGTT
ATTTCAGATG CGGCAGAATA TTATCGCAAG CTGAGGAAGC
TTTTCCAAAC TCCCACTGAA ATAATGGAGG TGTTTAAGAT
TCTGATTTTC AACAAGGATG TTCCTCAGCC ACTTTATTGT
GGTGCTACTA AGACCATGGT TTGTGATTCC CTGTTAAAAT
CCTACTTTCA TGTTCGAAAT TTGTTCTCTT CGGAGAGAAA
ATGAGTGTGA ATTTTCTGGT TTGGTTGGTC AATATCCTAC
TCATATTCTA GGCTTTAGAA ATAAAACACC AGATAAAGTG
GAGGGAGGGG GTGTCGAAAA CCTAGAACTA AAATGAATAT
AATGTTAATG CATAAAAAAT AAACATGACT TATGCCACAC
CTTCGCATTG ATCCTCTGTT AGTTCCTCAA ACCACACACG
GACACTCTCG TCCCTATGAT GGAGAAAGTC GATAGCTTGG
CCTCCACATC GAAGTCAGAC TCTGACAACA GCCACCACCT
CACCCCTCAC GAGTTCACTA CTCCCATCCC CTTTGTAACG
AAACACCACA CCTACCTCGT CGGCTTCAGC CAATGCTCCT
TCCTCCTCAC GCAGCACATC CATGCGCCAC ATGACATCGT
CTTCTAGCGG CTTCATTGGA TCTGCACCGC TCTAACCCCA
ACACTACCCT CTTTGCCACC TTCACCAAAT AGGCACTGCC
CCAACCCCAA CCACCTTGTT ATGGAATGCG ACCCTGGAGG
TGCTAATCGT TGAGAAGACG GAAGGATTTC GCAAAGCACG
GAAGAGTGTT GATGGTTGAT TGGATGTTTT CACGTTGAGT
AATTTTGTGT TTGATTGATG TTTTCTGGGT TACAGATGCT
TCGTGATTTT GTGTTTTTAT CTTTACTTTA ATTGATTCTT
TTACAGCTGC CAAAAATTAT AATTATAATT TCGAAATGAA
TATTGATTAT TTTTTAAGCG TCACAAATGA TATTTTAAAA
AAAAGTTAAC AACAACATCA TCACTAGCTA ATAGAAAAAT
TCTAACAACG AGAATTAAAA ACAAAAAATT TCAAATATAA
AAAAATAAAA ACGAACAAAA TTTTAATGAG AGATCAAAAA
TAAAATTTAA GTATATATAA GAGAGTACTA ACATATTTAA
TCTTATTTTA ATTAAAAAAA TTGTTTTTAA AAATATTAAT
AATAATGTAA TTTGTTTGTT TTTTTTATAA AAAAAATGAC
```

-continued

AAGTTTGACG AAAGTTATTT GTTTGATATT CATCTCACTC
ACCCTCGAAT CAACCCAAAA AGTCAAGTTA AAAAAAATAA
TTGAGTAATG ATATATGAAG TACTCTTTAT TTAAATTTTA
TTTTTAAATA CTCCATCAAT ATCTTTTAAT TTTCTTTATT
ACTATCACAT CATGAATTCT ATATACATAT TTTTGTTCAT
TTTTAAAAAC CATGTGATAT TTATCAAACA TTTTTCAAAA
TAATTATTGG ATGTCGACGA GCATTTGAAA AAGGATAGCT
CATTTGAATA CAATTTAATA ATAAATCTGA TGATAACTAT
AAATATAAGA TAGTGATCTA AAAGAATCTA CTGAAGATTG
AAGAAAGATT AATTTAACTA TACAGAAATA TAAGATGGGA
TCTAAAAGAA TTAATCAAGC TTCAAGTTGT ATAATGGGGT
TAAATGGTTA TCTCATGTAT ATGTTTGTTT TGTGTCATCT
TTCCTGGGTT AGTAAGTATT TGTATCCACT TATTGGGTAT
AAATATTATC TAACCTTAAT TGGGTCATGG CCCTTGGCAA
TGATGGCTGA CTTTGTAGTT GGTGTTATGG TATCACTGGT
ACCCTTCTTA ATGTAATACA TTTGCTGCAT GATCCAAAAA
AAAATATTAT TCTCAGTTCA GATTTTCACA ACAATTTCTA
CAATAAAGAA AGAGAAGAGA AGAGTGAGAT AAAAACAAGT
ATTGTAAAAT AAGTAAGGAA AAATAAGTGT TGTACGTGAG
AAATTTGAAA AAAGATTATC CCTATTCCCG TGTCTGTGAA
ATTCGATGCT TTCAAGTATC ATTCATTTCA AGCATCTGTA
ATTTTTAATC CTGATTCAGT TGTTGCTTGC TACGTAGGTC
GACATCACTG TGCTGAAAAG GAAGCATGTT TACTTGTTGA
TTTCTTCCCT AGACATTACG GAGGAAGAGA TTTCAGTATT
CCAAACAGTT TATGATTCAA TTAAAACTAG TGATCAGTAT
GAGATTGTAT GGATTCCCAT TGTGGAGGAA TGGACCGTTG
AGTACGACAA CAAATTTGAG GATTTTAAAT GCAAGATGCC
TTGGTATGCG GTGCAGCATT CTGGACCCAT AGCAGGGTAC
CAGTACATTA AGGAAGAATG GCACTATAAA AGCAAGCCTA
TGGTTGTGGT GTTGAGTCCT CAAGGGAAGG TGCAACACTC
AAACGCATTC CATTTGATCC AGGCTCATGG AACCAGAGCT
TTCCCCITCA CAACTGTCAA ACAAGAACAA ATCAACAATG
AGACCGACTG GGTTGGCTCC GTAATAGGCA ATATTTACCC
CATCATAAAC ACTTGGGTAA GTAAATTTCA CAGAAAACAA
AAGTTGTTAG AATATCATAT AAATATATAT CATGAGTTTA
ATGGTTATTT ACTACACTTG ACAGTATAAA GTAATTTCAC
AAATTATCAC GTATATGAAT TATCATACAT GATGAAGTAG
GATTAAATAA TACTATAAAA TTATTTTACG TTGTGTTAGA
TTTTCTCTAC ATTATATACT AGTTTAATAT TTATGATACT

-continued

TTATATGAGC AGATCAAAGA GAAAAAGTAC ATTTTCTTGT
ACGGAGGCAA GGACAAAGAG TGGATCCAAC AGTTCACCAA
GAATGTTAGT GCCCTTGCAA GTGATGCCGC TATAACGGAG
GCAAATATTT CCATAGAGTG GCTTTGTGTG GAAAAGGAAG
ACAGAAGCGT GATGAGGCGC TTTTGGGGTG GCATTGAGAG
TTTGTTTGTG ACTAAGGTTC ATAAGGCAGT TGATGCAGTG
ACTCTAGAAG TGCAAAAGAT GCTCTCTTAC AAGAATGAAG
CTGGATGGTC TCTCCTTATT AGCGAAGGGT CTTCTGTGGT
GGTGTGTGGT CATGGAAAGA CAATCACGGA TACAGTGGAA
GGGTTTCAGA ATTGGAAAGG AAGTTTGACC AAAAAGGGCT
TTGGGTTATC CTTCCAAGGA TACCATCAGA AGATTGTGGA
CATCACTCAC CGTTGCTCAT ACCTTGAAAT TTCTAATGTT
TCAGGAAGGT TACCAGAGAC CATCAAATGC CCAGATTGTC
CACGGATTAT GGAGATTTTC GTCAGCTATA AATGCTGCCA
CAACAATACC ATTCACTACT AG

>PO6063 FvP01 (SEQ ID NO: 9)
atgcgggttccgtcttcgcaactccttgcgctgtcctatggca
tcttcttaggcacagcccaagccgcagtgatacctcgtgatgg
cgccaagacctgcaaaaagaccaaggtcgccgtcctcggcgcc
ggcgtcgctggcataacggctgctcaggccctgcacaatgcct
cgatccatgactttctcattgttgagcacaacgactacatcgg
cggtcgagtcaggcatgcttcttttggcaaggggcctgacggc
aaccccttgaccgtggaactcggtgccaactgggtcgaaggcc
ttggatcaaaccccatctggcgtttggctcaaaagcacaaggt
taagagcacctttgccgactatgactccgtcctcacctacgac
caaaacggatcagccgactacggagaggtctttgaggaattcg
acgtgagctttgaaaacgcgacaaaggacgccggatacatcca
gactctgaacctccaagacacttcggtccgtacgggactcagc
ctcgcaggatggaagcccaagcaggatcagtacaagcaactcg
ccgactggtgggggtgggactttgaaaccgcctttactccgga
gcagtctggtttccagttcggaattgccggaaacaatgctacg
ttcaagcatttcaacgacgagtccaacctcgttatcgaccaac
ggggtttcaacacctggatcattggagaggcgaacgagttcct
caaaggcggggagcaagatcccaggctccttcttaacacgact
gtcaagaaggtccactacggcaaagaaggcgttgttattctca
acgaggacgacagctgcatcgaggctgaatttgcaatttgcac
attctctcttggtgtgctgcagaacgaagctgtttcctttgac
ccggtcctcccccgctggaagagagaagccatcgagcaattcc
agatgggcacctacaccaagatcttcatgcagttcaacgagtc
gttctggccagaagagggtcaatactttctctacgctgatccc
gaggagcgaggctatttccccctttccagccgctaaacgcca -continued agggcttccttgagggctctaatgttctctttgctaccgtcgt tgcttcgcaggcgtacaaggtagaggcacaatcggacgaggaa accaaggagcagattcttgaggtgcttcgatccatgtttcctg ataagcacgtccctgagccgattgactttatgtatcctcgatg gacgtcaacagagcaagtcccctctccttgtttgcatttgtca caattactaaccacattcttcaggtggtcgtatggctcttaca gcaactggccagtcggcatgaccctcgaaaagcaccagaacct tcgtgccaacgttgaccggctgtggtttgcaggcgaggccaac tccgcagagtttttcggatatctgcatggagcgtggtatgagg gtcaagaggcaggagagcggattgccaggattattggtggaaa ggaaacagagaagtcgcagcagatgaagaagtatgaggttctt catggaacgacgactgcggatgagtataatgacgccaacgggt ggtcgacgccattggatgtctaa
Underlined is Rt-PCr primer Protein (SEQ ID NO: 10)
M R V P S S Q L L A L S Y G I F L G T A Q A

A V I P R D G A K T C K K T K V A V L G A G

V A G I T A A Q A L H N A S I H D F L I V E

H N D Y I G G R V R H A S F G K G P D G N P

L T V E L G A N W V E G L G S N P I W R L A

Q K H K V K S T F A D Y D S V L T Y D Q N G

S A D Y G E V F E E F D V S F E N A T K D A

G Y I Q T L N L Q D T S V R T G L S L A G W

K P K Q D Q Y K Q L A D W W G W D F E T A F

T P E Q S G F Q F G I A G N N A T F K H F N

D E S N L V I D Q R G F N T W I I G E A N E

F L K G G E Q D P R L L L N T T V K K V H Y

G K E G V V I L N E D D S C I E A E F A I C

T F S L G V L Q N E A V S F D P V L P R W K

R E A I E Q F Q M G T Y T K I F M Q F N E S

F W P E E G Q Y F L Y A D P E E R G Y F P L

F Q P L N A K G F L E G S N V L F A T V V A

S Q A Y K V E A Q S D E E T K E Q I L E V L

R S M F P D K H V P E P I D F M Y P R W T S

T E Q V P S P C L H L S Q L L T T F F R W S

Y G S Y S N W P V G M T L E K H Q N L R A N

V D R L W F A G E A N S A E F F G Y L H G A

W Y E G Q E A G E R I A R I I G G K E T E K

S Q Q M K K Y E V L H G T T T A D E Y N D A

N G W S T P L D V

-continued

Promoter 1 (Glyma18g47390) (SEQ ID NO: 11)
GTGGATCATTGGGTTCtAgaTCAACCTTACCTTTTGATTAAGG

AAATCTAATTAGTATAAGATTACCTGGTGATAATGATGCGATA

TGATGACGAGTTATTTGCATAACGTTTCGATCATCCACGATAC

CACGTCCATGTTCAGGTTGAAACTCTTTTAATGTTTATTGGTG

GGGATGTTATAACCCGGCCCAGACCTAATTAATGCATTGAATG

TCGAAGGTGAATTGGTCCAAACTTCCTTCTTCCTCTTTTATTT

TCGAGAATCATGCTTATAGTTTTACCCGGATCCTCCTATGAGA

AGAAAAAAATCGAACGAAGGGAAATCAAACTGTTGCCTAAAGAT

AAGAAAAAAATAAATTAATTTCATAAAAAATTAAGTTTTTTAATT

AATTAATATATATAAATAATTTTGCGAAAAACTACGTGATCTTAA

GTTTCTAACTGCATGGGAAAATTATGGAAGTGTAGAGATCATT

CTTGTTGAAGTAAAACTAAATTTTTCAAGATTTTTCTTTAAAT

AAAGTAAATAATGAGATTTTGATAAAAAAAAAATCTTAATTTTA

AAAATAATAATAATAATGATTTTTCATTTTCATAATTTATGTT

TCAAATAAAAGAGGTTAAATAAAAAAATTAAAATTTATTAATAC

TTTACACATTAACTAAAGATAAGGTTTTTAACAAATGCATTAA

AAGTGCAATCGATCGACCAGTTTCCACTTTTCTATCCATAAGT

AGACTTCCAAACCAACAAAGACCTTTTCAATGACTAGTTCTGT

AAAAATAGTAAAGATTTTTATCGATTTATGTTTCGTCTCTCGT

CGCAACCTCCGAGCATGTTGTGACAATAAGTAAAAAACAAAAT

TGTAAGAGTTTAAATTTTTTTAGCTAAATTTAATTTTTTTTTC

ATTAGTATAAATTTTGTTTATATTATTTATTTATTTTCACTTA

TACTACAATTCATTCAAATAAATGATGATAAATTTGTCTATTT

TTTTTTATTTCTATGATCTATCTAAATAATACACCTTTTCTGC

TCTATTTGTCATTTAATTTTATCCTTTCTATTTCATACTAATC

ACCAATCCATATAAATTTCTTTAGTTTATAAAAGGTGAGATAG

TCTCAAAGCTAACGTTGAATAACGTTGAAATACTTGATAGATT

GATC

Promoter 2 (Glyma10g31210) (SEQ ID NO: 12)
GCCTAAGACATGGAGGGGAAAATAAATGTATGTACATTCTGCT

TGTTTTCTCAAATGCTGACTGGTTAAGATATTTAGAGTGGGTA

TAATATTTGTCCAGAAGGATAAAGATAAAATAAAACACGTTAA

TTATCCTTATGATTTTGCAACTGTAAAATATTACAGGGGAGGA

GAAGGATCACAATTTTACCAGTGGATATTCCAAGTTTCATAAA

TTAAAATGAAACTCAGATTCATAAATTTTGAAGTCATTGTCAT

GAAACTCTTTAATTACCTGCTTTGTAACAACTTTCTTGTTGGT

ACCATTACTATCTTATTCTTGTCCTATTGCATGGGTAGAAAAA

AGAAAAATATAGGGAAACAAAATAAAAGAGAGAAAATGATAGA

TATGATACATGATTTGATGAGAAATGAAAAAAGAAATAAGAAA

-continued

AAATAGAATAGAAATGACATGGAATTGAAAAATAAATGTTTGA

TAATGTATGTTTATATATAATTACTCTTTCTTGGGTTTCTACC

AAATCTGATATCTTTCTTGGGTAGGAACTAGGAACCATTCATT

TACGTCACTTGTGTGAGTGAGTCATCTTCAAACACTGTAGTGC

GTTTGAAATCCTTTGGTAGTGTAAGAAAACAAATCAAAGCTAG

GATGCAACTTAGTTATTCCCCGGATAGAAATCTCGGATCAAAG

ACTTTATGGACAAGATAAATATACAAAAGTGGACACTCGTTTC

TTTCAAAATATAATTACGAGTTGATACATATTTGAAAATTTAA

TCAATTTTTTTGTCTTAAATAATTTCCATTATCCTCCACTTAC

TCTATACGATATCTATACCGCAACATGAAGGACCAATTAAAGA

CTTTGGCAAAAATAAAATAAAACCATTGAGGTGTAGCACTAGT

TCCGGTCTTCTAAATGCTCACAAGATTTTAATTAGCCGCCGGG

TCTCAAAATTAACATGTTCTAAATCATGCACCAGCTCCCATTA

TAAAACTAAATATTTCAGGCACAGGTAGTGGATACGTACAATG

TCGAATGTACACTGTAATACTGAAAAATTTATCATGACAAGCG

TGCAGACATTAAGAATGCTTCCACCATCAAATAGTTTACTAAT

TCTACAAATGCTAAAATATCTATATCAATGGCTCCGTACCCTA

TAAATAGCTAGCTTCCCATGCTACAAAATACACATCTCTCACA

CACTTAGAATTAAGTTAGTAGCGAGGAAGAAAAATGAAGGTTG

TTTACCTCTTCGTTGTGCTGATGGCTTTGGCATCATCTGTTGC

CTTTGCTTATGATCCAAGCCCCCTGCAAGACTTTTGTGTCGCT

ATCAATGACACCAAAGCTGGTGG

Promoter 3 (Glyma10g31210) (SEQ ID NO: 13)
cggtcccaacaactagtttgcattctcatatcatatattgccc aaaaatatttctcggttcataacctcaaggtccgtttgatttg aagaacaaaaatgggaaggccattaaatttgcaaagaatttca agatgggataacacaacaaaaaaaattatttatttaatttttc aagtggtcatgaaatagtattaaaaatgataaaatgctgaaca ccaaattatgaagataaaaatactactcaatttaccttttcat tattatgctaaatcttgactctcccagacattaaaactacagt catatgtaatcatcactaccactttgaatgccactatcattat ctccatcttcttcatctttatcatttcttataaagataacttt gtcaattcttaagaatttatattattatatttgccaagttatt -continued cggtacacataaaatactgaataagataagcttatatattata cgcaatttttcattagtccatctaatacttatgcgtatcaaac atcatacagtaaaagaaaaatatttgcgttgtatttcaatttc aaaataatagactgatcaaggtgtgctattactcaactatacc atacagtattacagtcctggagtgcatattctatttctcaata aacaacaaacgtagttgttggttttgagattttgaatattata tgaattttcctattcgcctaagactatggaggggaaaataaat gtatgcactttctgttttcccgaatacctactgcttaagatat taagagtgggtataatatttgtccagaagggtaaagataaaat aaaactcgttatgcttatgatttcgcaattgtaaaatagaaca ggggtggagaaggatcacaatttttccagtggatattccaagt ttctaaaactaactcagattcataaattttgaagtcattgtca ttaaagtctttaaatacctgctttgcaactcttcttttcggta caagtcttttcttacccttatcctattgcatgggtagaaaaaa aaaagataaggaaacaaataaaagaaaaaagacaaaatgatag atatgataactgatttgatgaaaaatgaaaagaagaaataata agaaaaatagaatagaaatgaaatggaagtgaaagaaaatgta tgataatgtatatgtgtggtaatttctacaaaatctgatatct ttcttgggtaggaaccattcatttacgtcacttgtgtgagtga ggcatcttcaaacactgtagttcgtctgaaatccttgggtagt gtaagaaaataaatcaaggatgcaactaagttattgcctggat agagatctcagatcagagactttgacgacaagataaatatgca atagtggacactcgtttctttcaaaatataattacgggttgat acttggaagaaaatttaatcaatttttttgccttaaataatttc cattatcctccactttctctatacgatatctataccgtaactt gaagaaccaattaaagacttaggctaaaataaaataaaaccat tgaggtgtagcactagttctggtcttctaaatgctcagaagat tttaattagccgccaggtctcaaaasaaacatgztctaaatca tacacctgctcatattataaaagtaatatttcaagcacaggta gtggatacgtacaatgtcgagtgtacatggtaatactgaaaaa atcatcatgacgatgatgtggggcatcttaatctaatattttg acaagcgtgcag

What is claimed is:

1. A modified plant with improved resistance to Sudden Death Syndrome compared to the Sudden Death Syndrome of a corresponding plant with no such modification; said modified plant having a heterologous nucleotide sequence which includes a *Fusarium* resistance nucleic acid sequence, said *Fusarium* resistance nucleic acid sequence encoding a protein selected from the group consisting of:

*Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO: 10, or a protein having at least 95% identity to SEQ ID NOs: 2, 4, 6, 8, or 10.

2. The plant of claim 1 wherein said *Fusarium* resistance nucleic acid is one or more of the following: SEQ ID NOS: 1, 3, 5, 7, or 9.

3. The plant of claim 1 wherein said *Fusarium* resistance nucleic acid encodes one or more proteins selected from the group consisting of: SEQ ID NOS: 2, 4, 6, 8, or 10.

4. An isolated nucleic acid molecule operably linked to a heterologous promoter, said nucleic acid molecule comprises a nucleotide sequence selected from the group consisting of:

(a) a nucleotide sequence comprising the sequence set forth in SEQ ID NO: 5, wherein said nucleotide sequence encodes a protein for *Fusarium*-resistance;

(b) a nucleotide sequence having at least 95% sequence identity to the sequence of SEQ ID NO: 5 wherein said nucleotide sequence encodes a protein for *Fusarium* resistance;

(c) a nucleotide sequence comprising the sequence set forth in SEQ ID NO:5, wherein said nucleotide sequence encodes a protein for *Fusarium*-resistance;

and wherein the nucleotide sequences of (a)-(b) contain at least one substitution modification relative to SEQ ID NO: 5.

5. A vector comprising the nucleic acid molecule of claim 4.

6. A plant cell having stably incorporated in its genome the nucleic acid molecule of claim 4.

7. The plant cell of claim 6, wherein said plant cell is from a dicot plant.

8. The plant cell of claim 6, wherein said dicot plant is soybean.

9. The plant cell of claim 7 wherein said plant cell is a root cell.

10. A method for conferring or improving *Fusarium* resistance in a plant, said method comprising:

transforming said plant with a nucleic acid molecule comprising a heterologous sequence operably linked to a promoter that induces transcription of said heterologous sequence in a plant cell; and regenerating stably transformed plants, wherein said heterologous sequence comprises a nucleic acid molecule that encodes one or more *Fusarium* resistance protein sequences selected from the group consisting of:

*Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 as set forth in SEQ ID NO: 6, and *F. virguliforme* polyamine oxidase as set forth in SEQ ID NO: 10, or a protein having at least 95% identity to SEQ ID NOs: 2, 4, 6, 8, or 10.

11. The method of claim 10 wherein said nucleic acid is one or more of the following: SEQ ID NOS: 1, 3, 5, 7, or 9.

12. The method of claim 10 wherein said nucleic acid sequence includes:

(a) a nucleotide sequence comprising the sequence set forth in SEQ ID NOs: 1, 3, 5, 7 or 9;

(b) a nucleotide sequence having at least 95% sequence identity to the sequence of SEQ ID NOs: 1, 3, 5, 7, or 9; and (c) a nucleotide sequence that encodes the protein sequence of SEQ ID NOs: 2, 4, 6, 8, or 10.

13. The method of 10, wherein said plant is a dicot.

14. The method of 10, wherein said dicot is soybean.

15. A nucleotide construct comprising:

a nucleic acid molecule of claim 4, wherein said nucleic acid molecule is operably linked to a promoter that drives expression in a host cell.

16. A method for conferring or improving *Fusarium* resistance of a plant, said method comprising:

stably introducing into the genome of a plant, at least one nucleotide construct comprising a *Fusarium* resistance nucleic acid molecule operably linked to a heterologous promoter that drives expression in a plant cell, wherein said nucleic acid molecule encodes a polypeptide selected from the group consisting of: *Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO: 10, or a polypeptide having at least 95% identity to SEQ ID NOs: 2, 4, 6, 8, or 10.

17. A method of plant breeding for *Fusarium* resistance comprising:

identifying a plant with a heterologous *Fusarium* resistance nucleic acid encoding an *Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 as set forth in SEQ ID NO: 6, and *F. virguliforme* polyamine oxidase as set forth in SEQ ID NO: 10, or a nucleic acid encoding a protein having at least 95% identity to SEQ ID NOs: 2, 4, 6, 8, or 10;

selecting said resistant plant for use a parent plant;

crossing said parent plant with itself or a second plant, so that the *Fusarium*-resistance trait is passed to progeny seed; and harvesting progeny seed from said parent plant.

18. A modified plant with improved broad-spectrum pathogen resistance, compared to a corresponding plant with no such modification; said modified plant having a heterologous nucleotide sequence which includes a *Fusarium* resistance nucleic acid sequence, said *Fusarium* resistance nucleic acid sequence encoding a protein selected from the group consisting of:

*Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO:10, or a protein having at least 95% identity to SEQ ID NOs: 2, 4, 6, 8, or 10.

19. The plant of claim 18 wherein said *Fusarium* resistance nucleic acid is one or more of the following: SEQ ID NOS: 1, 3, 5, 7, or 9.

20. The plant of claim 18 wherein said *Fusarium* resistance nucleic acid encodes one or more proteins selected from the group consisting of: SEQ ID NOs: 2, 4, 6, 8, or 10.

21. The method of claim 18 wherein said plant pathogen is a soybean cyst nematode.

22. The method of claim 18 wherein said plant pathogen is an aphid.

23. The method of claim 18 wherein said plant pathogen is a Fungus.

24. A method for conferring or improving pathogen resistance in a plant, said method comprising:

transforming said plant with a nucleic acid molecule comprising a heterologous sequence operably linked to a promoter that induces transcription of said heterologous sequence in a plant cell; and regenerating stably transformed plants, wherein said heterologous sequence comprises a nucleic acid molecule that encodes one or more *Fusarium* resistance protein sequences selected from the group consisting of: *Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO: 10, or a protein having at least 95% identity to SEQ ID NOs: 2, 4, 6, 8, or 10.

25. The method of claim 24 wherein said nucleic acid is one or more of the following: SEQ ID NOS: 1, 3, 5, 7, or 9.

26. The method of claim 24 wherein said nucleic acid sequence includes:

(a) a nucleotide sequence comprising the sequence set forth in SEQ ID NOs: 1, 3, 5, 7 or 9;

(b) a nucleotide sequence having at least 95% sequence identity to the sequence of SEQ ID NOs: 1, 3, 5, 7, or 9; and (c) a nucleotide sequence that encodes the protein sequence of SEQ ID NOs: 2, 4, 6, 8, or 10.

27. The method of 24, wherein said plant is a dicot.

28. The method of 24, wherein said dicot is soybean.

29. A method for conferring or improving pathogen resistance of a plant, said method comprising:

stably introducing into the genome of a plant, at least one nucleotide construct comprising a *Fusarium* resistance nucleic acid molecule operably linked to a heterologous promoter that drives expression in a plant cell, wherein said nucleic acid molecule encodes a polypeptide selected from the group consisting of: *Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO: 10, or a polypeptide having at least 95% identity to SEQ ID NOs: 2, 4, 6, 8, or 10.

30. The method of claim 29 wherein said plant pathogen is a soybean cyst nematode.

31. The method of claim 29 wherein said plant pathogen is an aphid.

32. The method of claim 29 wherein said plant pathogen is a Fungus.

33. A method of plant breeding for *Fusarium* resistance comprising:

identifying a plant with a heterologous *Fusarium* resistance nucleic acid encoding an *Glycine max* salicylic acid methyl transferase as set forth in SEQ ID NO: 2, *Glycine max* ankyrin repeat-containing protein as set forth in SEQ ID NO: 4, *Glycine max* sieve element-occlusion protein as set forth in SEQ ID NO: 8, *Glycine max* disease susceptibility 1 (GmDS1) as set forth in SEQ ID NO: 6, and *F. virguliforme* polyamine oxidase as set forth in SEQ ID NO: 10, or a nucleic acid encoding a protein having at least 95% identity to SEQ ID NOs: 2, 4, 6, 8, or 10; selecting said resistant plant for use a parent plant; crossing said parent plant with itself or a second plant, so that the *Fusarium* resistance trait is passed to progeny seed; and harvesting progeny seed from said parent plant.

34. The method of claim 18 wherein said plant pathogen is a soybean cyst nematode.

35. The method of claim 18 wherein said plant pathogen is an aphid.

36. The method of claim 18 wherein said plant pathogen is a Fungus.

* * * * *

SEQUENCE LISTING

<160> NUMBER OF SEQ ID NOS: 18

<210> SEQ ID NO 1
<211> LENGTH: 804
<212> TYPE: DNA
<213> ORGANISM: Glycine max

<400> SEQUENCE: 1

```
atggaagtga cacaagtact gcacatgaat ggaggctcgg gagaaacaag ctatgcaaac      60

aattccttag ttcagcaaaa ggtgatttgt ttgacaaagg gtatgagaga ggaagccata     120

agcagcctct accgcagcat gctcccaaga agccttgcag ttgcggactt gggttgctct     180

tctggaccaa acactttctt cgtgatatct gaagctataa aatcggtgga gaagctttgt     240

cgagaactga atcatcagtc accagaatac cagatctaca tgaacgatct tcccgggaat     300

gatttcaaca acatcttcaa gtcccttgac agcttcaaag agaaactgtg taatgaaata     360

atagaagctg ggcatggaat tggttcatgt tttttcaatg ggttccagg ttctttttat      420

ggcaggatct ttccaaccaa aagtctgcat tttgttcatt cctcgtacag ccttatgtgg     480

ctatccaagg ttcctgatgg tgtagagaac aataagggca acatttacat ggccagcaca     540

agttccttaa atgtccttaa ggcttattac gagcaatatc aaaaggattt ctcgttgttt     600

ttgaagtgtc gagcggaaga aatcgtggaa gggggtcgta tggttctgac atttttggga     660

agaagaagcg acgatcgatc tagcaaagag tgttgctata tatgggaact tttggctatg     720

gctcttaatg atatggtctc gaaggtactt atgaaaaaat ggttaatgaa gaatagtttg     780

aaaataattt taatatttta ttaa                                             804
```

```
<210> SEQ ID NO 2
<211> LENGTH: 267
<212> TYPE: PRT
<213> ORGANISM: Glycine max

<400> SEQUENCE: 2

Met Glu Val Thr Gln Val Leu His Met Asn Gly Gly Ser Gly Glu Thr
1               5                   10                  15

Ser Tyr Ala Asn Asn Ser Leu Val Gln Gln Lys Val Ile Cys Leu Thr
            20                  25                  30

Lys Gly Met Arg Glu Glu Ala Ile Ser Ser Leu Tyr Arg Ser Met Leu
        35                  40                  45

Pro Arg Ser Leu Ala Val Ala Asp Leu Gly Cys Ser Ser Gly Pro Asn
    50                  55                  60

Thr Phe Phe Val Ile Ser Glu Ala Ile Lys Ser Val Glu Lys Leu Cys
65                  70                  75                  80

Arg Glu Leu Asn His Gln Ser Pro Glu Tyr Gln Ile Tyr Met Asn Asp
                85                  90                  95

Leu Pro Gly Asn Asp Phe Asn Asn Ile Phe Lys Ser Leu Asp Ser Phe
            100                 105                 110

Lys Glu Lys Leu Cys Asn Glu Ile Ile Glu Ala Gly His Gly Ile Gly
        115                 120                 125

Ser Cys Phe Phe Asn Gly Val Pro Gly Ser Phe Tyr Gly Arg Ile Phe
    130                 135                 140

Pro Thr Lys Ser Leu His Phe Val His Ser Ser Tyr Ser Leu Met Trp
145                 150                 155                 160

Leu Ser Lys Val Pro Asp Gly Val Glu Asn Asn Lys Gly Asn Ile Tyr
                165                 170                 175

Met Ala Ser Thr Ser Ser Leu Asn Val Leu Lys Ala Tyr Tyr Glu Gln
            180                 185                 190

Tyr Gln Lys Asp Phe Ser Leu Phe Leu Lys Cys Arg Ala Glu Glu Ile
        195                 200                 205

Val Glu Gly Gly Arg Met Val Leu Thr Phe Leu Gly Arg Arg Ser Asp
    210                 215                 220

Asp Arg Ser Ser Lys Glu Cys Cys Tyr Ile Trp Glu Leu Leu Ala Met
```

```
225                 230                 235                 240

Ala Leu Asn Asp Met Val Ser Lys Val Leu Met Lys Lys Trp Leu Met
                245                 250                 255

Lys Asn Ser Leu Lys Ile Ile Leu Ile Phe Tyr
            260                 265


<210> SEQ ID NO 3
<211> LENGTH: 654
<212> TYPE: DNA
<213> ORGANISM: Glycine max

<400> SEQUENCE: 3

atgaagaaac tgaagaacac acaattctca agtcaacaag gtgcagcagc ttcacaaccg      60

agaccactgc tgcacaagga acttgttggg gagaaaaaag ttatgaattc tgagtttaat     120

gaagctgttg aaaaaggaga tatggataac tttgttaacg tgttggagca agtttgtaga     180

gaaaggaacc tacctttgtc tgctgttttt gatcaagtca cctggactgg tgattcgttg     240

cttcatgtgg cagcagataa ggggaaacaa catattgtag agctgattgc tgatcacttt     300

caagagcttc ttattagaag aaacgctaga ggtgatactg cacttcatgt tgctgtgagg     360

tctatgaact ccaatatagt caagttcatt ctcaacaaag ataaaaagct agcaaaagaa     420

aagaatcaat atgggaacac tcctttgcac gaggctgtct acagtgagca tgttgatgtg     480

gttaatcaga ttttacttgc cgataaggat gtggttcatt ctttgaacaa gtcaaaccaa     540

tcaccgttat atttggcagt tgcgaatggg aacttggaaa ttcttaatct tctattggat     600

ttatatgcaa acctaaacta taagatagta ttagagattc agaatctatc ttaa           654


<210> SEQ ID NO 4
<211> LENGTH: 217
<212> TYPE: PRT
<213> ORGANISM: Glycine max

<400> SEQUENCE: 4

Met Lys Lys Leu Lys Asn Thr Gln Phe Ser Ser Gln Gln Gly Ala Ala
1               5                   10                  15

Ala Ser Gln Pro Arg Pro Leu Leu His Lys Glu Leu Val Gly Glu Lys
            20                  25                  30

Lys Val Met Asn Ser Glu Phe Asn Glu Ala Val Glu Lys Gly Asp Met
        35                  40                  45

Asp Asn Phe Val Asn Val Leu Glu Gln Val Cys Arg Glu Arg Asn Leu
    50                  55                  60

Pro Leu Ser Ala Val Phe Asp Gln Val Thr Trp Thr Gly Asp Ser Leu
65                  70                  75                  80

Leu His Val Ala Ala Asp Lys Gly Lys Gln His Ile Val Glu Leu Ile
                85                  90                  95

Ala Asp His Phe Gln Glu Leu Leu Ile Arg Arg Asn Ala Arg Gly Asp
            100                 105                 110

Thr Ala Leu His Val Ala Val Arg Ser Met Asn Ser Asn Ile Val Lys
        115                 120                 125

Phe Ile Leu Asn Lys Asp Lys Lys Leu Ala Lys Glu Lys Asn Gln Tyr
    130                 135                 140

Gly Asn Thr Pro Leu His Glu Ala Val Tyr Ser Glu His Val Asp Val
145                 150                 155                 160

Val Asn Gln Ile Leu Leu Ala Asp Lys Asp Val Val His Ser Leu Asn
                165                 170                 175
```

-continued

```
Lys Ser Asn Gln Ser Pro Leu Tyr Leu Ala Val Ala Asn Gly Asn Leu
            180                 185                 190

Glu Ile Leu Asn Leu Leu Leu Asp Leu Tyr Ala Asn Leu Asn Tyr Lys
        195                 200                 205

Ile Val Leu Glu Ile Gln Asn Leu Ser
    210                 215


<210> SEQ ID NO 5
<211> LENGTH: 222
<212> TYPE: DNA
<213> ORGANISM: Glycine max

<400> SEQUENCE: 5

atgtattctg tggaaatggc accttatggt agattcattg ctaacatttt gatagctgtg      60

atgtttgttt gcttgttttt tgtgaccaac attgtggcac aggattcaga gattgctcct     120

acaggtcaat tggaggctgg aactgggttt gatttgcctg tttctaaggt gatgatgtgt     180

tcttcagtgt tggcatctct tttggcattc atgttgcagt ga                        222


<210> SEQ ID NO 6
<211> LENGTH: 73
<212> TYPE: PRT
<213> ORGANISM: Glycine max

<400> SEQUENCE: 6

Met Tyr Ser Val Glu Met Ala Pro Tyr Gly Arg Phe Ile Ala Asn Ile
1               5                   10                  15

Leu Ile Ala Val Met Phe Val Cys Leu Phe Phe Val Thr Asn Ile Val
            20                  25                  30

Ala Gln Asp Ser Glu Ile Ala Pro Thr Gly Gln Leu Glu Ala Gly Thr
        35                  40                  45

Gly Phe Asp Leu Pro Val Ser Lys Val Met Met Cys Ser Ser Val Leu
    50                  55                  60

Ala Ser Leu Leu Ala Phe Met Leu Gln
65                  70


<210> SEQ ID NO 7
<211> LENGTH: 1683
<212> TYPE: DNA
<213> ORGANISM: Glycine max

<400> SEQUENCE: 7

atgtcatgca aacctccaag tgatgtaatt gctcacaaaa ctacactggc catactgaac      60

aatctcaaaa actatgagtg gaatgcaaag gcagtgctga cactggcagc ttttgcactc     120

gaatatagcg agttttggct gctagcacag taccaacaat cagaccctct tgcaaaatct     180

gtggctattc tgaagagagt gccagtgctc acaaggcaag cagcacttca aaagtatcgc     240

caagccatcg ttgagttaat tatctttgag ttggagaagc ttactaatga tttgggggtt     300

gcaatagagc aaatctctgt tgatgtttac tgggcgatca tcactattgt ttccttaacc     360

actcggattg attgtctcac cactgaatcg tatgttacag agcaaaaaca agaactgtct     420

cactatggac aaaagatcaa catcatactc agcaaactca agaagcagat cactctttgc     480

agacaacaga tagatgcggc agaatattat cgcaagctga ggaagctttt ccaaactccc     540

actgaaataa tggaggtgtt taagattctg attttcaaca aggatgttcc tcagccactt     600

tattgtggtg ctactaagac catggtcgac atcactgtgc tgaaaaggaa gcatgtttac     660

ttgttgattt cttccctaga cattacggag gaagagattt cagtattcca aacagtttat     720
```

-continued

```
gattcaatta aaactagtga tcagtatgag attgtatgga ttcccattgt ggaggaatgg    780

accgttgagt acgacaacaa atttgaggat tttaaatgca agatgccttg gtatgcggtg    840

cagcattctg gacccatagc agggtaccag tacattaagg aagaatggca ctataaaagc    900

aagcctatgg ttgtggtgtt gagtcctcaa gggaaggtgc aacactcaaa cgcattccat    960

ttgatccagg ctcatggaac cagagctttc cccttcacaa ctgtcaaaca agaacaaatc   1020

aacaatgaga ccgactgggt tggctccgta ataggcaata tttaccccat cataaacact   1080

tggtttaata tttatgatac tttatatgag cagatcaaag agaaaaagta cattttcttg   1140

tacggaggca aggacaaaga gtggatccaa cagttcacca agaatgttag tgcccttgca   1200

agtgatgccg ctataacgga ggcaaatatt tccatagagt ggctttgtgt ggaaaaggaa   1260

gacagaagcg tgatgaggcg cttttggggt ggcattgaga gtttgtttgt gactaaggtt   1320

cataaggcag ttgatgcagt gactctagaa gtgcaaaaga tgctctctta caagaatgaa   1380

gctggatggt ctctccttat tagcgaaggg tcttctgtgg tggtgtgtgg tcatggaaag   1440

acaatcacgg atacagtgga agggtttcag aattggaaag gaagtttgac caaaaagggc   1500

tttgggttat ccttccaagg ataccatcag aagattgtgg acatcactca ccgttgctca   1560

taccttgaaa tttctaatgt ttcaggaagg ttaccagaga ccatcaaatg cccagattgt   1620

ccacggatta tggagatttt cgtcagctat aaatgctgcc acaacaatac cattcactac   1680

tag                                                                 1683
```

```
<210> SEQ ID NO 8
<211> LENGTH: 560
<212> TYPE: PRT
<213> ORGANISM: Glycine max

<400> SEQUENCE: 8

Met Ser Cys Lys Pro Pro Ser Asp Val Ile Ala His Lys Thr Thr Leu
1               5                   10                  15

Ala Ile Leu Asn Asn Leu Lys Asn Tyr Glu Trp Asn Ala Lys Ala Val
            20                  25                  30

Leu Thr Leu Ala Ala Phe Ala Leu Glu Tyr Ser Glu Phe Trp Leu Leu
        35                  40                  45

Ala Gln Tyr Gln Gln Ser Asp Pro Leu Ala Lys Ser Val Ala Ile Leu
    50                  55                  60

Lys Arg Val Pro Val Leu Thr Arg Gln Ala Ala Leu Gln Lys Tyr Arg
65                  70                  75                  80

Gln Ala Ile Val Glu Leu Ile Ile Phe Glu Leu Glu Lys Leu Thr Asn
                85                  90                  95

Asp Leu Gly Val Ala Ile Glu Gln Ile Ser Val Asp Val Tyr Trp Ala
            100                 105                 110

Ile Ile Thr Ile Val Ser Leu Thr Thr Arg Ile Asp Cys Leu Thr Thr
        115                 120                 125

Glu Ser Tyr Val Thr Glu Gln Lys Gln Glu Leu Ser His Tyr Gly Gln
    130                 135                 140

Lys Ile Asn Ile Ile Leu Ser Lys Leu Lys Lys Gln Ile Thr Leu Cys
145                 150                 155                 160

Arg Gln Gln Ile Asp Ala Ala Glu Tyr Tyr Arg Lys Leu Arg Lys Leu
                165                 170                 175

Phe Gln Thr Pro Thr Glu Ile Met Glu Val Phe Lys Ile Leu Ile Phe
            180                 185                 190
```

-continued

```
Asn Lys Asp Val Pro Gln Pro Leu Tyr Cys Gly Ala Thr Lys Thr Met
        195                 200                 205

Val Asp Ile Thr Val Leu Lys Arg Lys His Val Tyr Leu Leu Ile Ser
    210                 215                 220

Ser Leu Asp Ile Thr Glu Glu Glu Ile Ser Val Phe Gln Thr Val Tyr
225                 230                 235                 240

Asp Ser Ile Lys Thr Ser Asp Gln Tyr Glu Ile Val Trp Ile Pro Ile
                245                 250                 255

Val Glu Glu Trp Thr Val Glu Tyr Asp Asn Lys Phe Glu Asp Phe Lys
            260                 265                 270

Cys Lys Met Pro Trp Tyr Ala Val Gln His Ser Gly Pro Ile Ala Gly
        275                 280                 285

Tyr Gln Tyr Ile Lys Glu Glu Trp His Tyr Lys Ser Lys Pro Met Val
    290                 295                 300

Val Val Leu Ser Pro Gln Gly Lys Val Gln His Ser Asn Ala Phe His
305                 310                 315                 320

Leu Ile Gln Ala His Gly Thr Arg Ala Phe Pro Phe Thr Thr Val Lys
                325                 330                 335

Gln Glu Gln Ile Asn Asn Glu Thr Asp Trp Val Gly Ser Val Ile Gly
            340                 345                 350

Asn Ile Tyr Pro Ile Ile Asn Thr Trp Phe Asn Ile Tyr Asp Thr Leu
        355                 360                 365

Tyr Glu Gln Ile Lys Glu Lys Lys Tyr Ile Phe Leu Tyr Gly Gly Lys
    370                 375                 380

Asp Lys Glu Trp Ile Gln Gln Phe Thr Lys Asn Val Ser Ala Leu Ala
385                 390                 395                 400

Ser Asp Ala Ala Ile Thr Glu Ala Asn Ile Ser Ile Glu Trp Leu Cys
                405                 410                 415

Val Glu Lys Glu Asp Arg Ser Val Met Arg Arg Phe Trp Gly Gly Ile
            420                 425                 430

Glu Ser Leu Phe Val Thr Lys Val His Lys Ala Val Asp Ala Val Thr
        435                 440                 445

Leu Glu Val Gln Lys Met Leu Ser Tyr Lys Asn Glu Ala Gly Trp Ser
    450                 455                 460

Leu Leu Ile Ser Glu Gly Ser Ser Val Val Val Cys Gly His Gly Lys
465                 470                 475                 480

Thr Ile Thr Asp Thr Val Glu Gly Phe Gln Asn Trp Lys Gly Ser Leu
                485                 490                 495

Thr Lys Lys Gly Phe Gly Leu Ser Phe Gln Gly Tyr His Gln Lys Ile
            500                 505                 510

Val Asp Ile Thr His Arg Cys Ser Tyr Leu Glu Ile Ser Asn Val Ser
        515                 520                 525

Gly Arg Leu Pro Glu Thr Ile Lys Cys Pro Asp Cys Pro Arg Ile Met
    530                 535                 540

Glu Ile Phe Val Ser Tyr Lys Cys Cys His Asn Asn Thr Ile His Tyr
545                 550                 555                 560
```

<210> SEQ ID NO 9
<211> LENGTH: 1614
<212> TYPE: DNA
<213> ORGANISM: Fusarium virguliforme

<400> SEQUENCE: 9

```
atgcgggttc cgtcttcgca actccttgcg ctgtcctatg gcatcttctt aggcacagcc      60
```

```
caagccgcag tgatacctcg tgatggcgcc aagacctgca aaaagaccaa ggtcgccgtc    120
ctcggcgccg gcgtcgctgg cataacggct gctcaggccc tgcacaatgc ctcgatccat    180
gactttctca ttgttgagca caacgactac atcggcggtc gagtcaggca tgcttctttt    240
ggcaaggggc ctgacggcaa ccccttgacc gtggaactcg gtgccaactg ggtcgaaggc    300
cttggatcaa accccatctg gcgtttggct caaaagcaca aggttaagag cacctttgcc    360
gactatgact ccgtcctcac ctacgaccaa aacggatcag ccgactacgg agaggtcttt    420
gaggaattcg acgtgagctt tgaaaacgcg acaaaggacg ccggatacat ccagactctg    480
aacctccaag acacttcggt ccgtacggga ctcagcctcg caggatggaa gcccaagcag    540
gatcagtaca agcaactcgc cgactggtgg gggtgggact ttgaaaccgc ctttactccg    600
gagcagtctg gtttccagtt cggaattgcc ggaaacaatg ctacgttcaa gcatttcaac    660
gacgagtcca acctcgttat cgaccaacgg ggtttcaaca cctggatcat tggagaggcg    720
aacgagttcc tcaaaggcgg ggagcaagat cccaggctcc ttcttaacac gactgtcaag    780
aaggtccact acggcaaaga aggcgttgtt attctcaacg aggacgacag ctgcatcgag    840
gctgaatttg caatttgcac attctctctt ggtgtgctgc agaacgaagc tgtttccttt    900
gacccggtcc tcccccgctg gaagagagaa gccatcgagc aattccagat gggcacctac    960
accaagatct tcatgcagtt caacgagtcg ttctggccag aagagggtca atactttctc   1020
tacgctgatc ccgaggagcg aggctatttc cccctttttcc agccgctaaa cgccaagggc  1080
ttccttgagg gctctaatgt tctctttgct accgtcgttg cttcgcaggc gtacaaggta   1140
gaggcacaat cggacgagga aaccaaggag cagattcttg aggtgcttcg atccatgttt   1200
cctgataagc acgtccctga gccgattgac tttatgtatc ctcgatggac gtcaacagag   1260
caagtcccct ctccttgttt gcatttgtca caattactaa ccacattctt caggtggtcg   1320
tatggctctt acagcaactg gccagtcggc atgaccctcg aaaagcacca gaaccttcgt   1380
gccaacgttg accggctgtg gtttgcaggc gaggccaact ccgcagagtt tttcggatat   1440
ctgcatggag cgtggtatga gggtcaagag gcaggagagc ggattgccag gattattggt   1500
ggaaaggaaa cagagaagtc gcagcagatg aagaagtatg aggttcttca tggaacgacg   1560
actgcggatg agtataatga cgccaacggg tggtcgacgc cattggatgt ctaa         1614
```

<210> SEQ ID NO 10
<211> LENGTH: 537
<212> TYPE: PRT
<213> ORGANISM: Fusarium virguliforme

<400> SEQUENCE: 10

```
Met Arg Val Pro Ser Ser Gln Leu Leu Ala Leu Ser Tyr Gly Ile Phe
1               5                   10                  15

Leu Gly Thr Ala Gln Ala Ala Val Ile Pro Arg Asp Gly Ala Lys Thr
            20                  25                  30

Cys Lys Lys Thr Lys Val Ala Val Leu Gly Ala Gly Val Ala Gly Ile
        35                  40                  45

Thr Ala Ala Gln Ala Leu His Asn Ala Ser Ile His Asp Phe Leu Ile
    50                  55                  60

Val Glu His Asn Asp Tyr Ile Gly Gly Arg Val Arg His Ala Ser Phe
65                  70                  75                  80

Gly Lys Gly Pro Asp Gly Asn Pro Leu Thr Val Glu Leu Gly Ala Asn
                85                  90                  95

Trp Val Glu Gly Leu Gly Ser Asn Pro Ile Trp Arg Leu Ala Gln Lys
```

-continued

```
            100                 105                 110

His Lys Val Lys Ser Thr Phe Ala Asp Tyr Asp Ser Val Leu Thr Tyr
        115                 120                 125

Asp Gln Asn Gly Ser Ala Asp Tyr Gly Glu Val Phe Glu Glu Phe Asp
    130                 135                 140

Val Ser Phe Glu Asn Ala Thr Lys Asp Ala Gly Tyr Ile Gln Thr Leu
145                 150                 155                 160

Asn Leu Gln Asp Thr Ser Val Arg Thr Gly Leu Ser Leu Ala Gly Trp
                165                 170                 175

Lys Pro Lys Gln Asp Gln Tyr Lys Gln Leu Ala Asp Trp Trp Gly Trp
            180                 185                 190

Asp Phe Glu Thr Ala Phe Thr Pro Glu Gln Ser Gly Phe Gln Phe Gly
        195                 200                 205

Ile Ala Gly Asn Asn Ala Thr Phe Lys His Phe Asn Asp Glu Ser Asn
    210                 215                 220

Leu Val Ile Asp Gln Arg Gly Phe Asn Thr Trp Ile Ile Gly Glu Ala
225                 230                 235                 240

Asn Glu Phe Leu Lys Gly Gly Glu Gln Asp Pro Arg Leu Leu Leu Asn
                245                 250                 255

Thr Thr Val Lys Lys Val His Tyr Gly Lys Glu Gly Val Val Ile Leu
            260                 265                 270

Asn Glu Asp Asp Ser Cys Ile Glu Ala Glu Phe Ala Ile Cys Thr Phe
        275                 280                 285

Ser Leu Gly Val Leu Gln Asn Glu Ala Val Ser Phe Asp Pro Val Leu
    290                 295                 300

Pro Arg Trp Lys Arg Glu Ala Ile Glu Gln Phe Gln Met Gly Thr Tyr
305                 310                 315                 320

Thr Lys Ile Phe Met Gln Phe Asn Glu Ser Phe Trp Pro Glu Glu Gly
                325                 330                 335

Gln Tyr Phe Leu Tyr Ala Asp Pro Glu Glu Arg Gly Tyr Phe Pro Leu
            340                 345                 350

Phe Gln Pro Leu Asn Ala Lys Gly Phe Leu Glu Gly Ser Asn Val Leu
        355                 360                 365

Phe Ala Thr Val Val Ala Ser Gln Ala Tyr Lys Val Glu Ala Gln Ser
    370                 375                 380

Asp Glu Glu Thr Lys Glu Gln Ile Leu Glu Val Leu Arg Ser Met Phe
385                 390                 395                 400

Pro Asp Lys His Val Pro Glu Pro Ile Asp Phe Met Tyr Pro Arg Trp
                405                 410                 415

Thr Ser Thr Glu Gln Val Pro Ser Pro Cys Leu His Leu Ser Gln Leu
            420                 425                 430

Leu Thr Thr Phe Phe Arg Trp Ser Tyr Gly Ser Tyr Ser Asn Trp Pro
        435                 440                 445

Val Gly Met Thr Leu Glu Lys His Gln Asn Leu Arg Ala Asn Val Asp
    450                 455                 460

Arg Leu Trp Phe Ala Gly Glu Ala Asn Ser Ala Glu Phe Phe Gly Tyr
465                 470                 475                 480

Leu His Gly Ala Trp Tyr Glu Gly Gln Glu Ala Gly Glu Arg Ile Ala
                485                 490                 495

Arg Ile Ile Gly Gly Lys Glu Thr Glu Lys Ser Gln Gln Met Lys Lys
            500                 505                 510

Tyr Glu Val Leu His Gly Thr Thr Thr Ala Asp Glu Tyr Asn Asp Ala
        515                 520                 525
```

-continued

```
Asn Gly Trp Ser Thr Pro Leu Asp Val
    530                 535
```

<210> SEQ ID NO 11
<211> LENGTH: 1165
<212> TYPE: DNA
<213> ORGANISM: Glycine max

<400> SEQUENCE: 11

```
gtggatcatt gggttctaga tcaaccttac cttttgatta aggaaatcta attagtataa     60
gattacctgg tgataatgat gcgatatgat gacgagttat ttgcataacg tttcgatcat    120
ccacgatacc acgtccatgt tcaggttgaa actcttttaa tgtttattgg tggggatgtt    180
ataacccggc ccagacctaa ttaatgcatt gaatgtcgaa ggtgaattgg tccaaacttc    240
tttttcctc ttttatttc gagaatcatg cttatagttt tacccggatc ctcctatgag    300
aagaaaaaat cgaacgaagg gaaatcaaac tgttgcctaa agataagaaa aaataaatta    360
atttcataaa aattaagttt tttaattaat taatatataa ataattttgc gaaaaactac    420
gtgatcttaa gtttctaact gcatgggaaa attatggaag tgtagagatc attcttgttg    480
aagtaaaact aaatttttca agatttttct ttaaataaag taaataatga gattttgata    540
aaaaaaaatc ttaattttaa aaataataat aataatgatt tttcattttc ataatttatg    600
tttcaaataa aagaggttaa ataaaaaatt aaaatttatt aatactttac acattaacta    660
aagataaggt ttttaacaaa tgcattaaaa gtgcaatcga tcgaccagtt tccacttttc    720
tatccataag tagacttcca aaccaacaaa gaccttttca atgactagtt ctgtaaaaat    780
agtaaagatt tttatcgatt tatgtttcgt ctctcgtcgc aacctccgag catgttgtga    840
caataagtaa aaaacaaaat tgtaagagtt taaatttttt tagctaaatt taattttttt    900
ttcattagta taaattttgt ttatattatt tatttatttt cacttatact acaattcatt    960
caaataaatg atgataaatt tgtctatttt tttttatttc tatgatctat ctaaataata   1020
cacctttct gctctatttg tcatttaatt ttatcctttc tatttcatac aaatcaccaa   1080
tccaaataaa tttctttagt ttataaaagg tgagatagtc tcaaagctaa cgttgaataa   1140
cgttgaaata cttgatagat tgatc                                         1165
```

<210> SEQ ID NO 12
<211> LENGTH: 1356
<212> TYPE: DNA
<213> ORGANISM: Glycine max

<400> SEQUENCE: 12

```
gcctaagaca tggaggggaa aataaatgta tgtacattct gcttgttttc tcaaatgctg     60
actggttaag atatttagag tgggtataat atttgtccag aaggataaag ataaaataaa    120
acacgttaat tatccttatg attttgcaac tgtaaaatat aacaggggag gagaaggatc    180
acaattttac cagtggatat tccaagtttc ataaattaaa atgaaactca gattcataaa    240
ttttgaagtc attgtcatga aactctttaa ttacctgctt tgtaacaact ttcttgttgg    300
taccattact atcttattct tgtcctattg catgggtaga aaaaagaaaa atatagggaa    360
acaaaataaa agagagaaaa tgatagatat gatacatgat ttgatgagaa atgaaaaaag    420
aaataagaaa aaatagaata gaaatgacat ggaattgaaa aataaatgtt tgataatgta    480
tgtttatata taattactct ttcttgggtt tctaccaaat ctgatatctt tcttgggtag    540
gaactaggaa ccattcattt acgtcacttg tgtgagtgag tcatcttcaa acactgtagt    600
```

```
gcgtttgaaa tcctttggta gtgtaagaaa acaaatcaaa gctaggatgc aacttagtta    660

ttccccggat agaaatctcg gatcaaagac tttatggaca agataaatat acaaaagtgg    720

acactcgttt ctttcaaaat ataattacga gttgatacat atttgaaaat ttaatcaatt    780

tttttgtctt aaataatttc cattatcctc cacttactct atacgatatc tataccgcaa    840

catgaaggac caattaaaga ctttggcaaa aataaaataa aaccattgag gtgtagcact    900

agttccggtc ttctaaatgc tcacaagatt ttaattagcc gccgggtctc aaaattaaca    960

tgttctaaat catgcaccag ctcccattat aaaactaaat atttcaggca caggtagtgg   1020

atacgtacaa tgtcgaatgt acactgtaat actgaaaaat ttatcatgac aagcgtgcag   1080

acattaagaa tgcttccacc atcaaatagt ttactaattc tacaaatgct aaaatatcta   1140

tatcaatggc tccgtaccct ataaatagct agcttcccat gctacaaaat acacatctct   1200

cacacactta gaattaagtt agtagcgagg aagaaaaatg aaggttgttt acctcttcgt   1260

tgtgctgatg gctttggcat catctgttgc ctttgcttat gatccaagcc ccctgcaaga   1320

cttttgtgtc gctatcaatg acaccaaagc tggtgg                             1356
```

<210> SEQ ID NO 13
<211> LENGTH: 1775
<212> TYPE: DNA
<213> ORGANISM: Glycine max

<400> SEQUENCE: 13

```
cggtcccaac aactagtttg cattctcata tcatatattg cccaaaaata tttctcggtt     60

cataacctca aggtccgttt gatttgaaga acaaaaatgg gaaggccatt aaatttgcaa    120

agaatttcaa gatgggataa cacaacaaaa aaaattattt atttaatttt tcaagtggtc    180

atgaaatagt attaaaaatg ataaaatgct gaacaccaaa ttatgaagat aaaaatacta    240

ctcaatttac cttttcatta ttatgctaaa tcttgactct cccagacatt aaaactacag    300

tcatatgtaa tcatcactac cactttgaat gccactatca ttatctccat cttcttcatc    360

tttatcattt cttataaaga taactttgtc aattcttaag aatttatatt attatatttg    420

ccaagttatt cggtacacat aaaatactga ataagataag cttatatatt atacgcaatt    480

tttcattagt ccatctaata cttatgcgta tcaaacatca tacagtaaaa gaaaaatatt    540

tgcgttgtat ttcaatttca aaataataga ctgatcaagg tgtgctatta ctcaactata    600

ccatacagta ttacagtcct ggagtgcata ttctatttct caataaacaa caaacgtagt    660

tgttggtttt gagattttga atattatatg aattttccta ttcgcctaag actatggagg    720

ggaaaataaa tgtatgcact ttctgttttc ccgaatacct actgcttaag atattaagag    780

tgggtataat atttgtccag aagggtaaag ataaaataaa actcgttatg cttatgattt    840

cgcaattgta aaatagaaca ggggtggaga aggatcacaa tttttccagt ggatattcca    900

agtttctaaa actaactcag attcataaat tttgaagtca ttgtcattaa agtctttaaa    960

tacctgcttt gcaactcttc ttttcggtac aagtcttttc ttacccttat cctattgcat   1020

gggtagaaaa aaaaaagata aggaaacaaa taaaagaaaa aagacaaaat gatagatatg   1080

ataactgatt tgatgaaaaa tgaaaagaag aaataataag aaaaatagaa tagaaatgaa   1140

atggaagtga aagaaaatgt atgataatgt atatgtgtgg taatttctac aaaatctgat   1200

atctttcttg ggtaggaacc attcatttac gtcacttgtg tgagtgaggc atcttcaaac   1260

actgtagttc gtctgaaatc cttgggtagt gtaagaaaat aaatcaagga tgcaactaag   1320
```

-continued

```
ttattgcctg gatagagatc tcagatcaga gactttgacg acaagataaa tatgcaatag   1380

tggacactcg tttctttcaa aatataatta cgggttgata cttggaagaa aatttaatca   1440

attttttgcc ttaaataatt tccattatcc tccactttct ctatacgata tctataccgt   1500

aacttgaaga accaattaaa gacttaggct aaaataaaat aaaaccattg aggtgtagca   1560

ctagttctgg tcttctaaat gctcagaaga ttttaattag ccgccaggtc tcaaaacaaa   1620

catgctctaa atcatacacc tgctcatatt ataaaagtaa tatttcaagc acaggtagtg   1680

gatacgtaca atgtcgagtg tacatggtaa tactgaaaaa atcatcatga cgatgatgtg   1740

gggcatctta atctaatatt ttgacaagcg tgcag                              1775


<210> SEQ ID NO 14
<211> LENGTH: 248
<212> TYPE: DNA
<213> ORGANISM: Fusarium virguliforme

<400> SEQUENCE: 14

ggtggtcgta tggctcttac agcaactggc cagtcggcat gaccctcgaa aagcaccaga     60

accttcgtgc caacgttgac cggctgtggt ttgcaggcga ggccaactcc gcagagtttt    120

tcggatatct gcatggagcg tggtatgagg gtcaagaggc aggagagcgg attgccagga    180

ttattggtgg aaaggaaaca gagaagtcgc agcagatgaa gaagtatgag gttcttcatg    240

gaacgacg                                                             248


<210> SEQ ID NO 15
<211> LENGTH: 883
<212> TYPE: DNA
<213> ORGANISM: Glycine max

<400> SEQUENCE: 15

atgaagaaac tgaagaacac acaattctca agtcaacaag gtgcagcagc ttcacaaccg     60

agaccactgc tgcacaagga acttgttggg gagaaaaaag ttatgaattc tgagtttaat    120

gaagctgttg aaaaaggaga tatggataac tttgttaacg tgttggagca agtttgtaga    180

gaaaggaacc tacctttgtc tgctgttttt gatcaagtca cctggactgg tgattcgttg    240

cttcatgtgg cagcagataa ggggaaacaa catattgtag agctgattgc tgatcacttt    300

caagagcttc ttattagaag aaacgctaga ggtgatactg cacttcatgt tgctgtgagg    360

tctatgaact ccaatatagt caagttcatt ctcaacaaag ataaaaagct agcaaaagaa    420

aagaatcaat atgggaacac tcctttgcac gaggctgtct acagtgagca tgttgatgtg    480

gttaatcaga ttttacttgc cgataaggat gtggttcatt ctttgaacaa gtcaaaccaa    540

tcaccgttat atttggcagt tgcgaatggg aacttggaaa ttcttaatct tctattggat    600

gttccattac cttcagatct tccacggtgc cttggaaact ctccacttca tgctgccata    660

ctggaacgga agcctggtat tcagttttta tttttctttt caaatcaatg actatatatt    720

catggtactt taattaaaca ctacatatgg accagtaata tggcccaata attaaaatat    780

atagctggtc agtagagtaa tctatacctt ataaattggt tttgttaagt tatatgcaaa    840

cctaaactat aagatagtat tagagattca gaatctatct taa                     883


<210> SEQ ID NO 16
<211> LENGTH: 1450
<212> TYPE: DNA
<213> ORGANISM: Glycine max

<400> SEQUENCE: 16
```

-continued

```
caatagaagc ataaaaaatc aactacctta gaaaaggagt gaaaggaaga aaagagaaac     60
aagaatggaa gtgacacaag tactgcacat gaatggaggc tcgggagaaa caagctatgc    120
aaacaattcc ttagttcagg tataaatgca tgtttaataa caagtaaaat ctcatcatct    180
tctacttttt ttttctccat tgcattcatt aattggcaat taattttatg ttcatatata    240
tgtttagaca aattaatttt tgctagctag gttaagaaac tttgatagta atagcaaaga    300
gctatgcaga aagtttgata tttattggtt ggaactgatc tgaatgaatg aatattgcag    360
caaaaggtga tttgtttgac aaagggtatg agagaggaag ccataagcag cctctaccgc    420
agcatgctcc caagaagcct tgcagttgcg gacttgggtt gctcttctgg accaaacact    480
ttcttcgtga tatctgaagc tataaaatcg gtggagaagc tttgtcgaga actgaatcat    540
cagtcaccag aataccagat ctacatgaac gatcttcccg ggaatgattt caacaacatc    600
ttcaagtccc ttgacagctt caaagagaaa ctgtgtaatg aaataataga agctgggcat    660
ggaattggtt catgtttttt caatggggtt ccaggttctt tttatggcag gatctttcca    720
accaaaagtc tgcattttgt tcattcctcg tacagcctta tgtggctatc caaggtatac    780
tataatttct ctgttaattt ttttttgtag accacacata atattcattt gactgtaata    840
atttcacgtt aattaatcta tgtgttcagt gaatattatg ttaactatac aatagcacca    900
gattattatt acaagtccta taggagtgac aaagtattat attttcctca caataaaatc    960
aattttttgt gtaaaaaatt gaaataaatt aaataaactt tctatagata tcctgcgcaa   1020
cacacctttc tataggagtg acaaacttat tacagatgca agattaaaat aattatgtgt   1080
ttattgatta ttaattaggt tcctgatggt gtagagaaca ataagggcaa catttacatg   1140
gccagcacaa gttccttaaa tgtccttaag gcttattacg agcaatatca aaaggatttc   1200
tcgttgtttt tgaagtgtcg agcggaagaa atcgtggaag gggtcgtat ggttctgaca   1260
tttttgggaa gaagaagcga cgatcgatct agcaaagagt gttgctatat atgggaactt   1320
ttggctatgg ctcttaatga tatggtctcg aaggtactta tgaaaaaatg gttaatgaag   1380
aatagtttga aaataatttt aatattttat taaataagat aaaattggtt aaaatttatt   1440
tatatttaaa                                                          1450
```

<210> SEQ ID NO 17
<211> LENGTH: 998
<212> TYPE: DNA
<213> ORGANISM: Glycine max

<400> SEQUENCE: 17

```
gttatccaag ccatgtggga aactctaagt gtagggtgta tcataagtgg tagttgcctt     60
attgttccta catagctgtg atgtaagagt ctctttgagg atgctatgcc acccttcccc    120
aactagcttt gattggtctt gtggggtctt caaaagcctt aaccaaaaag ggatagtaac    180
attcaaaatg gttaatgttt aatgcaccat tttaccaact taaaaatcgt gaccatatta    240
tgatgtaaca agtttaattt tcctaagtcc tatataagtt caacccttgg ctcaatcttt    300
caacaattca gttgcttact aatactaatc tcttaattct ctttggccat ttctttagta    360
acattaagat aatgtattct gtggaaatgg caccttatgg tagattcatt gctaacattt    420
tgatagctgt gatgtttgtt tgcttgtttt ttgtgaccaa cattgtggca caggattcag    480
agattgctcc tacaggtcaa ttggaggctg gaactgggtt tgatttgcct gtttctaagg    540
tgatgatgtg ttcttcagtg ttggcatctc ttttggcatt catgttgcag tgaattggaa    600
```

```
gacagtgggt ttcaaatttg aacttgttgg ggataatctt actttgtatg tgggttaaaa    660

ttcatatgtt tatatatata ctatatacta tatgtttggt tgttgaaaat ggtactgtat    720

ttttgggcat tttgtaagat tagctttatg aggagctaca gttacaagta tgtaatttct    780

actcagctat tattggtgtg agctgatata ttaatataat tgttaagttc cttgtaattg    840

atgattttg ctgtttcaag ttatcaaatt cttcgaaagt gactttcttg tagcatgctg    900

ctttgaatta tagtccaact ttgtccaaaa atgtgacatt tgaagtataa taactggata    960

agtaaacaat tcctatttta taaatttgag tctttatt                            998
```

<210> SEQ ID NO 18
<211> LENGTH: 4142
<212> TYPE: DNA
<213> ORGANISM: Glycine max

<400> SEQUENCE: 18

```
atgtcatgca aacctccaag tgatgtaatt gctcacaaaa ctacactggc catactgaac     60

aatctcaaaa actatgagtg gaatgcaaag gcagtgctga cactggcagc ttttgcactc    120

gaatatagcg agttttggct gctagcacag taccaacaat cagaccctct tgcaaaatct    180

gtggctattc tgaagagagt gccagtgctc acaaggcaag cagcacttca aaagtatcgc    240

caagccatcg ttgaggttaa cgatttggtg aaagcaacgt tgcaagtcat tgaagttaat    300

tatctttgag ttggagaagc ttactaatga tttgggggtt gcaatagagc aaatctctgt    360

tgatgtttac tgggcgatca tcactattgt ttccttaacc actcggattg attgtctcac    420

cactgaatcg tatgttacgt acgtacattt catactatcg tatataataa aacctaatta    480

ctttattgca atgaaaatct taaaatgtat aattttattg attatttaag agagcaaaaa    540

caagaactgt ctcactatgg acaaaagatc aacatcatac tcagcaaact caagaagcag    600

atcactcttt gcagacaaca gataggtcag caattgaaat aattgccttt gcatgccttt    660

aattattaat tctgtcatca tgttttttc tccttaaagc aaatatgctt ttgattcaaa    720

cttcaaagct atgatttcat ggaataaaag gcaccgagca gtgaatgaga ttctaattaa    780

ttaaaggatt tgtttctgtt atttcagatg cggcagaata ttatcgcaag ctgaggaagc    840

ttttccaaac tcccactgaa ataatggagg tgtttaagat tctgattttc aacaaggatg    900

ttcctcagcc actttattgt ggtgctacta agaccatggt ttgtgattcc ctgttaaaat    960

cctactttca tgttcgaaat ttgttctctt cggagagaaa atgagtgtga attttctggt   1020

ttggttggtc aatatcctac tcatattcta ggctttagaa ataaaacacc agataaagtg   1080

gagggagggg gtgtcgaaaa cctagaacta aaatgaatat aatgttaatg cataaaaaat   1140

aaacatgact tatgccacac cttcgcattg atcctctgtt agttcctcaa accacacacg   1200

gacactctcg tccctatgat ggagaaagtc gatagcttgg cctccacatc gaagtcagac   1260

tctgacaaca gccaccacct cacccctcac gagttcacta ctcccatccc ctttgtaacg   1320

aaacaccaca cctacctcgt cggcttcagc caatgctcct tcctcctcac gcagcacatc   1380

catgcgccac atgacatcgt cttctagcgg cttcattgga tctgcaccgc tctaacccca   1440

acactaccct ctttgccacc ttcaccaaat aggcactgcc ccaaccccaa ccaccttgtt   1500

atggaatgcg accctggagg tgctaatcgt tgagaagacg gaaggatttc gcaaagcacg   1560

gaagagtgtt gatggttgat tggatgtttt cacgttgagt aattttgtgt ttgattgatg   1620

ttttctgggt tacagatgct tcgtgatttt gtgtttttat ctttacttta attgattctt   1680

ttacagctgc caaaaattat aattataatt tcgaaatgaa tattgattat tttttaagcg   1740
```

-continued

```
tcacaaatga tattttaaaa aaaagttaac aacaacatca tcactagcta atagaaaaat   1800
tctaacaacg agaattaaaa acaaaaaatt tcaaatataa aaaaataaaa acgaacaaaa   1860
ttttaatgag agatcaaaaa taaaatttaa gtatatataa gagagtacta acatatttaa   1920
tcttatttta attaaaaaaa ttgtttttaa aaatattaat aataatgtaa tttgtttgtt   1980
tttttataa aaaaaatgac aagtttgacg aaagttattt gtttgatatt catctcactc   2040
accctcgaat caacccaaaa agtcaagtta aaaaaaataa ttgagtaatg atatatgaag   2100
tactctttat ttaaatttta tttttaaata ctccatcaat atcttttaat tttctttatt   2160
actatcacat catgaattct atatacatat ttttgttcat ttttaaaaac catgtgatat   2220
ttatcaaaca tttttcaaaa taattattgg atgtcgacga gcatttgaaa aaggatagct   2280
catttgaata caatttaata ataaatctga tgataactat aaatataaga tagtgatcta   2340
aaagaatcta ctgaagattg aagaaagatt aatttaacta tacagaaata taagatggga   2400
tctaaaagaa ttaatcaagc ttcaagttgt ataatggggt taaatggtta tctcatgtat   2460
atgtttgttt tgtgtcatct ttcctgggtt agtaagtatt tgtatccact tattgggtat   2520
aaatattatc taaccttaat tgggtcatgg cccttggcaa tgatggctga ctttgtagtt   2580
ggtgttatgg tatcactggt acccttctta atgtaataca tttgctgcat gatccaaaaa   2640
aaaatattat tctcagttca gattttcaca acaatttcta caataaagaa agagaagaga   2700
agagtgagat aaaaacaagt attgtaaaat aagtaaggaa aaataagtgt tgtacgtgag   2760
aaatttgaaa aaagattatc cctattcccg tgtctgtgaa attcgatgct ttcaagtatc   2820
attcatttca agcatctgta atttttaatc ctgattcagt tgttgcttgc tacgtaggtc   2880
gacatcactg tgctgaaaag gaagcatgtt tacttgttga tttcttccct agacattacg   2940
gaggaagaga tttcagtatt ccaaacagtt tatgattcaa ttaaaactag tgatcagtat   3000
gagattgtat ggattcccat tgtggaggaa tggaccgttg agtacgacaa caaatttgag   3060
gattttaaat gcaagatgcc ttggtatgcg gtgcagcatt ctggacccat agcagggtac   3120
cagtacatta aggaagaatg gcactataaa agcaagccta tggttgtggt gttgagtcct   3180
caagggaagg tgcaacactc aaacgcattc catttgatcc aggctcatgg aaccagagct   3240
ttccccttca caactgtcaa acaagaacaa atcaacaatg agaccgactg ggttggctcc   3300
gtaataggca atatttaccc catcataaac acttgggtaa gtaaatttca cagaaaacaa   3360
aagttgttag aatatcatat aaatatatat catgagttta atggttattt actacacttg   3420
acagtataaa gtaatttcac aaattatcac gtatatgaat tatcatacat gatgaagtag   3480
gattaaataa tactataaaa ttattttacg ttgtgttaga ttttctctac attatatact   3540
agtttaatat ttatgatact ttatatgagc agatcaaaga gaaaaagtac attttcttgt   3600
acggaggcaa ggacaaagag tggatccaac agttcaccaa gaatgttagt gcccttgcaa   3660
gtgatgccgc tataacggag gcaaatattt ccatagagtg gctttgtgtg gaaaaggaag   3720
acagaagcgt gatgaggcgc ttttggggtg gcattgagag tttgtttgtg actaaggttc   3780
ataaggcagt tgatgcagtg actctagaag tgcaaaagat gctctcttac aagaatgaag   3840
ctggatggtc tctccttatt agcgaagggt cttctgtggt ggtgtgtggt catggaaaga   3900
caatcacgga tacagtggaa gggtttcaga attggaaagg aagtttgacc aaaaagggct   3960
ttgggttatc cttccaagga taccatcaga agattgtgga catcactcac cgttgctcat   4020
accttgaaat ttctaatgtt tcaggaaggt taccagagac catcaaatgc ccagattgtc   4080
```

-continued

```
cacggattat ggagattttc gtcagctata aatgctgcca caacaatacc attcactact   4140

ag                                                                    4142
```